(12) United States Patent
Bell et al.

(10) Patent No.: US 9,447,116 B2
(45) Date of Patent: *Sep. 20, 2016

(54) INHIBITORS OF HIV REPLICATION

(71) Applicant: VIIV HEALTHCARE UK LIMITED, Brentford, Middlesex (GB)

(72) Inventors: Andrew Simon Bell, Deal (GB); Iain Brian Gardner, Sheffield (GB); Karl Richard Gibson, Sandwich (GB); David Cameron Pryde, Granta Park (GB); Florian Michel Wakenhut, Le Vert Village (FR)

(73) Assignee: ViiV Healthcare UK Limited, Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/322,134

(22) Filed: Jul. 2, 2014

(65) Prior Publication Data

US 2014/0315927 A1    Oct. 23, 2014

Related U.S. Application Data

(63) Continuation of application No. 13/295,167, filed on Nov. 14, 2011, now Pat. No. 8,809,363.

(60) Provisional application No. 61/413,618, filed on Nov. 15, 2010, provisional application No. 61/485,355, filed on May 12, 2011.

(51) Int. Cl.
| | |
|---|---|
| *A61K 31/44* | (2006.01) |
| *C07D 495/14* | (2006.01) |
| *C07D 495/04* | (2006.01) |
| *A61K 31/4365* | (2006.01) |
| *A61K 31/506* | (2006.01) |
| *A61K 45/06* | (2006.01) |

(52) U.S. Cl.
CPC ......... *C07D 495/14* (2013.01); *A61K 31/4365* (2013.01); *A61K 31/506* (2013.01); *A61K 45/06* (2013.01); *C07D 495/04* (2013.01)

(58) Field of Classification Search
None
See application file for complete search history.

(56) References Cited

U.S. PATENT DOCUMENTS

| | | |
|---|---|---|
| 8,609,653 B2 | 12/2013 | De La Rosa et al. |
| 2012/0059028 A1 | 3/2012 | Bardiot et al. |

FOREIGN PATENT DOCUMENTS

| | | | | |
|---|---|---|---|---|
| WO | 2005/076861 A2 | 8/2005 | | |
| WO | 2010/130842 A1 | 11/2010 | | |
| WO | WO 2010/130842 | * 11/2010 | ........... | C07D 495/04 |
| WO | 2011/015641 A1 | 2/2011 | | |
| WO | 2011/076765 A1 | 6/2011 | | |
| WO | 2012/065963 A1 | 5/2012 | | |
| WO | 2012/102985 A1 | 8/2012 | | |

OTHER PUBLICATIONS

Form PCT/ISA/220 for PCT/IB2011/054652 dated Jan. 26, 2012.
Co-pending U.S. Appl. No. 13/518,434, filed Jun. 22, 2012.
Co-pending U.S. Appl. No. 13/388,712, filed Feb. 3, 2012.
Co-pending U.S. Appl. No. 13/885,526, filed May 15, 2013.

* cited by examiner

*Primary Examiner* — Craig Ricci
(74) *Attorney, Agent, or Firm* — J. Scott Young

(57) ABSTRACT

The present invention relates to novel 2,3,4-substituted 5,6,7,8-tetrahydro[1]benzothieno[2,3-b]pyridine compounds and pharmaceutically acceptable salts thereof, to compositions containing such compounds and to the use of such compounds as inhibitors of HIV replication.

2 Claims, No Drawings

INHIBITORS OF HIV REPLICATION

The present invention is directed to 2,3,4-substituted 5,6,7,8-tetrahydro[1]benzothieno[2,3-b]pyridine compounds and pharmaceutically acceptable salts thereof and their use as inhibitors of the replication of human immunodeficiency virus (HIV). The compounds of the present invention are useful for directly or indirectly inhibiting the activity of one or more HIV proteins and for treating diseases or conditions mediated by HIV such as, for example, acquired immune deficiency syndrome (AIDS). Whilst not wishing to be bound by any specific theory, it is believed that the compounds of the present invention inhibit HIV replication by direct or indirect inhibition of the interaction between the HIV integrase enzyme and endogenous lens epithelium-derived growth factor (LEDGF). For a discussion of this mechanism as a possible target for HIV therapy, see Llano, M et al. Science, 314, 461-484 (2006).

WO2010/130842 discloses thieno[2,3-b]pyridine derivatives having antiviral activity, more specifically HIV replication inhibiting properties.

Despite the large amount of research already performed in this area, there is still a stringent need in the art for potent inhibitors of HIV. Therefore a goal of the present invention is to satisfy this urgent need by identifying efficient pharmaceutically active ingredients that are active against HIV, less toxic, more stable (i.e. chemically stable and metabolically stable), effective against viruses resistant to currently available drugs and/or which are more resistant to virus mutations than existing antiviral drugs and that can be useful, either alone or in combination with other active ingredients, for the treatment of retroviral infections, in particular lentiviral infections, and more particularly HIV infections, in mammals and more specifically in humans. It is also known to those skilled in the art that the physicochemical properties of known drugs as well as their ADME-Tox (administration, distribution, metabolism, excretion and toxicology) properties may limit or prohibit their use in the treatment of diseases. Therefore, problems with existing drugs which must preferably be overcome can be selected from poor or inadequate physicochemical or ADME-Tox properties such as solubility, LogP, CYP inhibition, hepatic stability, and plasma stability. In particular, it would be advantageous to provide a compound with pharmacokinetic (PK) properties that make it suitable for once-a-day dosing, i.e. providing the right balance of absorption, metabolism and excretion properties to achieve an exposure profile which is consistent with once-a-day dosing. Furthermore, another goal of the present invention is to complement existing antiviral drugs in such a way that the resulting drug combination has improved activity or improved resistance to virus mutation than each of the individual compounds. Once again, it would be advantageous that such a combination would provide a regimen suitable for once-a-day dosing.

In a first aspect, the present invention provides a compound selected from

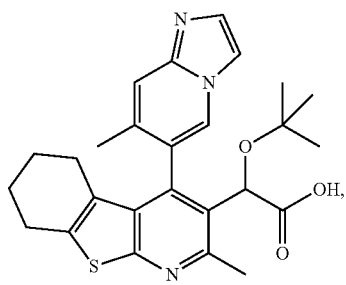

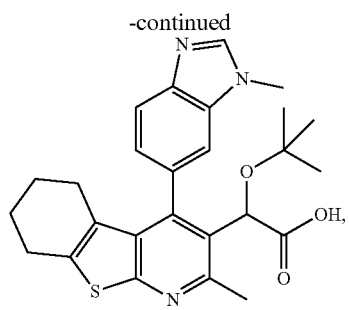

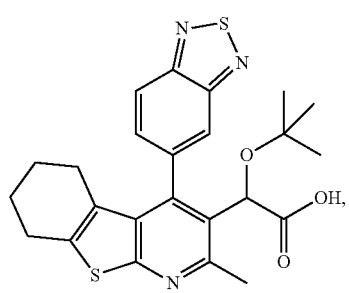

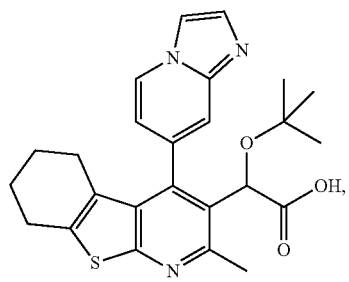

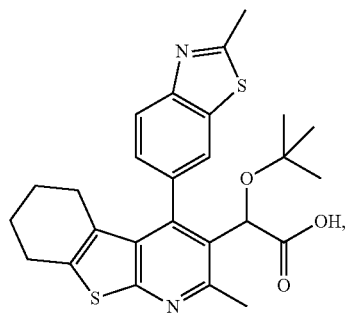

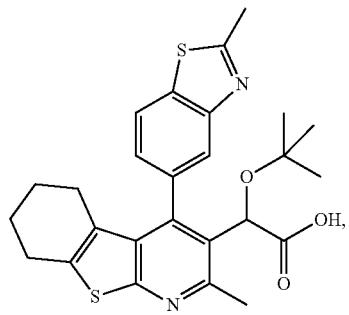

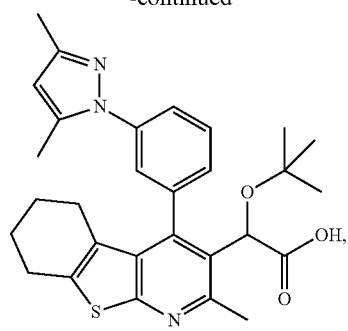
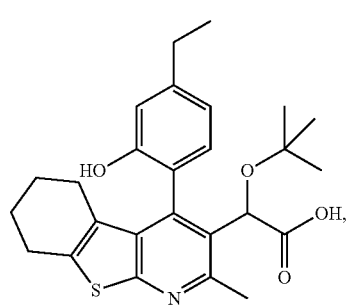
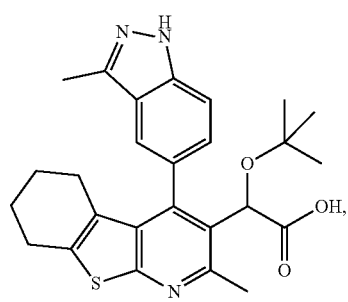
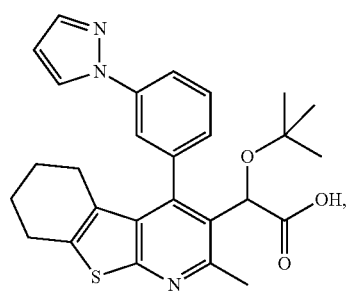
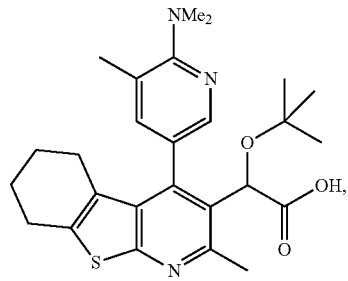
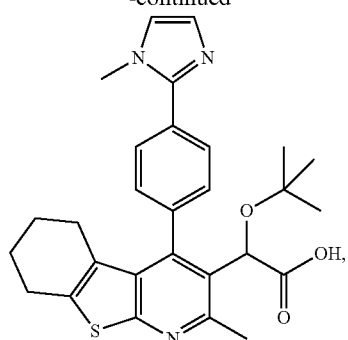
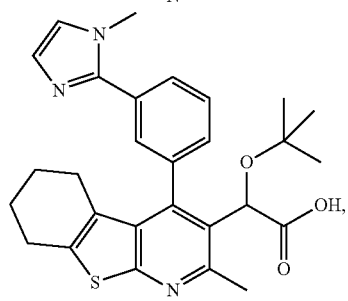
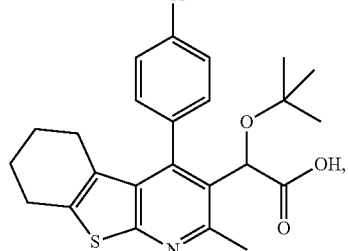
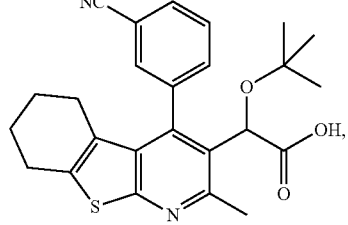
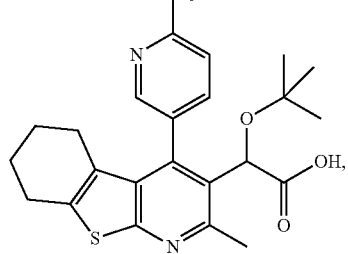
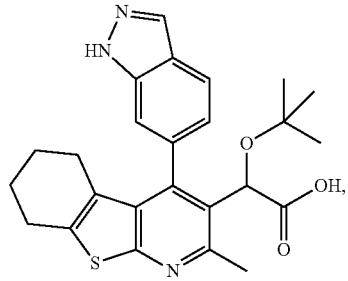

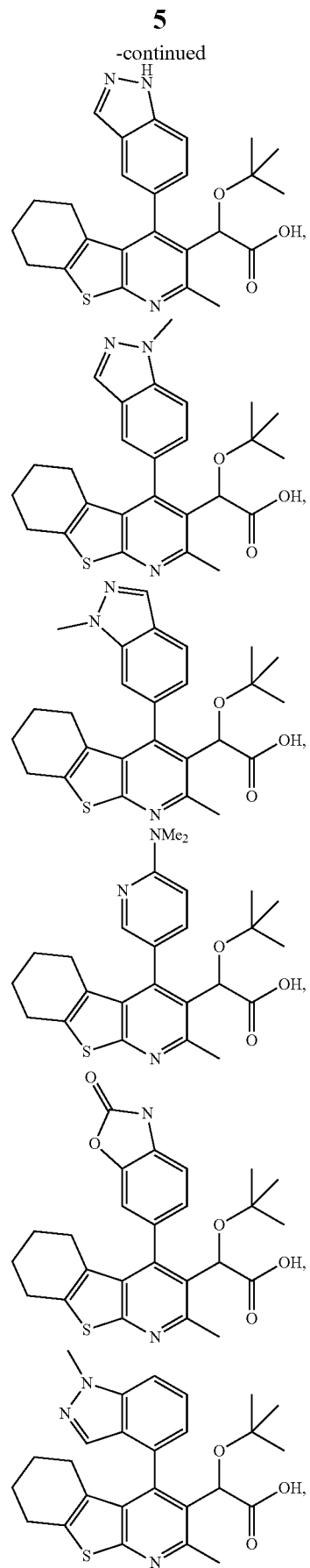
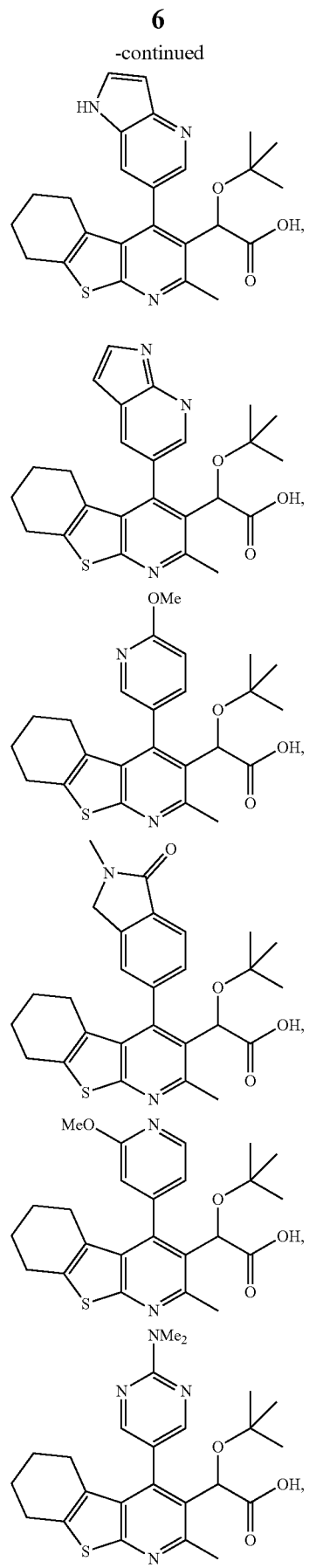

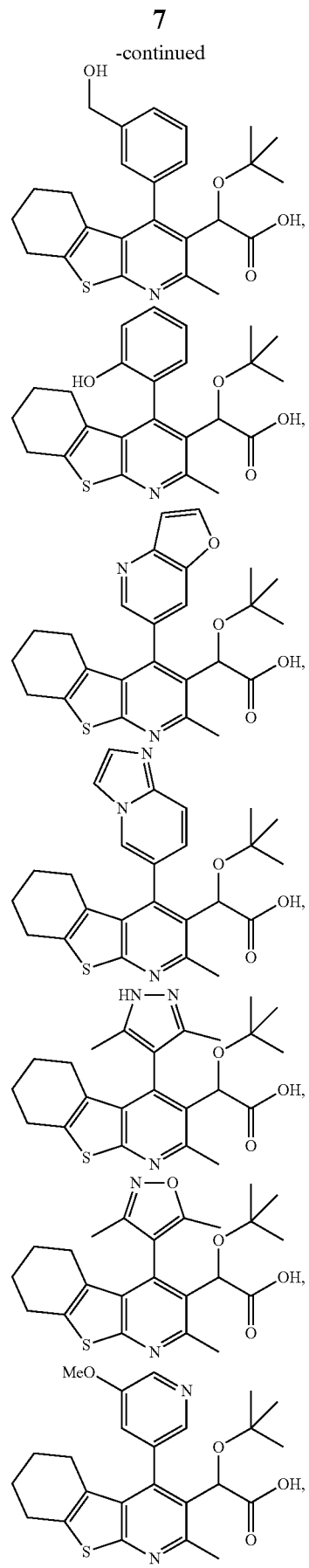
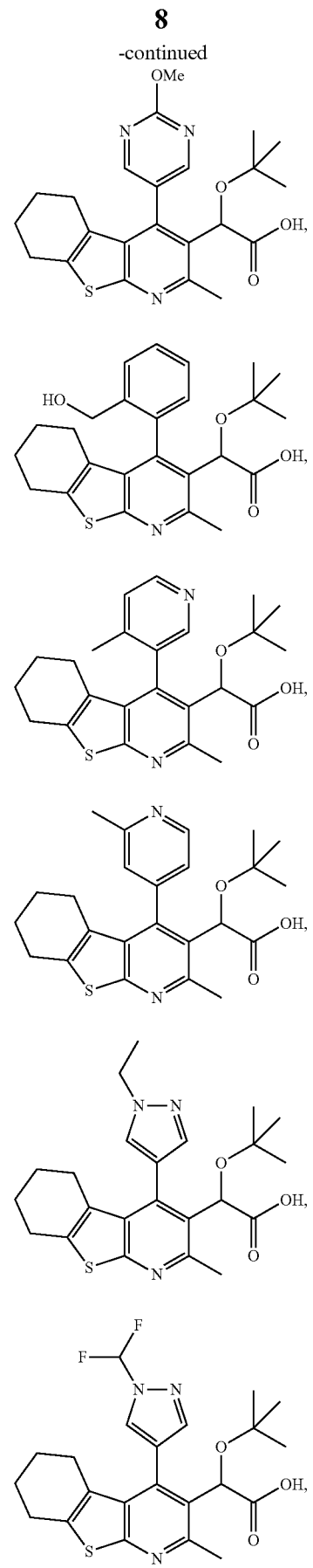

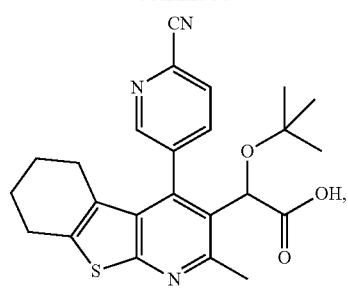
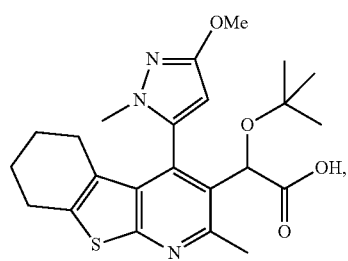
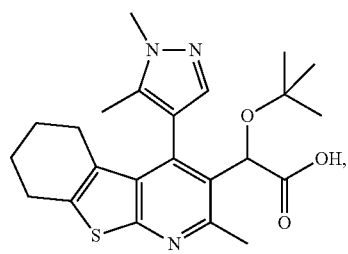
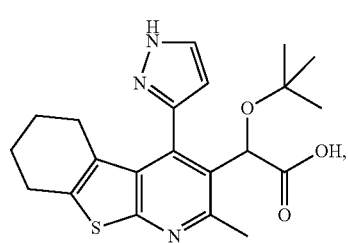
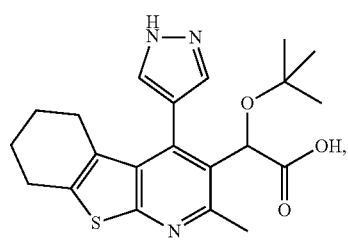
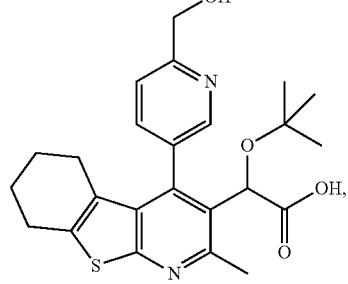
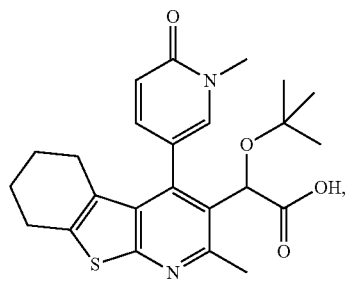
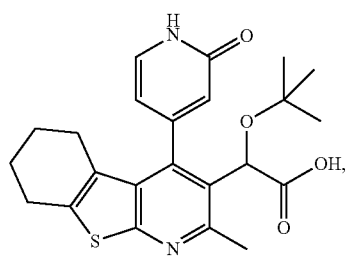
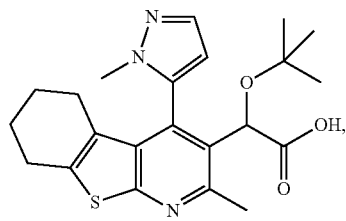
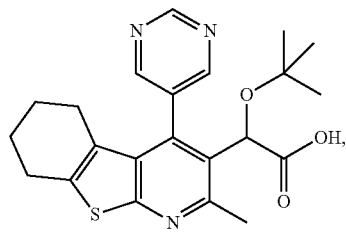
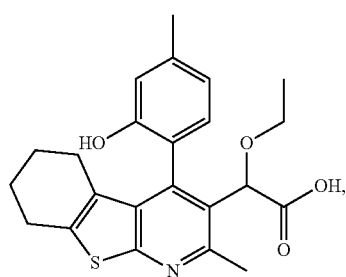
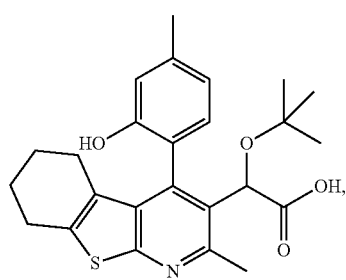

-continued
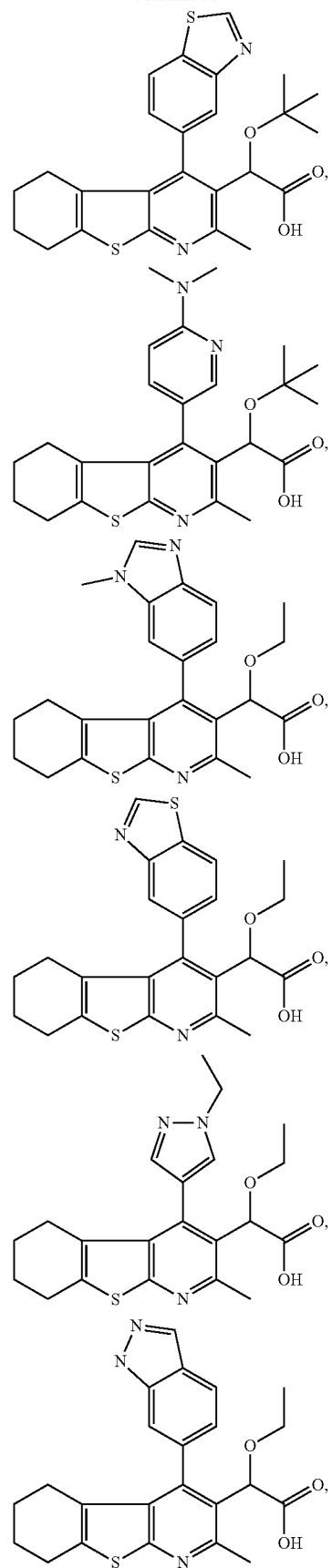
-continued
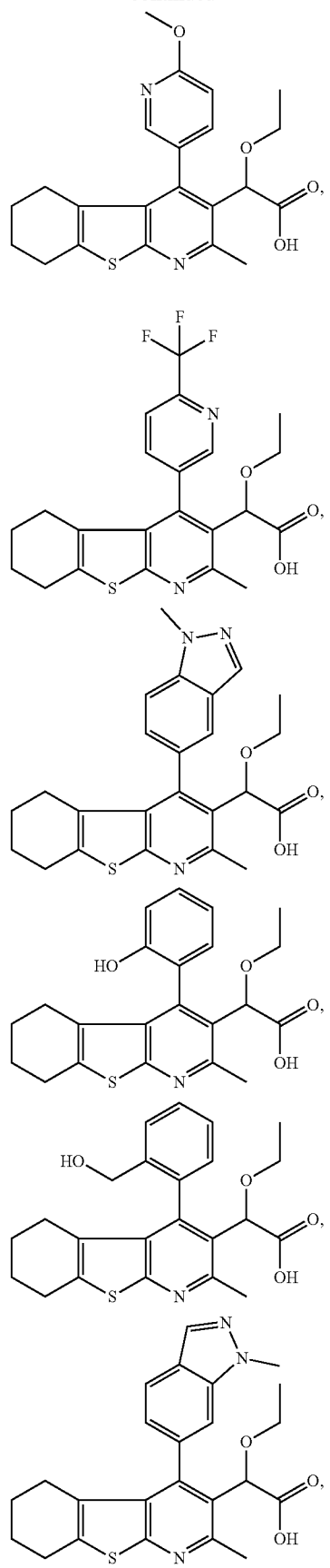

-continued
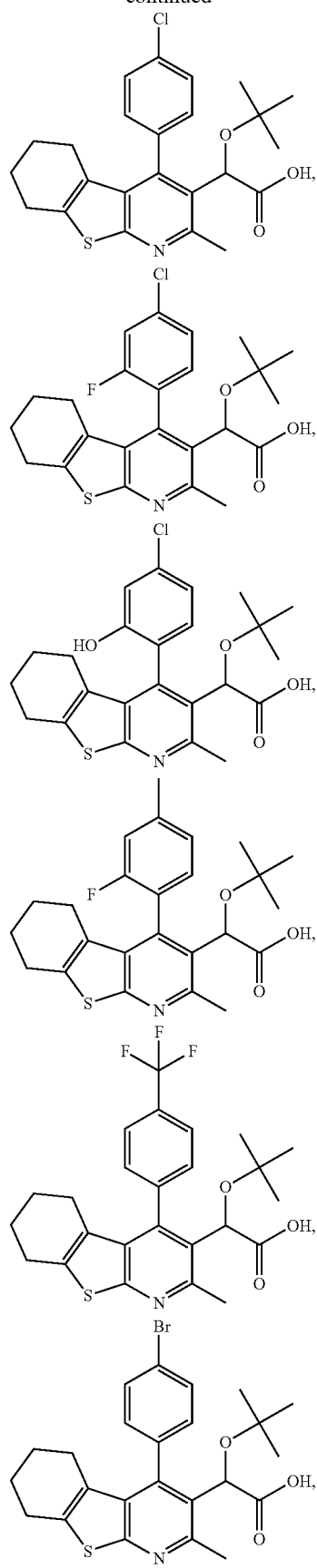
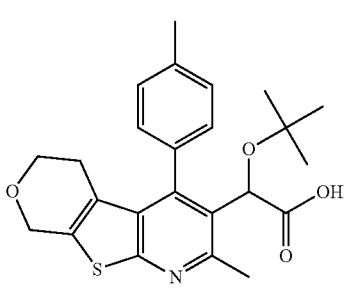
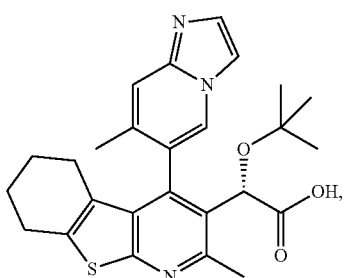
or a pharmaceutically acceptable salt thereof.
In a further embodiment of the first aspect the present invention provides a compound selected from
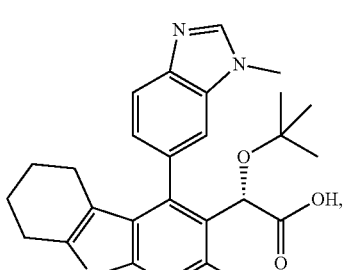
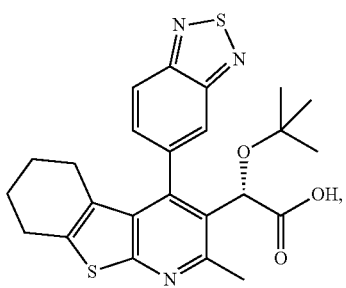

-continued
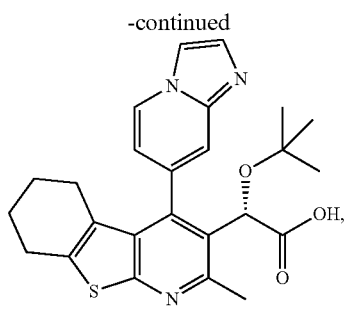
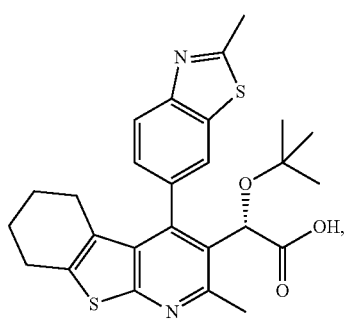
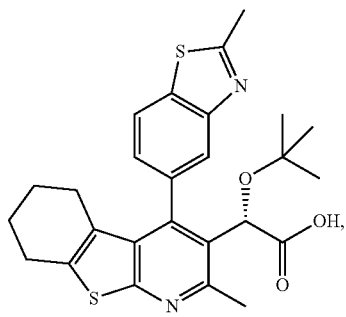
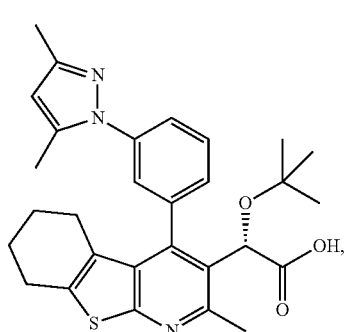
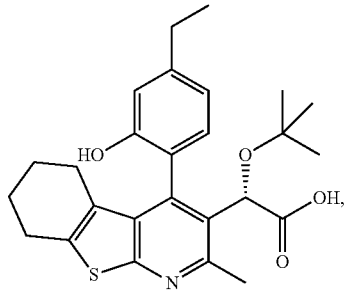
-continued
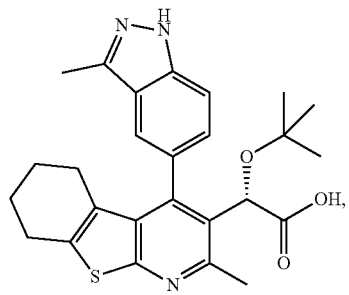
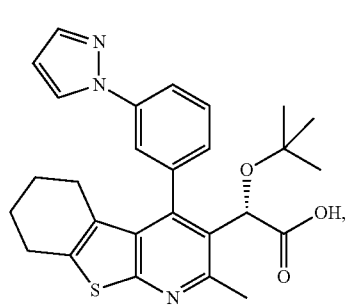
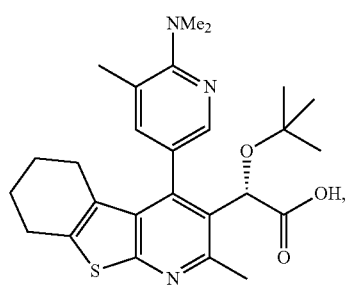
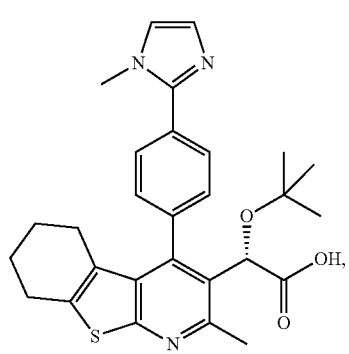
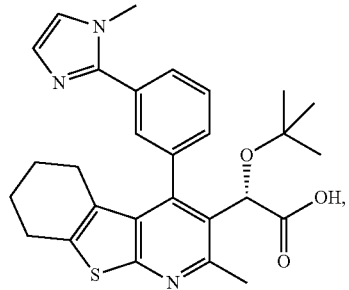

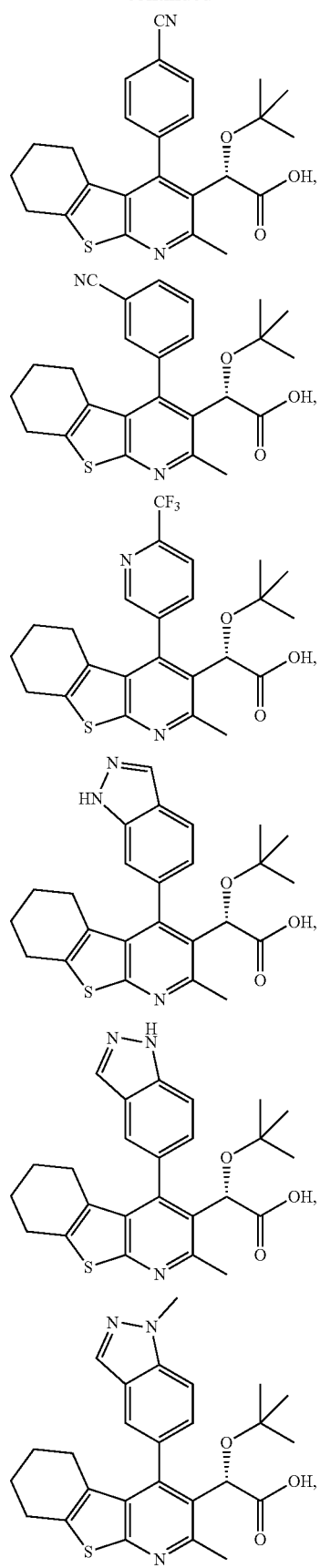
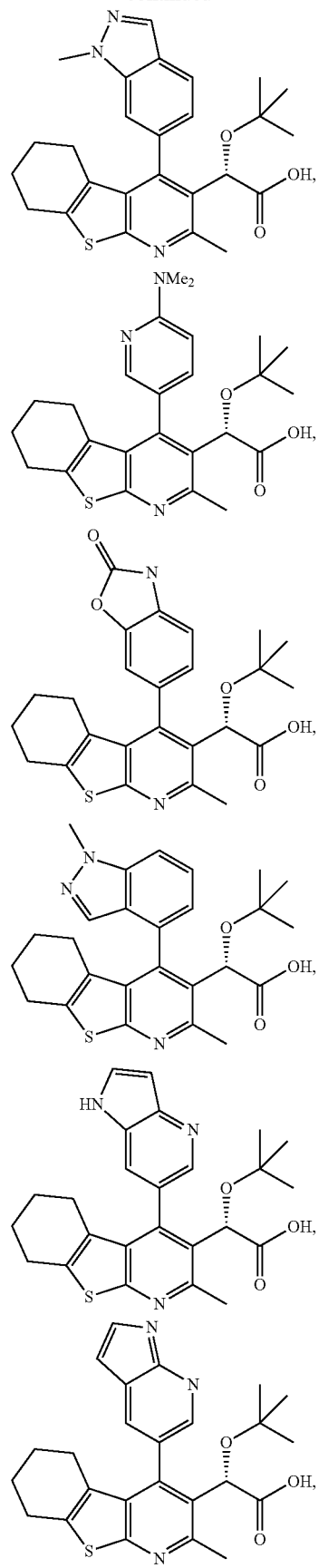

-continued
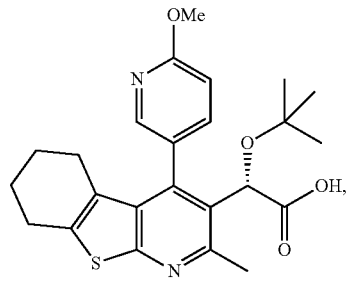
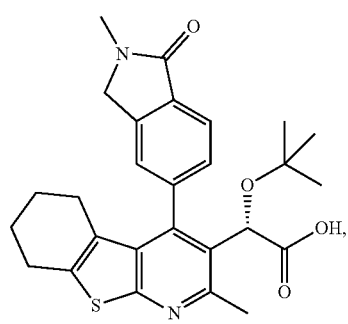
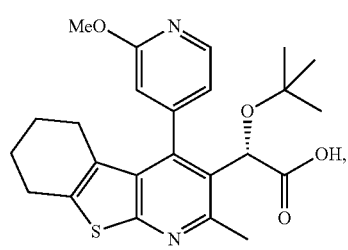
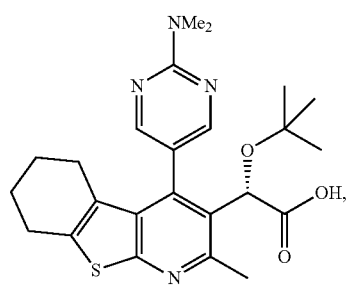
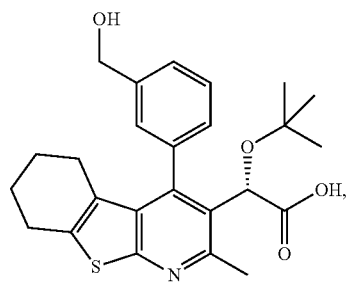
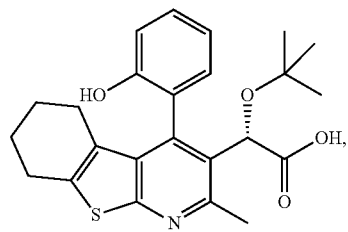
-continued
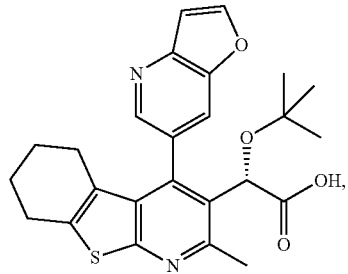
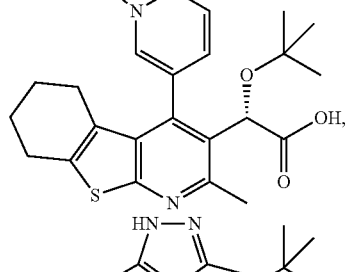
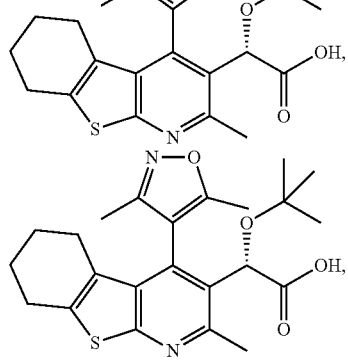
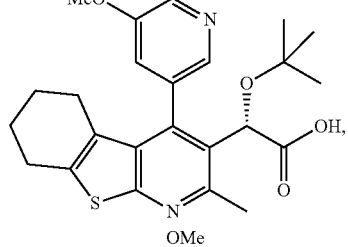
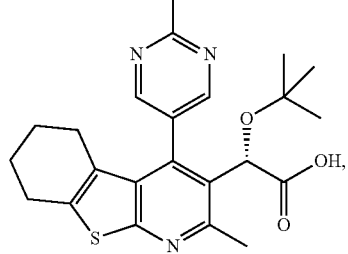
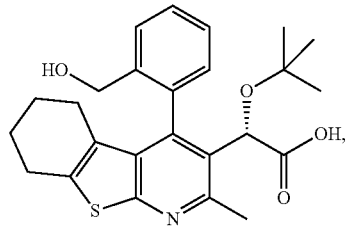

-continued
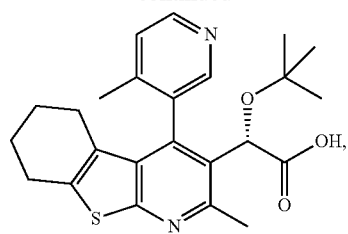
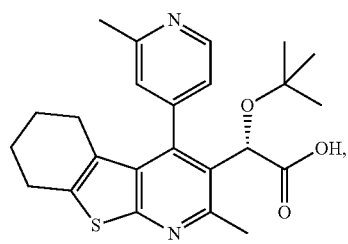
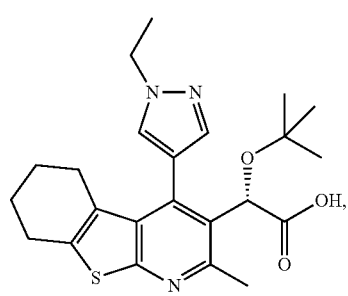
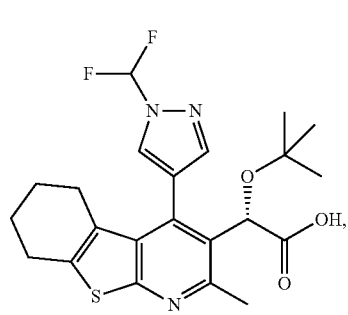
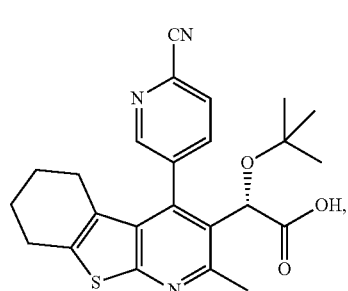
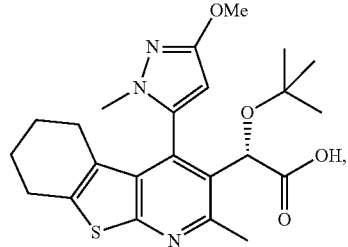
-continued
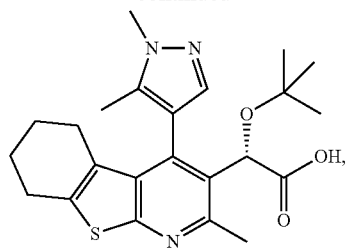
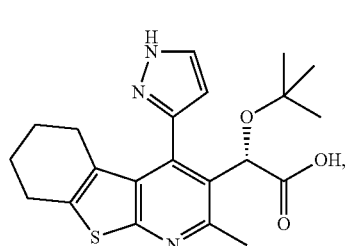
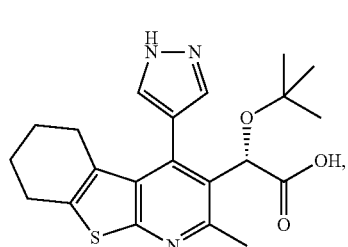
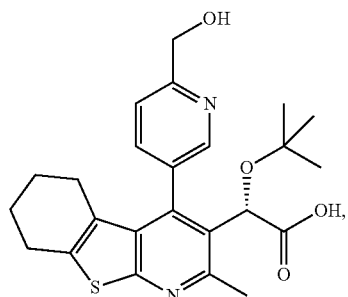
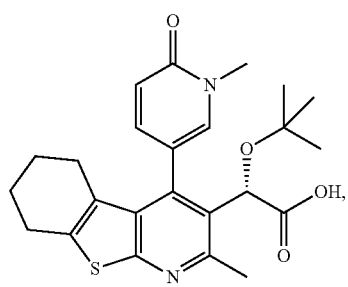
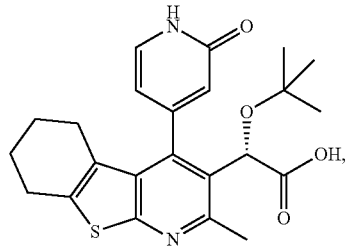

-continued
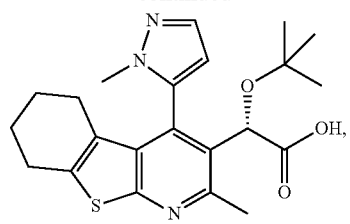
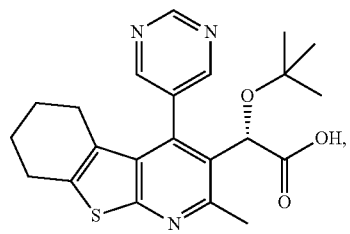
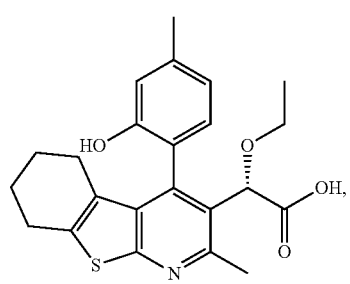
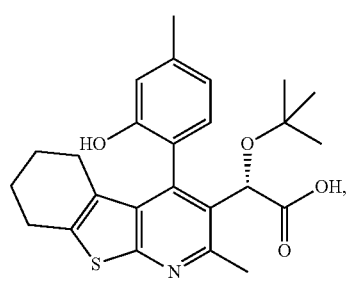
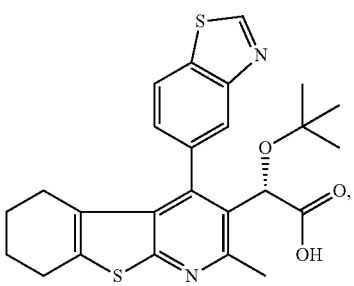
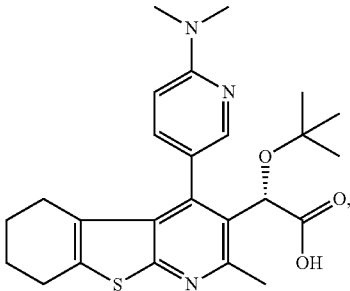
-continued
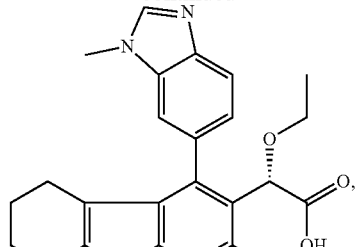
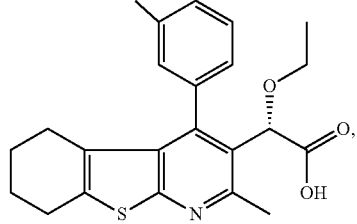
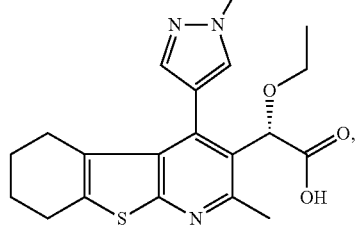
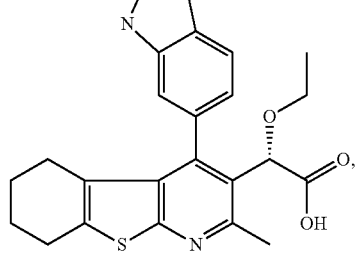
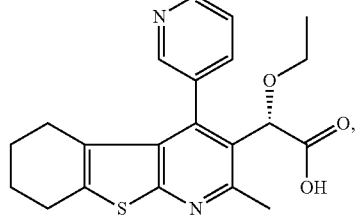
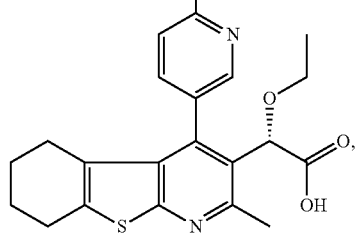

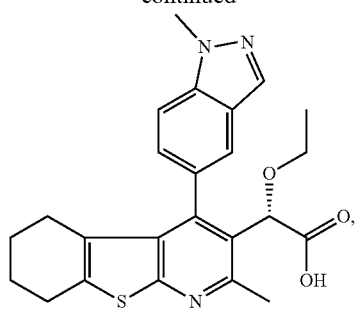
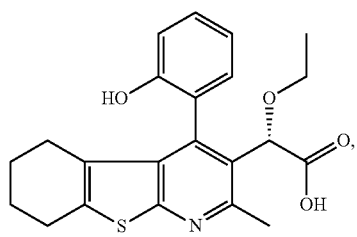
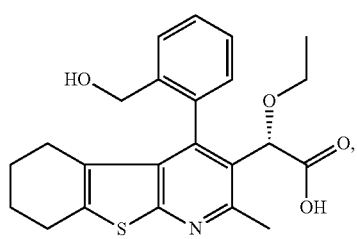
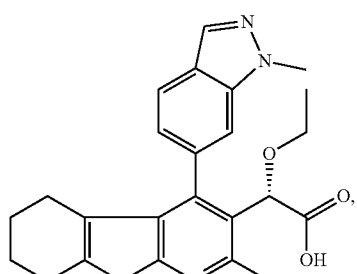
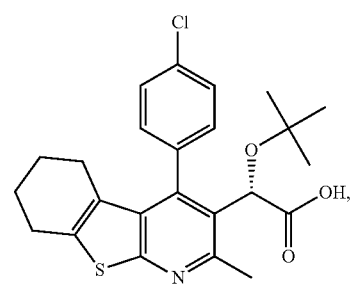
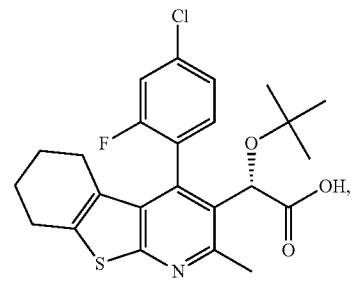
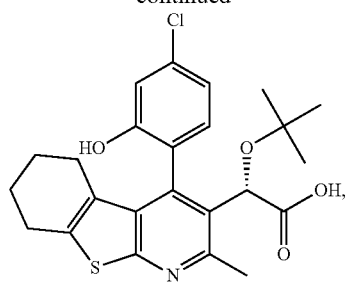
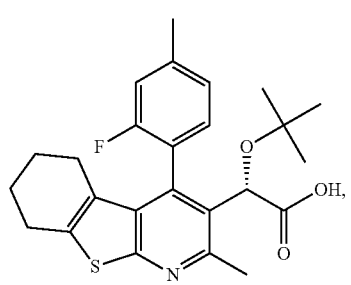
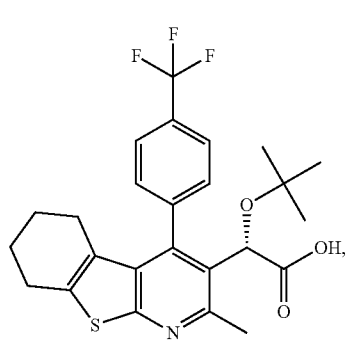
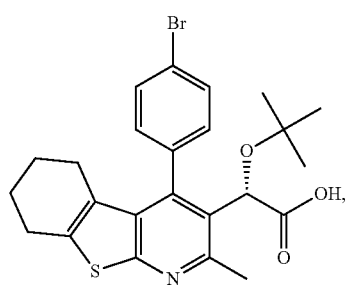
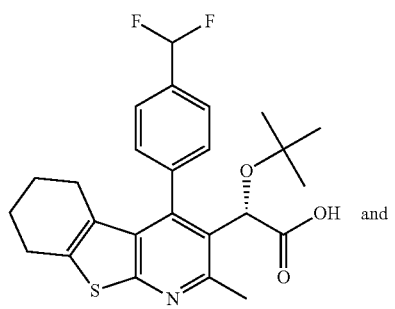

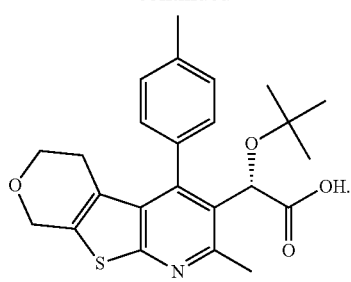

or a pharmaceutically acceptable salt thereof.

In a further embodiment of the first aspect, the present invention provides a compound of formula (I)

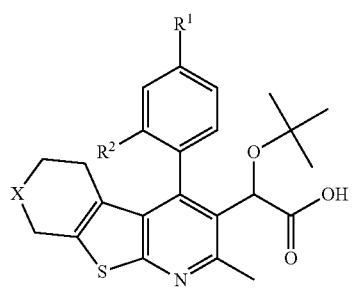
(I)

wherein:
R¹ is CH₃, CH₂CH₃, Cl, Br, CHF₂ or CF₃;
R² is H, OH or F;
X is CH₂ or O;
provided that when R¹ is CH₃ and R² is H, X is O;
or a pharmaceutically acceptable salt thereof.

In a further embodiment of the first aspect, the present invention provides a compound selected from:

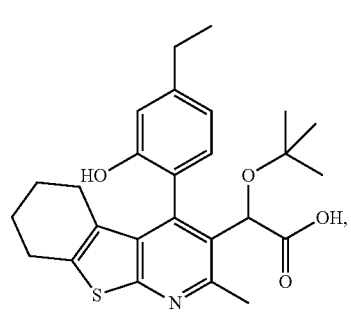

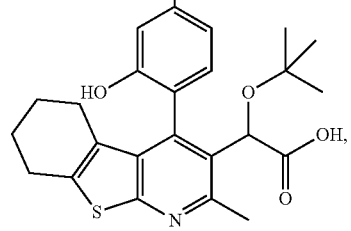

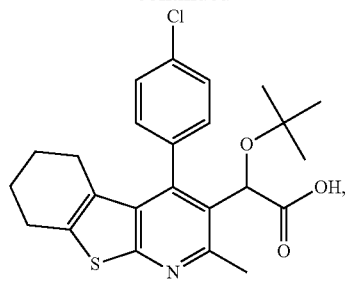

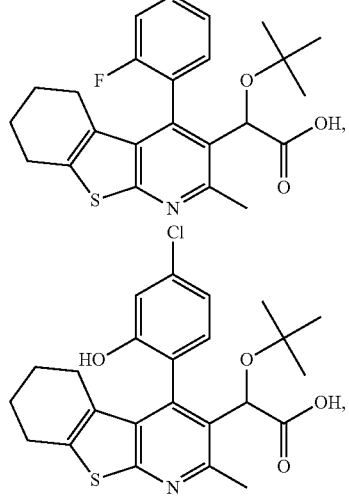

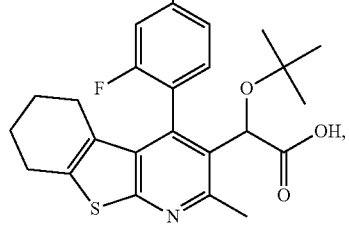

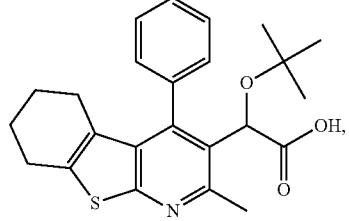

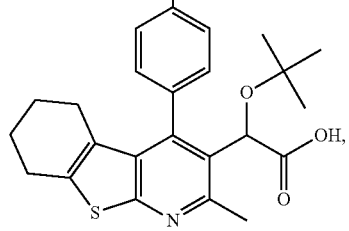

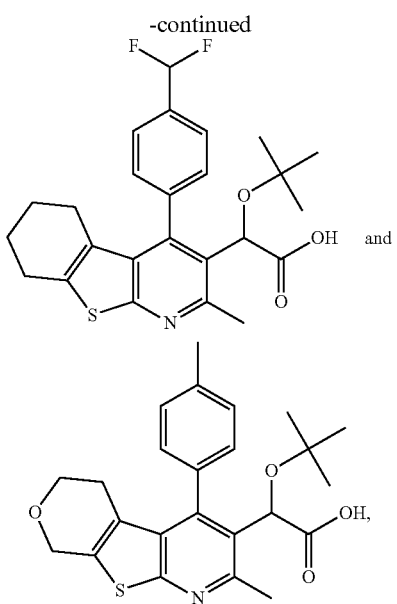

or a pharmaceutically acceptable salt thereof.

In a further embodiment of the first aspect, the present invention provides a compound of formula (Ia)

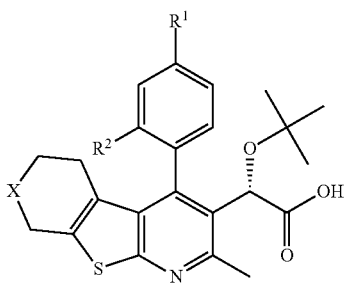
(Ia)

wherein:
R$^1$ is CH$_3$, CH$_2$CH$_3$, Cl, Br, CHF$_2$ or CF$_3$;
R$^2$ is H, OH or F;
X is CH$_2$ or O;
provided that when R$^1$ is CH$_3$ and R$^2$ is H, X is O;
or a pharmaceutically acceptable salt thereof.

In a further embodiment of the first aspect, the present invention provides a compound selected from:

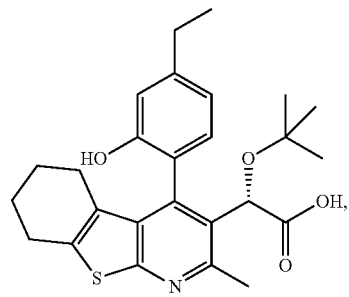

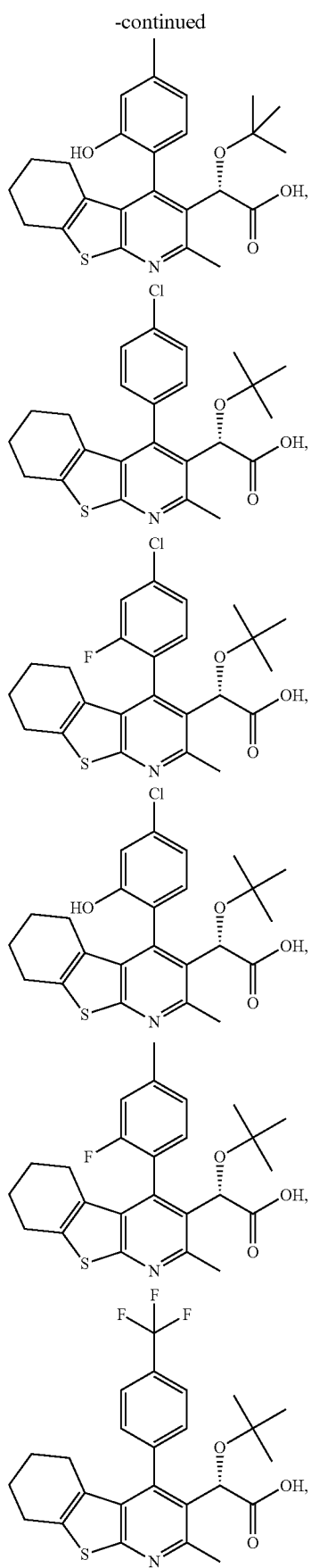

-continued

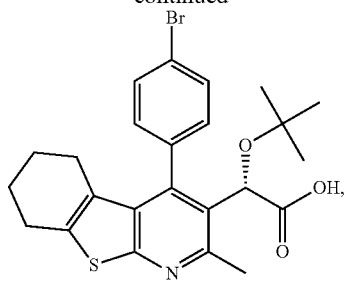

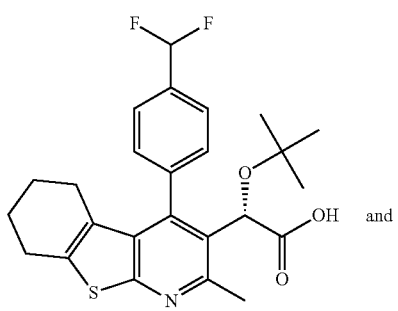

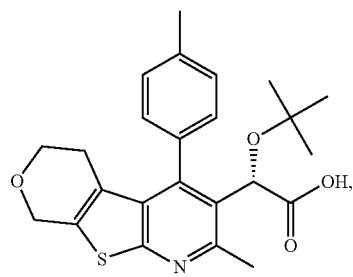

or a pharmaceutically acceptable salt thereof.

In a further embodiment of the first aspect, the present invention provides a compound selected from:

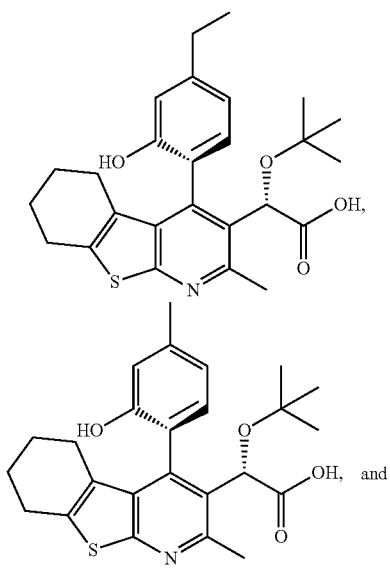

-continued

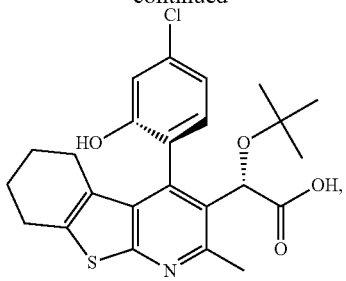

or a pharmaceutically acceptable salt thereof.

Pharmaceutically acceptable salts of the compounds described above include the acid addition and base salts thereof.

Suitable acid addition salts may be formed from acids which form non-toxic salts. Examples may include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts may be formed from bases which form non-toxic salts. Examples may include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, Weinheim, Germany, 2002).

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water. A currently accepted classification system for organic hydrates is one that defines isolated site, channel, or metal-ion coordinated hydrates—see "Polymorphism in Pharmaceutical Solids" by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as $-COO^- Na^+$, $-COO^-K^+$, or $-SO_3^-Na^-$) or non-ionic (such as $-N^-N^+(CH_3)_3$) polar head group. For more information, see "Crystals and the Polarizing Microscope" by N. H. Hartshorne and A. Stuart, $4^{th}$ Edition (Edward Arnold, 1970).

Hereinafter all references to a compound include references to salts, solvates, polymorphs, crystal habits, multi-component complexes and liquid crystals thereof and to solvates, polymorphs, crystal habits, multi-component complexes and liquid crystals of salts thereof.

The compounds of the present invention have a chiral centre adjacent to the carboxyl group. Thus, compounds which do not also exhibit atropisomerism (described in more detail below), may exist as two stereoisomers (i.e. enantiomers). For example:

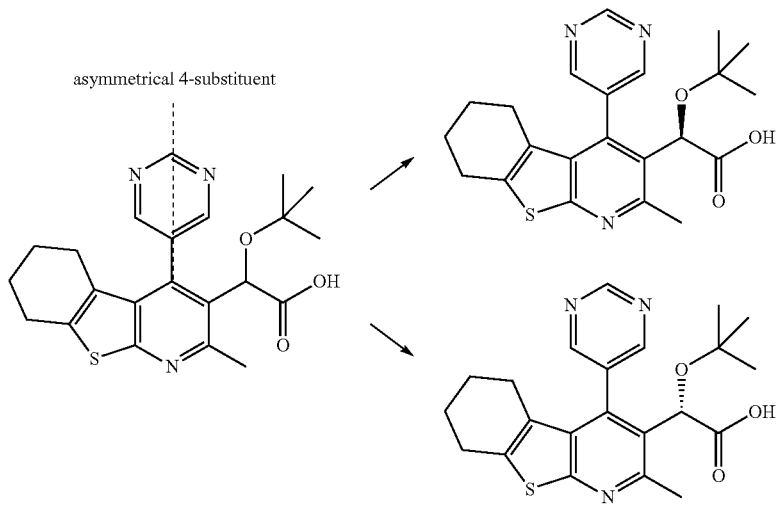 [SMILES: Cc1nc2sc3c(c2c(-c2cncnc2)c1C(OC(C)(C)C)C(=O)O)CCCC3 ; Cc1nc2sc3c(c2c(-c2cncnc2)c1[C@@H](OC(C)(C)C)C(=O)O)CCCC3 ; Cc1nc2sc3c(c2c(-c2cncnc2)c1[C@H](OC(C)(C)C)C(=O)O)CCCC3]

When the 4-substituent is not symmetrical about the plane of the bond at the 4-position, atropisomerism may also arise. This is because the aromatic ring of the 4-substituent and the pyridine portion of the 5,6,7,8-tetrahydro[1]benzothieno[2,3-b]pyridine lie more or less orthogonal to one another and rotation about the bond at the 4-position of the 2,3,4-substituted 5,6,7,8-tetrahydro[1]benzothieno[2,3-b]pyridine compounds of the present invention may be restricted. Such compounds may therefore exist as four stereoisomers (i.e. diastereoisomers). For example:

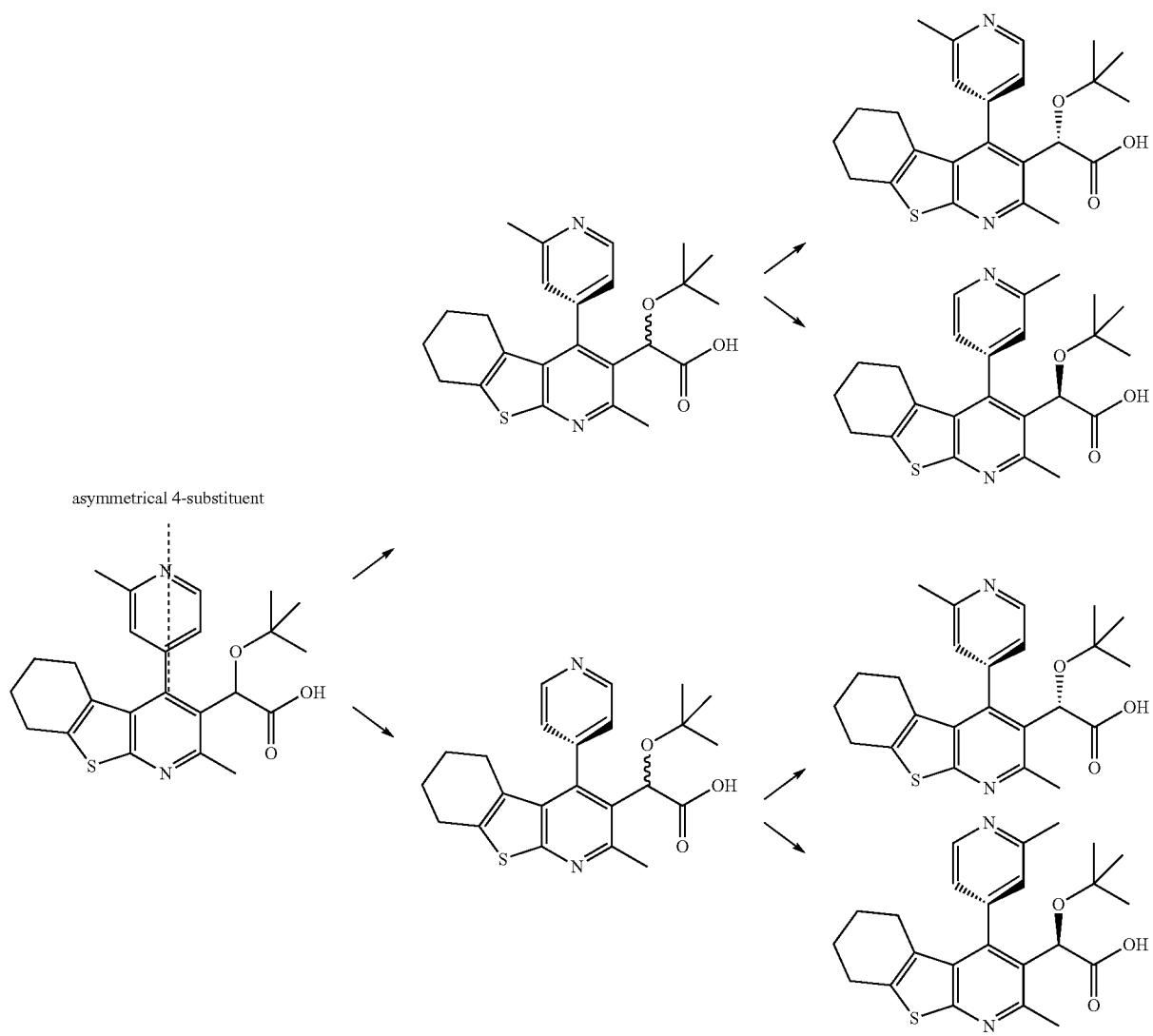

Compounds of formula (I) also contain aromatic moieties, such as the imidazole rings, wherein tautomeric isomerism ('tautomerism') can occur. This can take the form of proton tautomerism (for example in the imidazole rings) as well as valence tautomerism (for example in the other aromatic moieties). It follows that a single compound may exhibit more than one type of isomerism.

Included within the scope of the claimed compounds of the present invention are all stereoisomers and tautomeric forms of the compounds, including compounds exhibiting more than one type of isomerism, and mixtures of one or more thereof.

Where a compound or formula is depicted with a specified stereochemistry at one or more chiral centres, this is intended to specify that the compound or formula has a stereoisomeric excess of at least 80% (i.e. at least 90% of the specified isomer and at most 10% of the other possible isomers), preferably at least 90%, more preferably at least 94% and most preferably at least 99%.

Conventional techniques for the preparation/isolation of individual enantiomers/diastereoisomers include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluant affords the enriched mixture. Alternatively, separation can be carried out using SFC on a resin with an asymmetric stationary phase and with a mobile phase consisting of a gradient of $CO_2$ dissolved in methanol.

Mixtures of stereoisomers may be separated by conventional techniques known to those skilled in the art See, for example, "Stereochemistry of Organic Compounds" by E L Eliel (Wiley, New York, 1994).

The absolute configuration of a single stereoisomer of a compound of the present invention may be determined by solving the crystal structure of a crystalline enzyme-compound complex using techniques known to those skilled in the art.

The compounds of the invention may be synthesised according to the following general methods.

Scheme 1

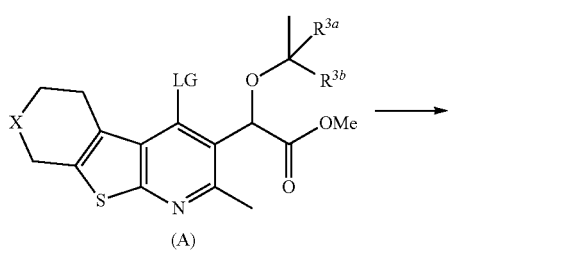

(A)

LG = leaving group (for example a sulfonate or halogen)
$R^{3a}$ and $R^{3b}$ are H or $CH_3$

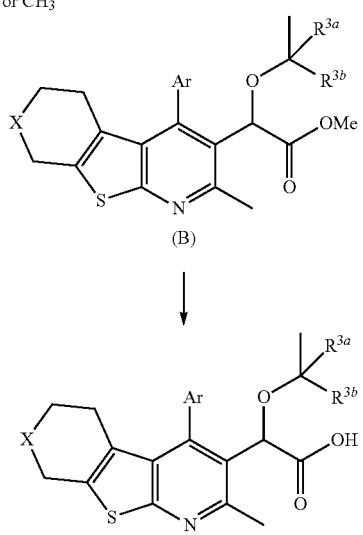

Coupling of a compound of formula (A) with a suitable aryl (Ar) precursor by known procedures (amination, Suzuki coupling, Negishi coupling, Stille coupling and the like) provides compounds of formula (B), which can be converted into the desired compounds of the invention using standard hydrolysis conditions.

Scheme 2

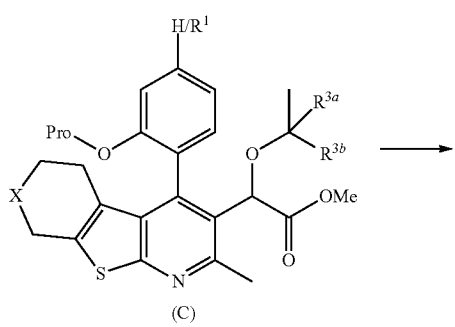

(C)

Pro = protecting group (e.g. allyl)
R3a and R3b are H or $CH_3$

-continued

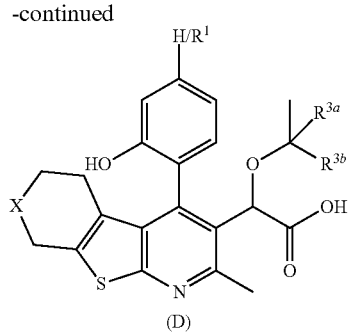

(D)

Compounds of the formula (D) may also be obtained by removal of a phenolic protecting group e.g. allyl, benzyl using standard deprotection conditions, either before or after or at the same time as hydrolysis of the ester group of compounds (C).

In a Second aspect, the present invention provides a pharmaceutical composition including a compound of the present invention or a pharmaceutically acceptable salt or solvate thereof, together with a pharmaceutically acceptable excipient.

The term 'excipient' is used herein to describe any ingredient other than the compound of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include both solid and liquid formulations.

Solid formulations include tablets, capsules (containing particulates, liquids, or powders), lozenges (including liquid-filled lozenges), chews, multi- and nano-particulates, gels, solid solutions, liposomal preparations, films, ovules, and sprays.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form.

In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose.

Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets", Vol. 1, by H. Lieberman and L. Lachman (Marcel Dekker, New York, 1980).

Consumable oral films are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function. The film-forming polymer may be selected from natural polysaccharides, proteins, or synthetic hydrocolloids and s typically present in the range 0.01 to 99 weight %, more typically in the range 30 to 80 weight %. Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents. Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of the compound of the present invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus the compound of the invention may be formulated as a solid, semi-solid, or thixotropic liquid for administration as an implanted depot providing modified release of the active compound. Examples of such formulations include drug-coated stents and poly(di-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, crams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporaton, iontophoresis, phonophoresis, sonophoresis and microneedle or needle-free (e.g. Powderject™, Blojects™, etc.) injection.

Formulations for topical administration may be formulated to be immediate and/or modified release. Modified release formulations include delayed-, sustained-, pulsed-, controlled-, targeted and programmed release.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

In a third aspect, the present invention provides a compound of the present invention or a pharmaceutically acceptable salt thereof, for use as a medicament A specific embodiment of this aspect of the invention is a compound of the present invention or a pharmaceutically acceptable salt thereof, for use in the treatment of HIV infection.

In a fourth aspect, the present invention provides the use of a compound of the present invention or a pharmaceutically acceptable salt thereof, for the manufacture of a medicament for the treatment of HIV infection.

In a fifth aspect, the present invention provides a method of treatment of a mammal, including a human being, to treat HIV infection, including administering to said mammal an effective amount of a compound of the present invention or a pharmaceutically acceptable salt or solvate thereof.

The term 'treatment' as used herein includes both preventative and curative treatment of a disease or disorder. It also includes slowing, interrupting, controlling or stopping the progression of a disease or disorder. It also includes preventing, curing, slowing, interrupting, controlling or stopping the symptoms of a disease or disorder.

The compound of the present invention may be administered in combination with one or more additional agents for the treatment of a mammal, such as a human, that id suffering from an infection with the HIV virus, or any other disease or condition which is related to infection with the HIV virus. The agents that may be used in combination with the compounds of the present invention include, but are not limited to, those useful as HIV protease inhibitors, HIV reverse transcriptase inhibitors, non-nucleoside HIV reverse transcriptase inhibitors, HIV integrase inhibitors, CCR5 inhibitors, HIV fusion inhibitors or other inhibitors of HIV entry, maturation inhibitors, agents that act to perturb HIV capsid multimerisation or viral core stability, compounds targeting host proteins required for viral replication or immune evasion (such as but not limited to PSIP1), compounds useful as immunomodulators, compounds that inhibit the HIV virus by an unknown mechanism, compounds useful for the treatment of herpes viruses, compounds useful as anti-infectives, and others as described below.

Compounds useful as HIV protease inhibitors that may be used in combination with the compound of the present invention include, but are not limited to, 141 W94 (amprenavir), CGP-73547, CGP-61755, DMP-450 (mozenavir), nelfinavir, ritonavir, saquinavir (invirase), lopinavir, TMC-126, atazanavir, palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, TMC-114 (darunavir), DPC-681, DPC-684, fosamprenavir calcium (Lexiva), benzenesulfonamide derivatives disclosed in WO 03053435, R-944, Ro-03-34649, VX-385 (brecanavir), GS-224338, OPT-TL3, PL-100, SM-309515, AG-148, DG-35-VIII, DMP-850, GW-5950X, KNI-1039, L-756423, LB-71262, LP-130, RS-344, SE-063, UIC-94-003, Vb-19038, A-77003, BMS-182193, BMS-188318, SM-309515, JE-2147, GS-9005, telinavir (SC-52151), BILA-2185 BS, DG-17, PPL-100, A-80987, GS-8374, DMP-323, U-103017, CGP-57813, and CGP-53437.

Compounds useful as inhibitors of the HIV reverse transcriptase enzyme that may be used in combination with the compound of the present invention include, but are not limited to, abacavir, emtricitabine (FTC), GS-840 (adefovir), lamivudine, adefovir dipivoxil, beta-fluoro-ddA, zalcitabine, didanosine, stavudine, zidovudine, tenofovir, tenofovir disoproxil fumarate, amdoxovir, SPD-754 (apricitabine), SPD-756, racivir, reverset (DPC-817), MIV-210 (FLG), beta-L-Fd4C (ACH-126443, elvucitabine), MIV-310 (alovudine, FLT), dOTC, DAPD, entecavir, GS-7340, stampidine, D-d4FC (dexelvucitabine), phospahzide, fozivudine tidoxil, and fosalvudine tidoxil.

Compounds useful as non-nucleoside inhibitors of the HIV reverse transcriptase enzyme that may be used in combination with the compound of the present invention include, but are not limited to, efavirenz, HBY-097, nevirapine, dapivirine (TMC-120), TMC-125, etravrine, delavirdine, DPC-083, DPC-961, TMC-120, capravirine, GW-678248, GW-695634, calanolide, rilpivirine (TMC-278), loviride, emivirine (MKC-442), DPC-963, MIV-150, BILR 355 BS, VRX-840773, lersivirine (UK-453061), RDEA806, and tricyclic pyrimidinone derivatives as disclosed in WO 03062238.

Compounds useful as CCR5 inhibitors that may be used in combination with the compound of the present invention include, but are not limited to, TAK-779, SC-351125, SCH-D, UK-427857 (maraviroc), PRO-140, and GW-873140 (aplaviroc, Ono-4128, AK-602), SCH-417690 (viciviroc, SCH-D), INCB-9471, INCB-15050, TBR-220 (TAK-220), CCR5 mAb004. Other compounds useful as CCR5 inhibitors that may be used in combination with the compound of the present invention include, but are not limited to, (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide), methyl 1-endo-{8-[(3S)-3-(acetylamino)-3-(3-fluorophenyl)propyl]-8-azabicyclo [3.2.1]oct-3-yl}-2-methyl-4,5,6,7-tetrahydro-1H-imidazo[4,5-c]pyridine-5-carboxylate, and N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide).

Compounds useful as inhibitors of HIV integrase enzyme that may be used in combination with the compound of the present invention include, but are not limited to, raltegravir, elvitegravir (GS-9137, JTK-303), GSK-364735, MK-2048, BMS-707035, S-1360 (GW-810781), L-870810, L-870812, AR-177, BA-011, 1,5-naphthyridine-3-carboxamide derivatives disclosed in WO 03062204, compounds disclosed in WO 03047564, compounds disclosed in WO 03049690, 5-hydroxypyrimidine-4-carboxamide derivatives disclosed in WO 03035076, and L-000810810.

Fusion inhibitors for the treatment of HIV that may be used in combination with the compound of the present invention include, but are not limited to enfuvirtide (T-20), T-1249, AMD-3100, sifuvirtide, FB-006M, TRI-1144, PRO-2000 and fused tricyclic compounds disclosed in JP 2003171381.

Maturation inhibitors for the treatment of HIV that may be used in combination with the compound of the present invention include, but are not limited to bevirimat and vivecon.

HIV fixed drug combinations for the treatment of HIV that may be used in combination with the compound of the present invention include, but are not limited to, combivir, atripla, trizvir, truvada, kaletra and epzicom.

CXCR4 inhibitors for the treatment of HIV that may be used in combination with the compound of the present invention include, but are not limited to, AMD-070.

Entry inhibitors for the treatment of HIV that may be used in combination with the compound of the present invention include, but are not limited to, SP-01A.

Gp 120 inhibitors for the treatment of HIV that may be used in combination with the compound of the present invention include, but are not limited to, BMS-488043 and BMS-378806.

G6PD and NADH-oxidase inhibitors for the treatment of HIV that may be used in combination with the compound of the present invention include, but are not limited to, immunitin.

Other compounds that are useful inhibitors of HIV that may be used in combination with the compound of the present invention include, but are not limited to, Soluble CD4, PRO-542, ibalizumab (TNX-355), and compounds disclosed in JP 2003119137.

Compounds useful in the treatment or management of infection from viruses other than HIV that may be used in combination with the compound of the present invention include, but are not limited to, acyclovir, fomivirsen, penciclovir, HPMPC, oxetanocin G, AL-721, cidofovir, cytomegalovirus immune globin, cytovene, fomivganciciovir, famcidovir, foscamet sodium, Isis 2922, KNI-272, valacyclovir, virazole ribavirin, valgancidclovir, ME-609, PCL-016, DES6, ODN-93, ODN-112, VGV-1, ampligen, HRG-214, cytolin, VGX-410, KD-247, AMZ-0026, CYT-99007A-221, DEBIO-025, BAY 50-4798, MDX-010 (ipilimumab), PBS-119, ALG-889, PA-1050040 (PA-040) and flibuvir (PF-00868554).

Compounds that act as immunomodulators and may be used in combination with the compound of the present invention include, but are not limited to, AD-439, AD-519, Alpha interferon, AS-101, bropirimine, acemannan, CL246, 738, EL10, FP-21399, gamma interferon, granulocyte macrophage colony stimulating factor, IL-2, immune globulin intravenous, IMREG-1, IMREG-2, imuthiol diethyl dithio carbamate, alpha-2 interferon, methionine-enkephalin, MTP-PE, granulocyte colony stimulating sector, remune, rCD4, recombinant soluble human CD4, interferon alfa-2, SK&F106528, soluble T4 yhymopentin, tumor necrosis factor (TNF), tucaresol, recombinant human interferon beta, and interferon alfa n-3.

Anti-infectives that may be used in combination with the compound of the present invention include, but are not limited to, atovaquone, azithromycin, clarithromycin, trimethoprim, trovafloxacin, pyrimethamine, daunorubicin, clindamycin with primaquine, pastill, omidyl, eflothine pentamidine, rifabutin, spiramycin, intraconazole-R51211, trimeterxate, daunorubicin, chloroquine, recombinant human erythropoletin, recombinant human growth hormone, megestrol acetate, testerone, and total enteral nutrition.

Antifungals that may be used in combination with the compound of the present invention include, but are not limited to, anidulafungin, C31G, caspofungin, DB-289, fluconazole, itraconazole, ketoconazole, micafungin, posaconazole, and voriconazole.

Other compounds that may be used in combination with the compound of the present invention include, but are not limited to, acemannan, ansamycin, LM 427, AR177, BMS-232623, BMS-234475, CI-1012, curdlan sulfate, dextran sulfate, STOCRINE EL10, hypericin, lobucavir, novapren, peptide T octabpeptlde sequence, trisodium phosphonoformate, probucol, and RBC-CD4.

In addition, the compound of the present invention may be used in combination with anti-proliferative agents for the treatment of conditions such as Kaposi's sarcoma. Such agents include, but are not limited to, inhibitors of metallomatrix proteases, A-007, bevacizumab, BMS-275291, halofuginone, interleukin-12, rituximab, paclitaxel, porfimer sodium, rebimastat, and COL-3.

Such a combination may be administered such that the compound of the present invention is present in the same pharmaceutical composition as the additional agent(s) described above. Alternatively, such a combination may be administered such that the compound of the present invention is present in a pharmaceutical composition that is separate from the pharmaceutical composition in which the additional agent(s) is(are) found. If the compound of the present invention is administered separately from the additional agent(s), such administration may take place concomitantly or sequentially with an appropriate period of time in between.

Additionally, the compound of the present invention may be administered in combination with one or more additional agents that have the effect of increasing the exposure of the mammal to the compound of the invention. The term 'exposure', as used herein, refers to the concentration of the compound of the invention in the plasma of a mammal as measured over a period of time. The exposure of a mammal to a particular compound can be measured by administering the compound of the invention to a mammal in an appropriate form, withdrawing plasma samples at predetermined times, and measuring the amount of a compound of the invention in the plasma using an appropriate analytical technique, such as liquid chromatography or liquid chromatography/mass spectroscopy. The amount of the compound of the invention present in the plasma at a certain time is determined and the concentration and time data from all the samples are plotted to afford a curve. The area under this curve is calculated and affords the exposure of the mammal to the compound. The terms 'exposure', 'area under the curve', and 'area under the concentration/time curve' are intended to have the same meaning and may be used interchangeably.

Among the agents that may be used to increase the exposure of a mammal to a compound of the present invention are those that can act as inhibitors of at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. Suitable agents that may be used to inhibit CYP3A4 include, but are not limited to, ritonavir, delavirdine, N-(3,4-difluorobenzyl)-2-{[(4-methoxypyridin-3-yl)amino]sulfonyl}-N-methylbenzamide, and N-(1-(5-(4-fluorobenzyl)-3-(pyridin-4-yl)-1H-pyrazole-1-carbonyl)piperidin-4-yl)methanesulfonamide.

Such a combination may be administered such that the compound of the present invention is present in the same formulation as the additional agent(s) described above. Alternatively, such a combination may be administered such that the compound of the present invention is present in a pharmaceutical composition that is separate from the pharmaceutical composition in which the additional agent(s) is(are) found. If the compound of the present invention is administered separately from the additional agent(s), such administration may take place concomitantly or sequentially with an appropriate period of time in between.

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for co-administration of the compositions.

Thus the kit of the invention comprises two or more separate pharmaceutical compositions, at least one of which contains a compound of the present invention in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

The following procedures illustrate methods suitable for the preparation of compounds of the present invention.

General Methods

LCMS (2 min acidic) A: 0.1% formic acid in water, B: 0.1% formic acid in acetonitrile, Column: Agilent Extend C18 phase 30×3 mm with 3 micron particle size, Gradient 90-0% A over 1.8 min, 0.55 min hold, 0.15 min re-equilibration, 1.6 mL/min flow rate, UV: 210 nm-450 nm DAD, Temperature: 50° C.

LCMS (5 min acidic) A: 0.1% formic acid in water B: 0.1% formic acid in acetonitrile Column: Agilent Extend C18 phase 50×3 mm with 3 micron particle size Gradient 95-0% A over 3.5 min, 1 min hold, 0.4 min re-equilibration, 1.2 mL/min flow rate UV: 210 nm-450 nm DAD Temperature: 50° C.

LCMS (12 min acidic) A: 0.1% formic acid in water B: 0.1% formic acid in acetonitrile Column: Agilent SB C18 phase 50×3 mm with 3 micron particle size Gradient 95% A 1 min hold, 95-0% A over 8 min, 2.5 min hold, 0.50 min re-equilibration, 1.2 mL/min flow rate UV: 210 nm-450 nm DAD Temperature: 50° C. LCMS (5 min basic) A: methanol, B: 10 mM ammonium bicarbonate in water @ pH10, Column: XBridge C18 2.1×30 mm with 5 micron particle size, Gradient: 95-5% A over 2.9 min, 0.9 min hold, 0.1 min re-equilibration, 0.5 mL/min flow rate UV: 215-350 nm DAD Temperature 25° C.

H NMR Collected on Varian Gemini 400 MHz at 30 C.

Preparation 1: Ethyl 2-amino-4,5,6,7-tetrahydro-1-benzothiophene-3-carboxylate

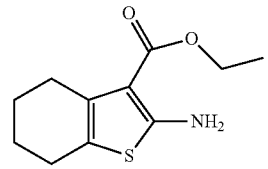

To a solution of ethyl cyanoacetate (427 mL, 4 mol) in ethanol (4 L) was added sulfur (153.88 g, 4.80 mol), morpholine (422 mL, 4.80 mol) and cyclohexanone (497 mL, 4.80 mol) and the resulting solution was stirred at 50° C. for 18 hours. The reaction was cooled to room temperature and filtered to remove solids. The filter cake was washed with cold ethanol and then dried to give the title compound as a pale yellow solid, 608.4 g. The mother liquors were cooled in an ice bath and the resulting precipitate was collected by filtration. The solid was purified by dry flash chromatography eluting with ethyl acetate in heptane (20-30%) to yield a further 38.62 g of the title compound. The two solids were combined to give 647.02 g of the title compound in a 72% yield. $^1$H NMR (400 MHz, CDCl$_3$) δ ppm 1.34 (t, 3 H), 1.73-1.75 (m, 4 H), 2.46-2.49 (m, 2 H), 2.63-2.69 (m, 2 H), 4.25 (q, 2 H), 5.92 (br s, 2 H).

Preparation 2: Ethyl-3-ethoxybut-2-eneoate

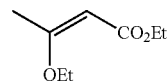

To a solution of ethylacetoacetate (2.7 kg, 20.74 mol) in ethanol (4 L) was added conc. H$_2$SO$_4$ (4 ml) at 25° C. under a nitrogen atmosphere. The mixture was heated to 50° C. before adding triethylorthoformate (3073.6 g, 20.74 mol) drop wise. The mixture was stirred at 50° C. for 16 h. The mixture was concentrated under reduced pressure to give the title compound (2.8 kg, 85%) as a yellow oil. $^1$H NMR (400 MHz, CDCl$_3$): δ 4.9 (s, 1H), 4.1 (m, 2H), 3.7 (m, 2H), 2.2 (s, 3H), 1.2 (m, 3H), 1.1 (m, 3H).

Preparation 3: Ethyl (4-hydroxy-2-methyl-5,6,8-tetrahydro[1]benzothieno[2,3-b]pyridine-3-yl)carboxylate

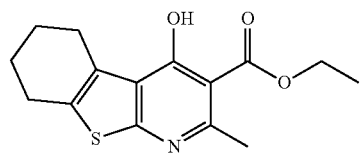 [SMILES: CCOC(=O)c1c(C)nc2sc3c(c2c1O)CCCC3]

In a 10 L reaction vessel, pyridinium p-toluenesulfonic acid (39.7 g, 158 mMol) was added to a stirred solution of ethyl-2-amino-4,5,6,7-tetrahydrobenzo[b]thiophene-3-carboxylate (Preparation 1) and ethyl-3-ethoxybut-2-eneoate (Preparation 2) in toluene (6.0 L) at room temperature under argon. The resulting mixture was heated to reflux, and stirred at reflux for 6 hours. The mixture was cooled 40° C. and stirred at 40° C. for 16 hours. The mixture was heated to 50° C. (to dissolve the precipitate) and the solution was run out of the reaction vessel. The reaction vessel was charged with 21% (w/w) sodium ethoxide in ethanol (1.1 L, 3.48 Mol) and ethanol (2.0 L), and the resulting mixture was heated to 50° C. The reaction mixture was then poured back into the reaction vessel over 5 minutes. The resulting mixture was heated to reflux and stirred at reflux for 2 hours. The mixture was cooled to 30° C. and split into 2 approximately equal batches. Each batch was treated with Celite® (approx. 2 L) and concentrated under reduced pressure. The resulting solids were suspended in water (2.0 L, 40° C.) and stirred vigorously until all solids were free flowing. The solids were collected by filtration through a pad of Celite®, and the filter-cake was washed with water (2.5 L, 40° C.). The filtrate was washed with diethylether (2×1.3 L) and then cooled to 15° C. 6 M hydrochloric acid was added carefully until pH 4 was achieved. The resulting precipitate was collected by filtration and the filter-cake was washed with dilute hydrochloric acid (500 mL). The filter-cake was dried in a drying oven, at 50° C. for 2 days. This gave the title compound as a yellow solid (584 g, 64%).

Preparation 4: Ethyl 4-chloro-2-methyl-5,6,7,8-tetrahydro[1]benzothieno[2,3-b]pyridine-3-carboxylate

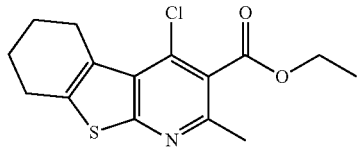 [SMILES: CCOC(=O)c1c(C)nc2sc3c(c2c1Cl)CCCC3]

Ethyl 4-hydroxy-2-methyl-5,6,7,8-tetrahydro[1]benzothieno[2,3-b]pyridine-3-carboxylate (Preparation 3, 150 g, 515 mmol) was added portionwise to phosphorus oxychloride (450 mL, 4.92 mol) and the resulting mixture stirred at 100° C. for 1 hour and then cooled to room temperature. The volatiles were removed in vacuo, and the residue was carefully poured into a vigorously stirred ice/water mixture. Ethyl acetate (500 mL) was added to the mixture. The mixture was adjusted to pH 8, by addition of 10M aqueous sodium hydroxide solution. The layers were separated and the aqueous layer was further extracted with ethyl acetate (3×500 mL). The combined organic extracts were washed with brine (300 mL), dried over MgSO$_4$ and concentrated in vacuo. The resulting oil was poured into a crystallisation dish, where it solidified on standing to give the title compound, 140.69 g, in an 88% yield. $^1$H NMR (400 MHz, CDCl$_3$) δ ppm 1.42 (t, 3 H), 1.86-1.89 (m, 4 H), 2.59 (s, 3 H), 2.82-2.84 (m, 2 H), 3.08-3.11 (m, 2 H), 4.46 (q, 2 H).

Preparation 5: Ethyl (4-iodo-2-methyl-5,6,7,8-tetrahydro[1]benzothieno[2,3-b]pyridine-3-carboxylate

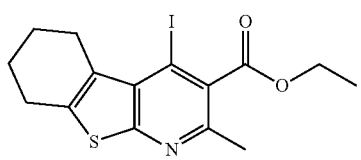 [SMILES: CCOC(=O)c1c(C)nc2sc3c(c2c1I)CCCC3]

Sodium iodide (994.0 g, 6.63 Mol) was added over 5 minutes to a stirred solution of acetyl chloride (177 mL, 2.48 Mol) and ethyl (4-chloro-2-methyl-5,6,7,8-tetrahydro[1]benzothieno[2,3-b]pyridine-3-yl)carboxylate (Preparation 4, 257 g, 0.83 Mol) in acetonitrile (2.0 L) at room temperature. The resulting mixture was heated to reflux and stirred for 30 hours. The mixture was allowed to cool to room temperature and stood for 72 hours. The solids were collected by filtration and washed with cold acetonitrile (500 mL). The solids were partitioned between dichloromethane (1.5 L) and water (0.75 L). The aqueous layer was basified to pH 9 by addition of 2 M sodium hydroxide solution and the two layers were separated. The organic layer was washed with 2 M sodium thiosulphate solution (800 mL), brine (800 mL), dried (Na$_2$SO$_4$), filtered and concentrated under reduced pressure to give the title compound (260.0 g, 78%) as a beige solid. This material was determined by $^1$H NMR spectroscopy to be a 13:1 mixture of ethyl (4-iodo-2-methyl-5,6,7,8-tetrahydro[1]benzothieno[2,3-b]pyridine-3-yl)carboxylate and ethyl (4-chloro-2-methyl-5,6,7,8-tetrahydro[1]benzothieno[2,3-b]pyridine-3-yl)carboxylate respectively.

Preparation 6: (4-iodo-2-methyl-5,6,7,8-tetrahydro[1]benzothieno[2,3-b]pyridine-3-yl)methanol

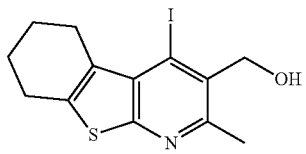 [SMILES: Cc1nc2sc3c(c2c(I)c1CO)CCCC3]

To a solution of ethyl (4-iodo-2-methyl-5,6,7,8-tetrahydro[1]benzothieno[2,3-b]pyridine-3-yl)carboxylate (Preparation 5, 260.2 g, 0.65 Mol) in CH$_2$Cl$_2$ (2.0 L) was added 25% (w/w) diisobutyl aluminium hydride (2.0 L, 1.97 Mol) at 5° C. over 1.5 hours under argon. The resulting mixture was allowed to warm to room temperature and stirred for 16 hours. The resulting mixture was diluted with dichloromethane (1.0 L), cooled to 0° C. and 2 M hydrochloric acid (200 mL) was added very carefully. 6M hydrochloric acid was then added until the pH of the aqueous was measured at pH 2. The resulting mixture was stirred vigorously for 1 hour. The precipitate was collected by filtration and the filter-cake was washed with dichloromethane (300 mL) and water (300 mL). The solids were suspended in dichloromethane (250 mL) and 1 M sodium hydroxide solution (400 mL) and stirred vigorously until the solids were free flowing. The solids were collected by filtration, washing the filter-cake with water (200 mL). The filter-cake was concentrated from propan-2-ol (500 mL), methanol (500 mL) and dichloromethane (500 mL) sequentially under reduced pressure to give the title compound as a cream coloured solid (212.3 g, 91%).

Preparation 7: (4-iodo-2-methyl-5,6,7,8-tetrahydro[1]benzothieno[2,3-b]pyridine-3-yl)carbaldehyde

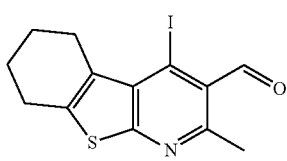 [SMILES: Cc1nc2sc3c(c2c(I)c1C=O)CCCC3]

To a suspension of (4-iodo-2-methyl-5,6,7,8-tetrahydro[1]benzothieno[2,3-b]pyridine-3-yl)methanol (Preparation 6, 150.0 g, 0.42 Mol) in triethylamine (174 mL, 1.25 Mol) and dimethylsulfoxide (1.1 L) was added sulfur trioxide pyridine complex, portion-wise at 5° C. The resulting mixture was stirred at room temperature for 16 hours. The mixture was poured into vigorously stirring ice water (1.0 L). The solids were collected by filtration and the filter-cake washed with water (750 mL). The resulting solids were dissolved in dichloromethane/ethyl acetate (2.0 L, 9:1) (required warming) and the solution was dried (MgSO$_4$), filtered and concentrated under reduced pressure to give the title compound as a white solid (135.0 g, 91%). $^1$H NMR (400 MHz, CDCl$_3$) δ 10.36 (s, 1H), 3.32-3.20 (m, 2H), 2.89-2.79 (m, 2H), 2.76 (s, 3H) 1.95-1.83 (m, 4H).

Preparation 8: 2-(4-iodo-2-methyl-5,6,7,8-tetrahydro[1]benzothieno[2,3-b]pyridin-3-yl)-2-[(trimethylsilyl)oxy]acetonitrile

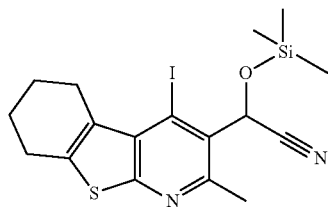 [SMILES: Cc1nc2sc3c(c2c(I)c1C(C#N)O[Si](C)(C)C)CCCC3]

To a suspension of 4-iodo-2-methyl-5,6,7,8-tetrahydro[1]benzothieno[2,3-b]pyridine-3-carbaldehyde (Preparation 7, 115.31 g, 322.8 mmol) in dichloromethane (1.75 L) was added zinc iodide (41.1 g, 128.8 mmol) and the resulting mixture was cooled to 5° C. Trimethylsilyl cyanide (129 mL, 968.4 mmol) was added dropwise over 10 minutes, and the mixture was allowed to warm to room temperature over 2 hours. Water (750 mL) and dichloromethane (1 L) were added and after stirring for 1 hour, the layers were separated. The aqueous layer was extracted with dichloromethane (500 mL) and the combined organic layers were washed with water (700 mL) and brine (700 mL), dried over Na$_2$SO$_4$ and concentrated in vacuo to give the title compound, 145.61 g, in a 99% yield. $^1$H NMR (400 MHz, CDCl$_3$) δ ppm 0.22 (s, 9 H), 1.82-1.93 (m, 4 H), 2.56-2.86 (m, 2 H), 2.92 (s, 3 H), 3.18-3.25 (m, 2 H), 6.48 (s, 1 H).

Preparation 9: Methyl-2-[3-iodo-2-methyl-5,6,7,8-tetrahydro[1]benzothieno[2,3-b]pyridine-3-yl]-2-hydroxyacetate

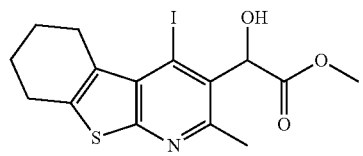 [SMILES: COC(=O)C(O)c1c(C)nc2sc3c(c2c1I)CCCC3]

To a stirred suspension of 2-(4-iodo-2-methyl-5,6,7,8-tetrahydro[1]benzothieno[2,3-b]pyridine-3-yl)-2-trimethylsiloxyacetonitrile (Preparation 8, 168.0 g, 369.10 mMol) in methanol (2.5 L) was added concentrated sulphuric acid (410 mL, 7.38 Mol) at 5° C. The mixture was heated to 70° C. and stirred for 36 hours. After allowing the mixture to cool to room temperature, the mixture was diluted with water (1.0 L) and ethyl acetate (2.0 L), and then cooled to 5° C. The pH of the aqueous layer was adjusted to pH 8 by careful addition of 6 M aqueous sodium hydroxide solution. This resulted in the precipitation of solids. The solids were collected by filtration, and the filter-cake Was washed with warm water (500 mL) and ethyl acetate (200 mL). The filtrate was saved for further manipulation. The filter-cake was suspended in methanol (500 mL) and stirred vigorously until the solid was free flowing. The solids were collected by filtration and the filter-cake was washed with methanol (2×200 mL) and diethylether (2×200 mL). The resulting solid was dried at 50° C. for 16 hours. This gave the title compound (66.5 g, 43%) as a white solid. The layers of the saved filtrates were separated and the organic layer was concentrated under reduced pressure. The resulting residue was triturated with methanol (100 mL), ethyl acetate (100 mL) and diethylether (100 mL). The resulting solid was collected by filtration and dried at 50° C. for 16 hours. This gave an additional portion of the title compound (38.3 g, 25%) at a white solid.

Preparation 10: Methyl tert-butoxy(4-iodo-2-methyl-5,6,7,8-tetrahydro[1]benzothieno[2,3-b]pyridin-3-yl)acetate

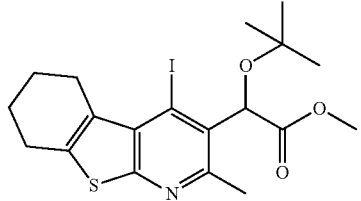 [SMILES: COC(=O)C(OC(C)(C)C)c1c(C)nc2sc3c(c2c1I)CCCC3]

A suspension of methyl hydroxy(4-iodo-2-methyl-5,6,7,8-tetrahydro[1]benzothieno[2,3-b]pyridin-3-yl)acetate (Preparation 9, 10.0 g, 23.97 mmol) in tert-butyl acetate (250 mL) was stirred vigorously for 5 minutes prior to the dropwise addition of perchloric acid (70%, 6.15 mL, 71.90 mmol). The resulting mixture was stirred at room temperature for 20 minutes. The mixture was neutralised by addition of a saturated aqueous sodium hydrogen carbonate solution (60 mL) and extracted with ethyl acetate (250 mL). The layers were separated and the aqueous layer was further extracted with ethyl acetate (250 mL). The combined organic layers were washed with brine (250 mL), dried over MgSO$_4$ and concentrated in vacuo to yield the crude product. The residue was purified by flash column chromatography eluting with ethyl acetate/heptane (10-40%) to give the title compound, 4.26 g, in a 38% yield. $^1$H NMR (400 MHz, CDCl$_3$) δ ppm 1.23 (s, 9 H), 1.81-1.92 (m, 4 H), 2.66 (s, 3 H), 2.79-2.89 (m, 2 H), 3.21-3.27 (m, 2 H), 3.68 (s, 3 H), 5.95 (s, 1 H).

Preparation 11: Ethyl-2-tert-butoxyl(4-iodo-2-methyl-5,6,7,8-tetrahydro[1]benzothieno[2,3-b]pyridin-3-yl)acetate

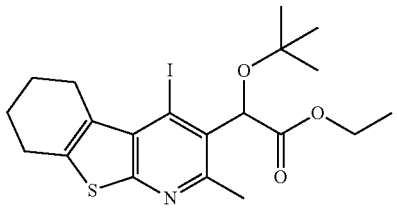 [SMILES: CCOC(=O)C(OC(C)(C)C)c1c(C)nc2sc3c(c2c1I)CCCC3]

Ethyl-2-[4-iodo-2-methyl-5,6,7,8-tetrahydro[1]benzothieno[2,3-b]pyridine-3-yl]-2-hydroxyacetate (3 g, 7 mmol) was taken up in 20 mL dichloromethane and tert-butyl acetate (20 mL, 170 mmol) and the mixture coiled to 3° C. in an ice/water bath. Concentrated sulphuric acid (1.14 mL, 21 mmol) was then added dropwise and the mixture allowed to warm to room temperature over 3 hours. The reaction was quenched by the addition of 100 mL of 1M NaOH and 100 mL water and the organic layer separated. The organics were washed with brine (100 mL), dried over $MgSO_4$ and evaporated under reduced pressure. The residue was purified by flash chrmoatography using a gradient of EtOAc in heptane as eluant (0:100 to 30:70) to afford the title compound as a white solid (1.22 g, 36%). $^1$H NMR (400 MHz, $CDCl_3$) δ 1.20 (t, 3H), 1.23 (s, 9H), 1.81-1.94 (m, 4H), 2.66 (s, 3H), 2.80-2.87 (m, 2H), 3.22-3.31 (m, 2H), 4.10-4.22 (m, 2H), 5.90 (s, 1H).

Preparation 12: Tert-butoxy(4-iodo-2-methyl-5,6,7,8-tetrahydro[1]benzothieno[2,3-b]pyridin-3-yl)acetic acid

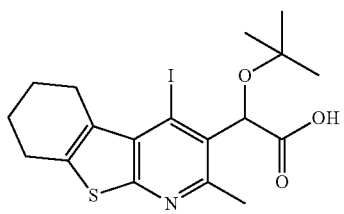 [SMILES: Cc1nc2sc3c(c2c(I)c1C(OC(C)(C)C)C(=O)O)CCCC3]

To a solution of Methyl tert-butoxy(4-iodo-2-methyl-5,6,7,8-tetrahydro[1]benzothieno[2,3-b]pyridin-3-yl)acetate (Preparation 10, 63.95 g, 135 mmol) in tetrahydrofuran (1 L) and methylated spirit (1 L) was dropwise added aqueous sodium hydroxide (1 M, 811 mL, 811 mmol). The resulting mixture was stirred at 60° C. for 90 minutes and then allowed to cool to room temperature overnight. The volatile solvents were removed in vacuo, and the remaining aqueous residue was diluted with water (400 mL) and extracted with tert-butyl methyl ether (600 mL). The organic layer was washed with water (400 mL) and then cooled on ice. 2 M hydrochloric acid was added to pH 5 and the resulting solids were collected by filtration, washing with water. The solid was dissolved in 2-methyl tetrahydrofuran (300 mL) and stirred for 10 minutes. An aqueous layer had appeared and this was separated. The aqueous layer was extracted with 2-methyl tetrahydrofuran (2×300 mL). The combined organic layers were dried over $MgSO_4$ and concentrated in vacuo to give the title compound as a pale yellow solid, 54.35 g, in an 88% yield. $^1$H NMR (400 MHz, $CDCl_3$) δ ppm 1.27 (s, 9 H), 1.81-1.93 (m, 4 H), 2.65 (s, 3 H), 2.76-2.88 (m, 2 H), 3.20-3.27 (m, 2 H), 6.13 (s, 1 H), 9.66 (br s, 1 H).

Preparation 13: (4R)-4-benzyl-3-[(2R)-2-tert-butoxy-2-(4-iodo-2-methyl-5,6,7,8-tetrahydro[1]benzothieno[2,3-b]pyridin-3-yl)acetyl]-1,3-oxazolidin-2-one (13A) and (4R)-4-benzyl-3-[(2S)-2-tert-butoxy-2-(4-iodo-2-methyl-5,6,7,8-tetrahydro[1]benzothieno[2,3-b]pyridin-3-yl)acetyl]-1,3-oxazolidin-2-one (13B)

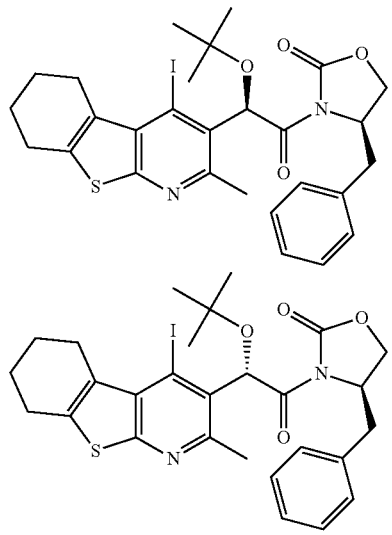

To a solution of tert-butoxy(4-iodo-2-methyl-5,6,7,8-tetrahydro[1]benzothieno[2,3-b]pyridin-3-yl)acetic acid (Preparation 12, 54.35 g, 118 mmol) in tetrahydrofuran (1 L) were added [(benzotriazol-1-yloxy)-dimethylamino-methylene]-dimethyl-ammonium hexafluoro phosphate (67.31 g, 177 mmol) and ethyl-di-isopropyl-amine (61.8 mL, 355 mmol) and the resulting reaction mixture was stirred at 40° C. for 2 hours. After 90 minutes (R)-4-benzyl-2-oxazolidinone (41.93 g, 237 mmol) was dissolved in tetrahydrofuran (500 mL) and treated with sodium hydride (60% in mineral oil) and stirred for 30 minutes at room temperature. After this time, the two mixtures were combined and stirred at 40° C. for 8 hours. Precipitated material was collected by filtration. Solids were partitioned between ethyl acetate (500 mL) and a saturated aqueous solution of sodium hydrogen carbonate (500 mL). The layers were separated and the aqueous layer was further extracted with ethyl acetate (2×500 mL). The combined organic layers were washed with brine (500 mL), dried over $MgSO_4$ and concentrated in vacuo to yield a brown oil, 1.2 g. The original THF filtrate was washed with a saturated aqueous solution of sodium hydrogen carbonate (500 mL) with the addition of ethyl acetate (1 L) to enable separation of layers. The aqueous layer was washed with ethyl acetate (2×250 mL). The combined organic extracts were washed with brine (500 mL), dried over $MgSO_4$ and concentrated in vacuo. The crude residue was combined with the brown oil from the solids work up and purified by dry flash column chromatography eluting with a gradient of heptane and ethyl acetate (0% to 20%). Product containing fractions were concentrated in vacuo to give a pale yellow semi-solid, 72 g. The residue was further purified by column chromatography eluting with a gradient of heptane and ethyl acetate (0% to 10%) to separate the diastereomers. Both were recrystallised from methylated spirits. The top running spot was isolated as a white solid, 23.75 g, in a 32% yield (13A). The bottom running spot was isolated as a white solid, 21.36 g, in a 29% yield (13B). 13A: $^1$H NMR (400 MHz, CDCl$_3$) δ ppm 1.25 (s, 9 H), 1.80-1.92 (m, 4 H), 2.85 (s, 3 H), 2.79-2.90 (m, 2 H), 2.94 (dd, 1 H), 3.15-3.30 (m, 2 H), 4.16 (dd, 1 H), 4.26 (t, 1 H), 4.71-4.80 (m, 1 H), 6.90 (s, 1 H), 7.23-7.36 (m, 4 H). 13B: $^1$H NMR (400 MHz, CDCl$_3$) δ ppm 1.17 (s, 9 H), 1.82-1.95 (m, 4 H), 2.84 (s, 3 H), 2.78-2.87 (m, 3 H), 3.18-3.31 (m, 2 H), 4.17-4.22 (m, 1 H), 4.30 (t, 1 H), 4.70-4.78 (m, 1 H), 6.93 (s, 1 H), 7.17-7.33 (m, 4 H).

Preparation 14: (2R)-tert-butoxyl(4-iodo-2-methyl-5,6,7,8-tetrahydro[1]benzothieno[2,3-b]pyridin-3-yl) acetic acid

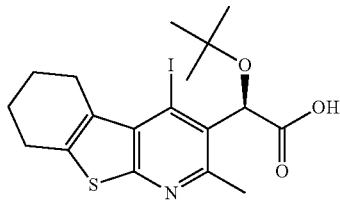 [SMILES: Cc1nc2sc3c(c2c(I)c1[C@@H](OC(C)(C)C)C(=O)O)CCCC3]

To a solution of (4R)-4-benzyl-3-[(2R)-2-tert-butoxy-2-(4-iodo-2-methyl-5,6,7,8-tetrahydro[1]benzothieno[2,3-b]pyridin-3-yl)acetyl]-1,3-oxazolidin-2-one (Preparation 13A, 23.75 g, 38.40 mmol) in tetrahydrofuran (450 mL) and water (150 mL) at 0° C. was added dropwise a solution of lithium hydroxide hydrate (3.35 g, 80.64 mmol) and hydrogen peroxide (27% aqueous, 18.3 mL, 161.27 mmol). The resulting solution was stirred at 0° C. for 15 minutes, then for 2 hours at room temperature. A saturated solution of sodium sulphite (500 mL) was added followed by water (500 mL), and the mixture stirred for 15 minutes. The mixture was acidified to pH 4 by the addition of 6 M hydrochloric acid. The mixture was extracted with dichloromethane (4×500 mL). The combined organic layers were dried over MgSO$_4$ and concentrated in vacuo. The resulting white solid was crystallised from methylated spirits (150 mL) with heating at reflux for 5 minutes. The Mixture was allowed to cool to room temperature overnight. The resulting solid was collected by filtration and washed with cold methylated spirits and dried in vacuo to give the title compound as a white solid, 12.01 g, in a 68% yield.

$^1$H NMR (400 MHz, CDCl$_3$) δ ppm 1.27 (s, 9 H), 1.81-1.93 (m, 4 H), 2.665 (s, 3 H), 2.75-2.88 (m, 2 H), 3.18-3.28 (m, 2 H), 6.13 (s, 1 H), 9.66 (br s, 1 H).

Preparation 15: (2S)-tert-butoxy(4-iodo-2-methyl-5,6,7,8-tetrahydro[1]benzothieno[2,3-b]pyridin-3-yl) acetic acid

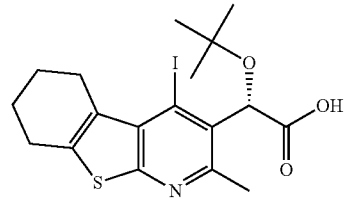 [SMILES: Cc1nc2sc3c(c2c(I)c1[C@H](OC(C)(C)C)C(=O)O)CCCC3]

To a solution of (4R)-4-benzyl-3-[(2S)-2-tert-butoxy-2-(4-iodo-2-methyl-5,6,7,8-tetrahydro[1]benzothieno[2,3-b]pyridin-3-yl)acetyl]-1,3-oxazolidin-2-one (Preparation 13B, 21.36 g, 34.53 mmol) in tetrahydrofuran (400 mL) and water (130 mL) at 0° C. was added dropwise a solution of lithium hydroxide hydrate (3.04 g, 72.52 mmol) and hydrogen peroxide (27% aqueous, 16.4 mL, 145.04 mmol). The resulting solution was stirred at 0° C. for 15 minutes, then for 2 hours at room temperature. A saturated solution of sodium sulphite (500 mL) was added followed by water (500 mL), and the mixture stirred for 15 minutes. The mixture was acidified to pH 4 by the addition of 6 M hydrochloric acid. The mixture was extracted with dichloromethane (4×500 mL). The combined organic layers were dried over MgSO$_4$ and concentrated in vacuo. The resulting white solid was crystallised from methylated spirits (150 mL) with heating at reflux for 5 minutes. The mixture was allowed to cool to room temperature overnight. The resulting solid was collected by filtration and washed with cold methylated spirits and dried in vacuo to give the title compound as a white solid, 10.25 g, in a 65% yield.

$^1$H NMR (400 MHz, CDCl$_3$) δ ppm 1.27 (s, 9 H), 1.81-1.93 (m, 4 H), 2.65 (s, 3 H), 2.75-2.88 (m, 2 H), 3.18-3.28 (m, 2 H), 6.13 (s, 1 H).

Preparation 16: Methyl (2S)-tert-butoxy(4-iodo-2-methyl-5,6,7,8-tetrahydro[1]benzothieno[2,3-b]pyridin-3-yl)acetate

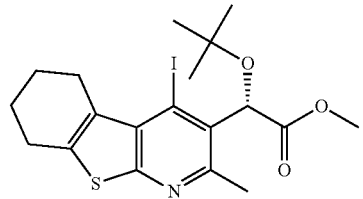 [SMILES: COC(=O)[C@@H](OC(C)(C)C)c1c(C)nc2sc3c(c2c1I)CCCC3]

To a solution of (2S)-tert-butoxy(4-iodo-2-methyl-5,6,7,8-tetrahydro[1]benzothieno[2,3-b]pyridin-3-yl)acetic acid (Preparation 15, 1.0 g, 2.178 mmol) in dichloromethane (34 mL) was added [(benzotriazol-1-yloxy)-dimethylamino-methylene]-dimethyl-ammonium hexafluoro phosphate (1.24 g, 3.266 mmol) and ethyl-di-isopropyl-amine (600 μL, 3.266 mmol) and the resulting reaction mixture was stirred at 30° C. for 2 hours. Methanol (17 mL) was added and the reaction mixture was stirred at 30° C. for 18 hours. The reaction was cooled to room temperature and diluted with dichloromethane (50 mL). The solution was washed with a saturated aqueous solution of sodium hydrogen carbonate (50 mL), water (50 mL) and brine (50 mL). The organic layer was dried over MgSO₄ and concentrated in vacuo. The residue was purified by flash chromatography eluting with 5% ethyl acetate in heptane to give the title compound as a white solid, 963 mg, in a 93% yield. ¹H NMR (400 MHz, CDCl₃) δ ppm 1.22 (s, 9 H), 1.85-1.88 (m, 4 H), 2.65 (s, 3 H), 2.82-2.66 (m, 2 H), 3.23-3.26 (m, 2 H), 3.68 (s, 3 H), 5.94 (s, 1 H).

Preparation 17: (4-chloro-2-hydroxyphenyl)boronic acid

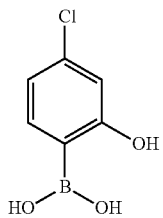

To a solution of (4-chloro-2-methoxyphenyl)boronic acid (1.0 g, 5.36 mmol) in dichloromethane (5 mL) at 0° C. was added boron tribromide (1 M in dichloromethane, 10 mL, 10 mmol). The reaction was stirred at 0° C. for 1 hour, then allowed to warm to room temperature and stirred as such for 18 hours. The reaction was quenched carefully with water. The resulting precipitate was collected by filtration, to give a white solid, 260 mg. The layers were separated and the organic layer was dried over Na₂SO₄ and concentrated in vacuo to give a white solid, 300 mg. The two batches of solid were combined to give the title compound as a white solid, 560 mg, in a 61% yield. This material was taken on to Preparation 18 without purification.

Preparation 18: 5-chloro-2-(4,4,5,5-tetramethyl-1,3,2-dioxaborolan-2-yl)phenol

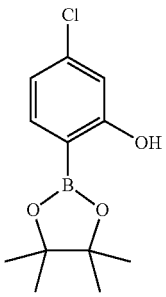 [SMILES: CC1(C)OB(c2ccc(Cl)cc2O)OC1(C)C]

To a solution of (4-chloro-2-hydroxyphenyl)boronic acid (Preparation 15, 200 mg, 1.16 mmol) in dichloromethane (15 mL) was added pinacol (274 mg, 2.32 mmol) and the resulting solution was stirred at room temperature for 18 hours. The reaction mixture was washed with water (10 mL), dried over Na₂SO₄ and concentrated in vacuo to give the title compound as a pale yellow solid, 280 mg, in a 95% yield.

¹H NMR (400 MHz, CDCl₃) δ ppm 1.35 (s, 12 H), 6.86-6.88 (m, 2 H), 7.51 (d, 1 H), 7.89 (s, 1 H).

Preparation 19: 2-(2-fluoro-4-methylphenyl)-4,4,5,5-tetramethyl-1,3,2-dioxaborolane

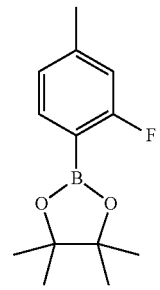 [SMILES: Cc1ccc(B2OC(C)(C)C(C)(C)O2)c(F)c1]

To a solution of (2-fluoro-4-methylphenyl)boronic acid (500 mg, 3.24 mmol) in diethyl ether (20 mL) was added pinacol (360 mg, 3.24 mmol) and 4-toluenesulfonic acid monohydrate (30 mg, 162 μmol) and the resulting solution was stirred at room temperature for 18 hours. The reaction mixture was washed with a saturated aqueous sodium hydrogen carbonate solution (20 mL), dried over MgSO₄ and concentrated in vacuo to give the title compound as a white solid, 740 mg, in a 97% yield. ¹H NMR (400 MHz, CDCl₃) δ ppm 1.33 (s, 12 H), 2.34 (s, 3 H), 6.82 (d, 1 H), 6.93 (d, 1 H), 7.60 (d, 1 H).

EXAMPLE 1

Tert-butoxy(2-methyl-4-pyrimidin-5-yl-5,6,7,8-tetrahydro[1]benzothieno[2,3-b]pyridin-3-yl)acetic acid

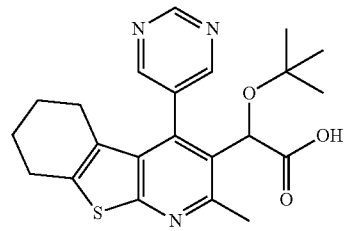 [SMILES: Cc1nc2sc3c(c2c(-c2cncnc2)c1C(OC(C)(C)C)C(=O)O)CCCC3]

Methyl-tert-butoxy[4-iodo-2-methyl-5,6,7,8-tetrahydro[1]benzothieno[2,3-b]pyridine-3-yl]acetate (Preparation 10) may be reacted with pyrimidine boronic acid in the presence of potassium carbonate and tetrakis(triphenylphosphine)palladium(0) to provide the methyl ester of the above compound. Hydrolysis with aqueous lithium hydroxide may be used to provide the final product.

Antiviral Activity>20 μM (n=2) (S8737E)

EXAMPLE 2

(2S)-tert-butoxy(2-methyl-4-pyrimidin-5-yl-5,6,7,8-tetrahydro[1]benzothieno[2,3-b]pyridin-3-yl)acetic acid

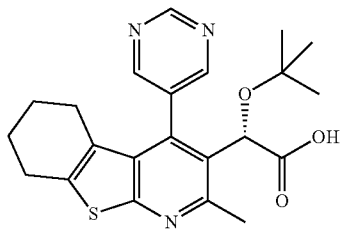 [SMILES: Cc1nc2sc3c(c2c(-c2cncnc2)c1[C@H](OC(C)(C)C)C(=O)O)CCCC3]

A sample of the product from Example 1 may be dissolved in a mixture of methanol and dichloromethane (1:1) loaded onto a Chiralpak IC column (250×20 mm internal diameter) and eluted with methanol/CO$_2$ (60:40) at ambient temperature and a flow rate of 60 g/min. Fractions containing a single enantiomer may be combined and evaporated under reduced pressure to give the product enantiomer. Chiral purity may be assessed by chiral hplc using a Chiralpak IC column eluting with hexane/isopropanol.

EXAMPLE 3

Ethoxy[4-(2-hydroxy-4-methylphenyl)-2-methyl-5,6,7,8-tetrahydro[1]benzothieno[2,3-b]pyridin-3-yl]acetic acid

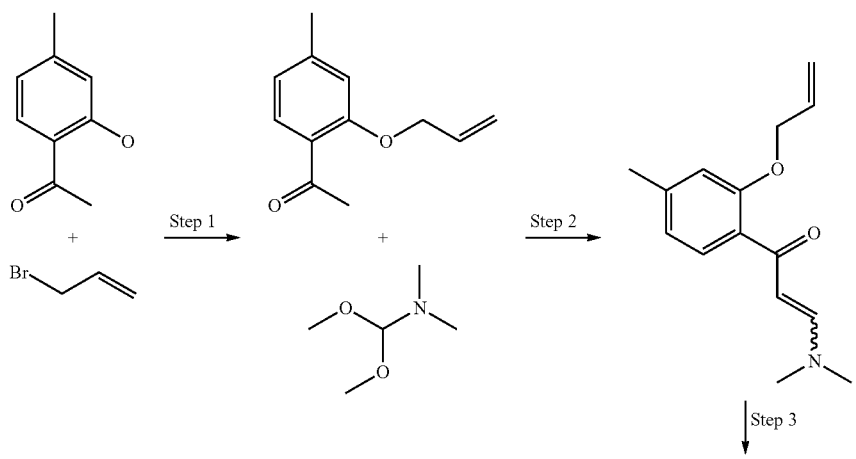

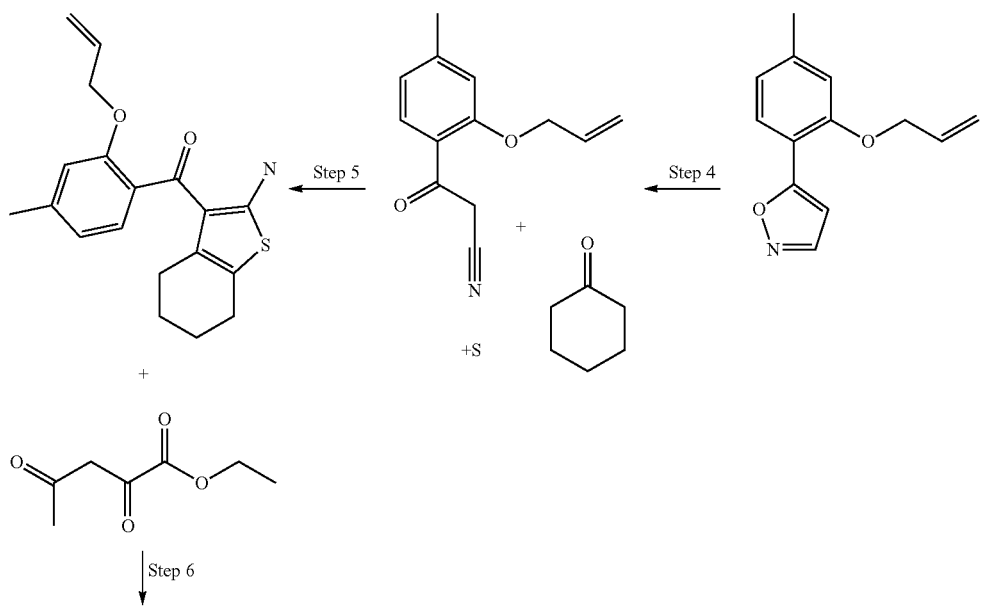

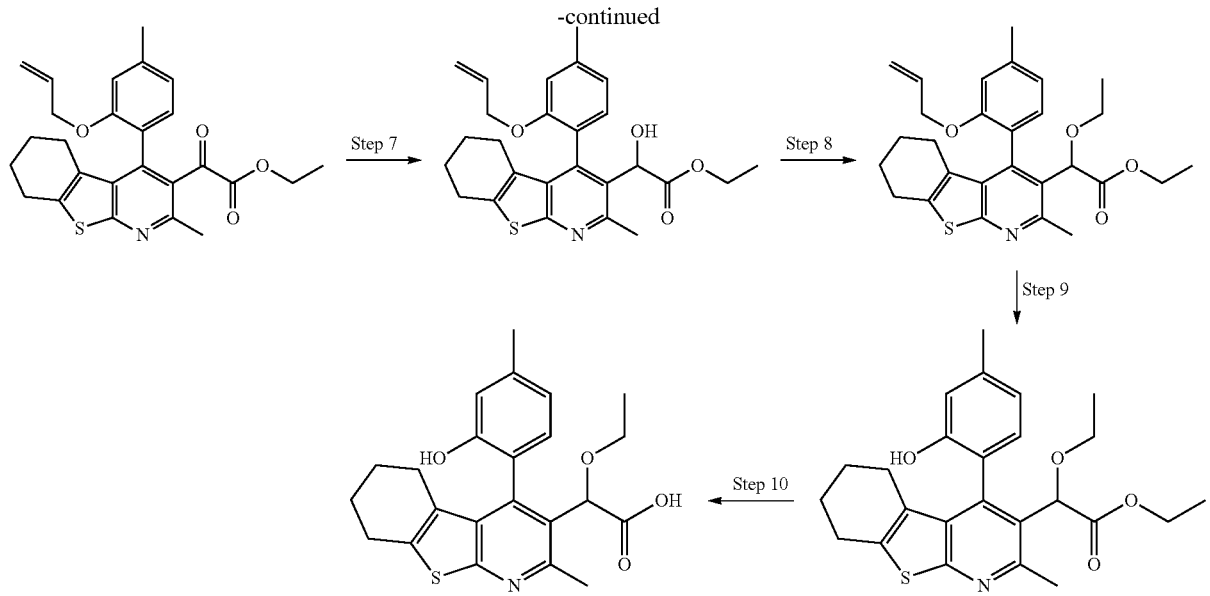

Step 1

To a solution of 1-(2-hydroxy-4-methyl-phenyl)-ethanone (10 g, 67 mmols) in dimethylformamide (100 mL) was added potassium carbonate (18.4 g, 2 eq, 133 mmols), followed by allyl bromide (8.06 g, 5.75 mL, 1 eq. 67 mmols). The reaction was stirred at room temperature for 16 hours. The residue was partitioned between ethyl acetate (200 mL) and water (800 mL), the organics were separated, and washed with brine (50 mL), dried (MgSO4), filtered and concentrated in vacuo. After cooling the concentrate to room temperature 1-(2-allyloxy-4-methyl-phenyl)-ethanone crystallised as colourless platelets 12.40 g (98% yield). LCMS (2 min acidic) 1.20 min 72-100% pure by UV, ES+/AP+ 191. HNMR (CDCl$_3$)>95% pure 7.68 (d, J=8.01 Hz, 1 H), 6.80-6.83 (m, 1 H), 6.76 (s, 1 H), 6.10 (m, 1 H), 5.44 (dq, J=17.5, 1.5 Hz, 1 H), 5.33 (dq, J=11.0 Hz, 1.5 Hz, 1 H), 4.61-4.66 (m, 2 H), 2.63 (s, 3 H), 2.37 (s, 3 H).

Step 2

To 1-(2-allyloxy-4-methyl-phenyl)-ethanone (13.9 g, 73 mmols) was added dimethylformamide dimethylacetal (56 mL, 422 mols, 5.8 eq), and the reaction was heated to reflux overnight. The reaction was then concentrated in vacuo to give an orange oil of 1-(2-allyloxy-4-methyl-phenyl)-3-dimethylamino-propenone (17.9 g) which was taken crude into the next reaction.

Step 3

To a stirred solution of crude 1-(2-allyloxy-4-methyl-phenyl)-3-dimethylamino-propenone (14.1 g, 57.5 mmols) in methanol (70 mL) was added hydroxylamine hydrochloride (4.4 g, 63 mmols, 1.1 eq) and the reaction was stirred at room temperature for 1 hour. Colourless needle crystals were filtered off and analysed and found to be 5-(2-allyloxy-4-methyl-phenyl)-isoxazole 7.3 g (58% yield). LCMS (2 min acidic) 1.32 min 64-91% pure by UV, ES+/AP+ 216. HNMR (CDCl$_3$)>95% pure 7.88 (d, J=8.01 Hz, 1 H), 6.88-6.92 (m, 1 H), 6.82 (s, 1 H), 6.77 (m, 1 H), 6.05-6.20 (m, 1 H), 5.46 (dq, J=17.0, 1.5 Hz, 1 H), 5.35 (dq, J=10.5, 1.5 Hz, 1 H), 4.67 (m, 2H), 2.40 (s, 3 H).

Step 4

To a stirred suspension of 5-(2-allyloxy-4-methyl-phenyl)-isoxazole (7.3 g, 33.8 mmols) in ethanol (40 mL) was added sodium ethoxide (21% solution in ethanol, 40 mL, 110 mmols, 3.2 eq) and the reaction was stirred at room temperature for 3 hours. The reaction was acidified to pH 2 with hydrochloric acid (2N, aqueous) and the solid was filtered off and air dried for 1 hour. The off white solid, 4.8 g (66% yield) was analysed and found to be pure 3-(2-Allyloxy-4-methyl-phenyl)-3-oxo-propionitrile. LCMS (2 min acidic) 1.12 min 51-100% pure by UV, ES+/AP+ 216, ES−/AP− 214. HNMR (CDCl$_3$)>95% pure 7.80 (d, J=8.0 Hz, 1 H), 6.88 (dd, J=8.0, 1.0 Hz, 1 H), 6.79 (s, 1 H), 6.13 (m, 1 H), 5.37-5.50 (m, 2 H), 4.67-4.70 (m, 2 H), 4.08 (s, 2 H), 2.41 (s, 3 H).

Step 5

To a stirred solution of 3-(2-allyloxy-4-methyl-phenyl)-3-oxo-propionitrile (1 g, 4.6 mmols) in ethanol (20 mL) was added cylohexanone (684 mg, 722 μL, 7 mmols, 1.5 eq), and sulfur (224 mg, 7 mmols, 1.5 eq), followed by morpholine (607 mg, 610 μL, 7 mmols, 1.5 eq) and the reaction was stirred overnight at 40° C. The reaction was concentrated in vacuo. The residue was purified using ISCO Companion with a Redisep silica gel 40 g cartridge and a gradient of heptane and ethyl acetate (0% to 40%). Fractions containing desired product were combined and concentrated in vacuo to give (2-allyloxy-4-methyl-phenyl)-(2-amino-4,5,6,7-tetrahydro-benzo[b]thiophen-3-yl)-methanone as a yellow gum 1.1 g (72% yield). LCMS (2 min acidic) 1.45 min 58-100% pure by UV, ES+/AP+ 328. HNMR (CDCl$_3$)>95% pure 7.08 (d, J=7.5 Hz, 1 H) 6.91 (br. s., 2 H) 6.78 (dq, J=7.5, 0.5 Hz, 1 H) 6.69 (s, 1 H) 5.92 (m, J=17.0, 10.5, 5.0, 5.0 Hz, 1 H) 5.13-5.28 (m, 2 H) 4.52 (dt, J=5.0, 2.0 Hz, 2 H) 2.47 (tt, J=6.0, 2.0 Hz, 2 H) 2.36 (s, 3 H) 1.78 (tt, J=6.0, 2.0 Hz, 2 H) 1.64-1.71 (m, 2 H) 1.44-1.51 (m, 2 H).

Step 6

To a stirred solution of (2-allyloxy-4-methyl-phenyl)-(2-amino-4,5,6,7-tetrahydro-benzo[b]thiophen-3-yl)-methanone (882 mg, 2.69 mmols) in ethanol (30 mL) was added ethyl 2,4-dioxopentanoate (426 mg, 378 μL, 1 eq) followed by acetyl chloride (846 mg, 766 μL, 4 eq), and the reaction was heated to 50° C. for 1 hour. The reaction was then concentrated in vacuo to give [4-(2-allyloxy-4-methyl-phenyl)-2-methyl-5,6,7,8-tetrahydro-benzo[4,5]thieno[2,3-b]pyridin-3-yl]-oxo-acetic acid ethyl ester hydrochloride as a pale yellow oil 1 g (86% yield). LCMS (2 min acidic) 1.70 min 54-100% pure by UV, ES+/AP+ 450. HNMR (CDCl$_3$) >90% pure 6.95 (d, J=7.0 Hz, 1 H) 6.87 (d, J=7.0 Hz, 1 H) 6.76 (s, 1 H) 5.82 (m, 1 H) 5.09-5.20 (m, 2 H) 4.39-4.51 (m, 2 H) 3.84-3.94 (m, 2 H) 2.95 (s, 3 H) 2.87-2.93 (m, 2 H) 2.43 (s, 3 H) 1.92-2.08 (m, 2 H) 1.78-1.89 (m, 2 H) 1.55-1.70 (m, 2 H) 1.12 (t, J=7.1 Hz, 3 H).

Step 7

To a stirred solution of [4-(2-Allyloxy-4-methyl-phenyl)-2-methyl-5,6,7,8-tetrahydro-benzo[4,5]thieno[2,3-b]pyridin-3-yl]-oxo-acetic acid ethyl ester hydrochloride (1.1 g, 2.56 mmols) in ethanol (20 mL) was added sodium borohydride (145 mg, 1.5 eq, 3.84 mmols), and the reaction was stirred at room temperature for 5 minutes. The reaction was concentrated in vacuo, and the residue was partitioned between ethyl acetate (20 mL) and hydrochloric acid (aqueous, 1N, 30 mL). The organics were separated, washed with brine (10 mL), dried (MgSO4), filtered and concentrated in vacuo to give crude [4-(2-allyloxy-4-methyl-phenyl)-2-methyl-5,6,7,8-tetrahydro-benzo[4,5]thieno[2,3-b]pyridin-3-yl]-hydroxy-acetic acid ethyl ester as a pale orange gum 1.1 g (91% yield). LCMS (2 min acidic) 1.53 min 52-81% pure by UV, ES+/AP+ 452. HNMR (CDCl$_3$)>80% pure 7.02 (d, J=7.4 Hz, 1 H) 6.81-6.85 (m, 1 H) 6.79 (s, 1 H) 5.86 (m, 1 H) 5.18 (s, 1 H) 5.08-5.17 (m, 2 H) 4.47-4.51 (m, 2 H) 4.08-4.22 (m, 2 H) 2.81 (t, J=6.2 Hz, 2 H) 2.63 (s, 3 H) 2.43 (s, 3 H) 1.71-1.87 (m, 4 H) 1.53-1.64 (m, 2 H) 1.17-1.21 (m, 3 H).

Step 8

To a stirred solution of [4-(2-Allyloxy-4-methyl-phenyl)-2-methyl-5,6,7,8-tetrahydro-benzo[4,5]thieno[2,3-b]pyridin-3-yl]-hydroxy-acetic acid ethyl ester (100 mg, 221 μmols, 1 eq) in MeCN (5 mL) was added silver oxide (102 mg, 442 μmols, 2 eq) followed by iodoethane (172 mg, 89 uL, 5 eq) and the reaction was stirred for 16 hours at 60° C. Additional iodoethane (1 mL, 50 eq) and silver (I) oxide (102 mg, 2 eq) was added and the reaction was continued to be heated at 60° C. for 16 hours. The reaction was diluted with MeCN (5 mL), and filtered. The filtrate was then concentrated in vacuo. The residue was purified using ISCO Companion with a Redisep silica gel 12 g cartridge and a gradient of heptane and ethyl acetate (0% to 30%). Fractions containing (4-(2-allyloxy-4-methyl-phenyl)-2-methyl-5,6,7,8-tetrahydro-benzo[4,5]thieno[2,3-b]pyridin-3-yl)-ethoxy-acetic acid ethyl ester were combined and concentrated in vacuo to give the desired product as a pale orange oil, 22 mg (22% yield). LC-MS (12 min acidic) 7.55 mins 100% pure by UV, ES+/APCI+ 480.

Step 9

To a stirred solution of [4-(2-Allyloxy-4-methyl-phenyl)-2-methyl-5,6,7,8-tetrahydro-benzo[4,5]thieno[2,3-b]pyridin-3-yl]-ethoxy-acetic acid ethyl ester (22 mg, 46 μmols) in dichloromethane (3 mL) was added 1,3-dimethylbarbituric acid (38 mg, 240 μmols, 5 eq), and the reaction was evacuated and filled with nitrogen. Palladium tetrakis(triphenylphosphine) (1.2 mg, 2 mol %) was added and the reaction was heated to reflux for 16 hours. The reaction was concentrated in vacuo. The residue was purified using ISCO Companion with a Redisep silica gel 4 g cartridge and a gradient of heptane and ethyl acetate (0% to 40%). Fractions containing desired product were combined and concentrated in vacuo to give ethoxy-[4-(2-hydroxy-4-methyl-phenyl)-2-methyl-5,6,7,8-tetrahydro-benzo[4,5]thieno[2,3-b]pyridin-3-yl]-acetic acid ethyl ester as a pale yellow oil, 20 mg (95% yield). LC-MS (12 min acidic) 6.40 mins 58-69% pure by UV, ES+/APCI+ 440, ES−/APCI− 438; 6.66 mins 27-31% pure by UV, ES+/APCI+ 440, ES−/APCI− 438.

Step 10

To a stirred solution of Ethoxy-[4-(2-hydroxy-4-methyl-phenyl)-2-methyl-5,6,7,8-tetrahydro-benzo[4,5]thieno[2,3-b]pyridin-3-yl]-acetic acid ethyl ester (20 mg, 45 μmols) in ethanol (1 mL) and tetrahydrofuran (1 mL) was added the sodium hydroxide (2N aqueous, 0.5 mL, 20 eq) and the reaction was stirred at 60° C. for 5 hours. The reaction was concentrated in vacuo until all organic solvents had been removed, the aqueous residue was then acidified with hydrochloric acid (2N aqueous) to pH 2. A pale yellow solid, 4 mg (16% yield) was filtered off and analysed and found to contain ethoxy-[4-(2-hydroxy-4-methyl-phenyl)-2-methyl-5,6,7,8-tetrahydro-benzo[4,5]thieno[2,3-b]pyridin-3-yl]-acetic acid. LC-MS (12 min acidic) 5.04 mins 47-43% pure by UV, ES+/APCI+ 412, ES−/APCI− 410; 5.80 mins 12-13% pure by UV, ES+/APCI+ 412, ES−/APCI− 410.

EXAMPLE 4

2-tert-butoxy(4-iodo-2-methyl-5,6,7,8-tetrahydro[1]benzothieno[2,3-b]pyridin-3-yl)acetic acid

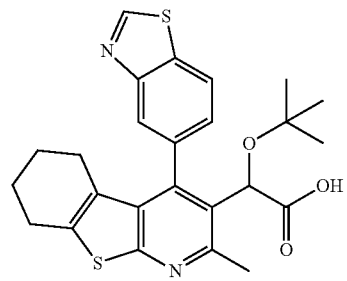 [SMILES: Cc1nc2sc3c(c2c(-c2ccc4scnc4c2)c1C(OC(C)(C)C)C(=O)O)CCCC3]

5-Benzothiazole-boronic acid (150 μmol) and ethyl-2-tert-butoxy(4-iodo-2-methyl-5,6,7,8-tetrahydro[1]benzothieno[2,3-b]pyridin-3-yl)acetate (Preparation 11, 1 mL of a 0.1M solution in dioxane, 100 μmol) were added to a reaction vial. A 1M solution of caesium carbonate (200 μL, 200 μmol) in water was then added, followed by 55 μmol of Pd(dppf)Cl$_2$ and the whole stirred at 100° C. for 16 h before cooling to room temperature and evaporation of the solution under reduced pressure to give a yellow residue. A 2M solution of lithium hydroxide in water (200 μL, 400 μmol) was added to each vial, followed by 1 mL of THF, and the mixture was shaken at room temperature for 16 h. The pH of the solution was adjusted to neutral using a 1M aqueous solution of hydrochloric acid, before the mixture was evaporated to dryness under reduced pressure and the residue then purified by preparative HPLC on a C18 column, using a mixture of acetonitrile and water as the mobile phase. Evaporation of the appropriate fractions under reduced pressure provided the title compound (11 mg, 23%) as a white solid. ESI/APC(+): 467 (M+H).

The following Examples were synthesised according to the method described in Example 4 using the appropriate aryl boronic acid.

| Example | Mass | Structure | Antiviral Activity (S8737E, μM) | HTRF Interaction assay (S9118, μM) |
|---|---|---|---|---|
| 4 | 467 | 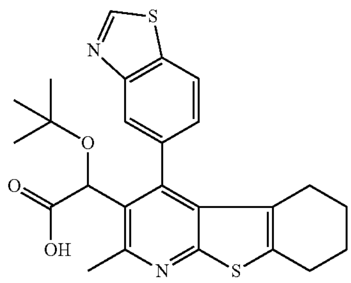 [SMILES: Cc1nc2sc3c(c2c(-c2ccc4scnc4c2)c1C(OC(C)(C)C)C(=O)O)CCCC3] | 0.282 (n = 2) | 3.48 (n = 2) |
| 5 | 454 | 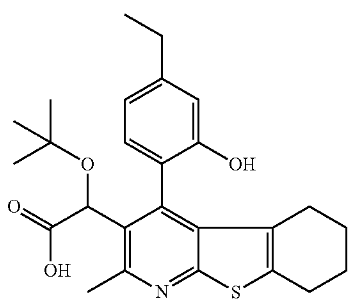 [SMILES: CCc1ccc(-c2c(C(OC(C)(C)C)C(=O)O)c(C)nc3sc4c(c23)CCCC4)c(O)c1] | 0.155 (n = 2) | 2.7 (n = 2) |
| 6 | 450 | 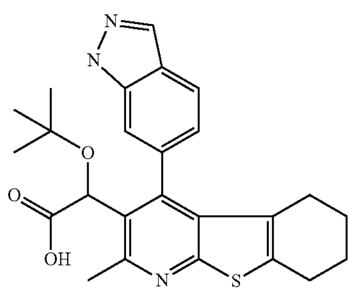 [SMILES: Cc1nc2sc3c(c2c(-c2ccc4cn[nH]c4c2)c1C(OC(C)(C)C)C(=O)O)CCCC3] | 0.305 (n = 2) | 2.63 (n = 2) |
| 7 | 441 | 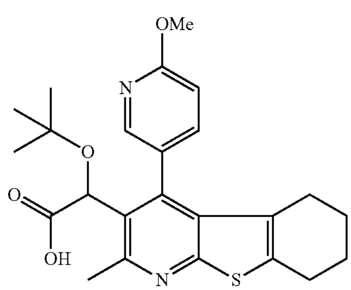 [SMILES: COc1ccc(-c2c(C(OC(C)(C)C)C(=O)O)c(C)nc3sc4c(c23)CCCC4)cn1] | 0.436 (n = 2) | 9.25 (n = 2) |
| 8 | 428 | 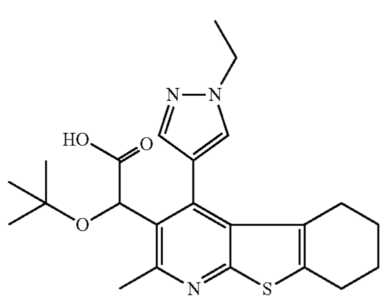 [SMILES: CCn1cc(-c2c(C(OC(C)(C)C)C(=O)O)c(C)nc3sc4c(c23)CCCC4)cn1] | 0.624 (n = 2) | 23.8 (n = 2) |

-continued

| Example | Mass | Structure | Antiviral Activity (S8737E, μM) | HTRF Interaction assay (S9118, μM) |
|---|---|---|---|---|
| 9 | 479 | 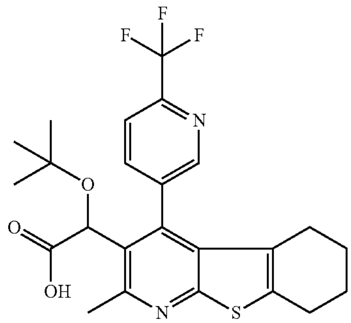 [SMILES: Cc1nc2sc3c(c2c(-c2ccc(C(F)(F)F)nc2)c1C(OC(C)(C)C)C(=O)O)CCCC3] | 0.683 (n = 2) | 11.7 (n = 2) |
| 10 | 464 | 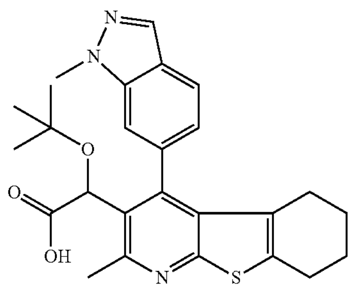 [SMILES: Cc1nc2sc3c(c2c(-c2ccc4cnn(C)c4c2)c1C(OC(C)(C)C)C(=O)O)CCCC3] | 0.795 (n = 2) | 7.87 (n = 2) |
| 11 | 464 | 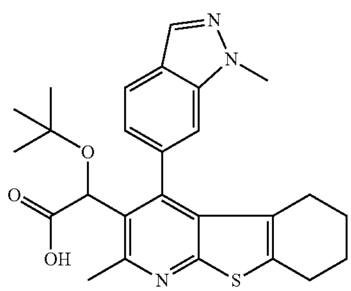 [SMILES: Cc1nc2sc3c(c2c(-c2ccc4cnn(C)c4c2)c1C(OC(C)(C)C)C(=O)O)CCCC3] | 0.814 (n = 2) | 12.2 (n = 2) |
| 12 | 464 | 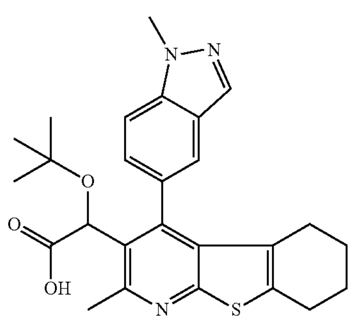 [SMILES: Cc1nc2sc3c(c2c(-c2ccc4c(cnn4C)c2)c1C(OC(C)(C)C)C(=O)O)CCCC3] | 0.941 (n = 2) | 5.13 (n = 2) |
| 13 | 440 | 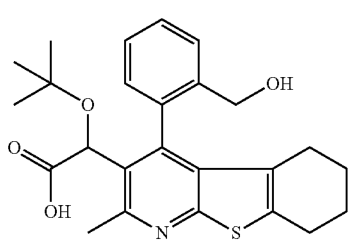 [SMILES: Cc1nc2sc3c(c2c(-c2ccccc2CO)c1C(OC(C)(C)C)C(=O)O)CCCC3] | 0.957 (n = 2) | 56.3 (n = 2) |

-continued

| Example | Mass | Structure | Antiviral Activity (S8737E, μM) | HTRF Interaction assay (S9118, μM) |
|---|---|---|---|---|
| 14 | 441 | 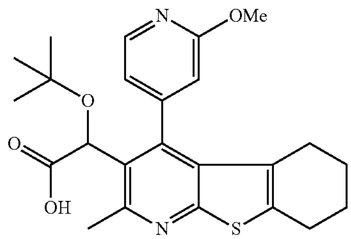 [SMILES: COc1cc(-c2c(C(OC(C)(C)C)C(=O)O)c(C)nc3sc4c(c23)CCCC4)ccn1] | 1.24 (n = 2) | 28.4 (n = 2) |
| 15 | 435 | 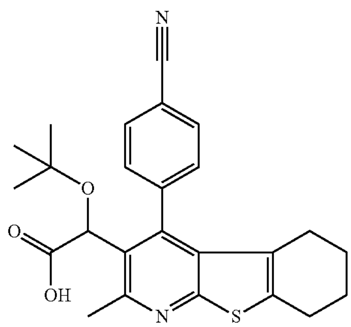 [SMILES: Cc1nc2sc3c(c2c(-c2ccc(C#N)cc2)c1C(OC(C)(C)C)C(=O)O)CCCC3] | 1.28 (n = 2) | 14.8 (n = 2) |
| 16 | 426 | 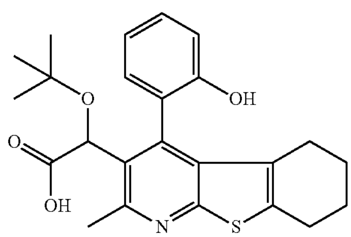 [SMILES: Cc1nc2sc3c(c2c(-c2ccccc2O)c1C(OC(C)(C)C)C(=O)O)CCCC3] | 1.73 (n = 2) | 57.4 (n = 2) |
| 17 | 450 | 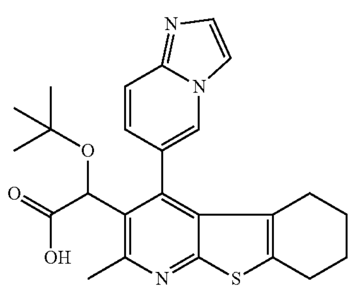 [SMILES: Cc1nc2sc3c(c2c(-c2ccc4nccn4c2)c1C(OC(C)(C)C)C(=O)O)CCCC3] | 1.78 (n = 2) | >100 (n = 2) |
| 18 | 451 | 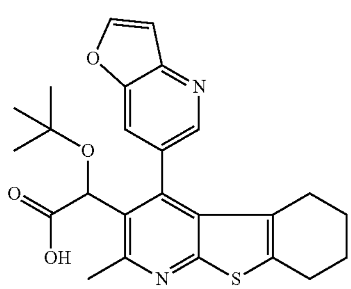 [SMILES: Cc1nc2sc3c(c2c(-c2cnc4ccoc4c2)c1C(OC(C)(C)C)C(=O)O)CCCC3] | 1.84 (n = 2) | 30.3 (n = 2) |

-continued

| Example | Mass | Structure | Antiviral Activity (S8737E, μM) | HTRF Interaction assay (S9118, μM) |
|---|---|---|---|---|
| 19 | 490 | 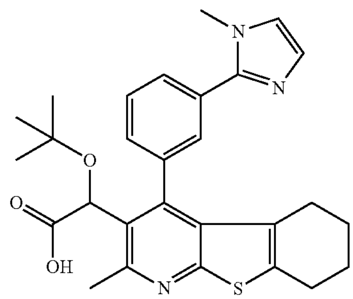 [SMILES: Cc1nc2sc3c(c2c(-c2cccc(-c4nccn4C)c2)c1C(OC(C)(C)C)C(=O)O)CCCC3] | 1.9 (n = 2) | 46.5 (n = 2) |
| 20 | 481 | 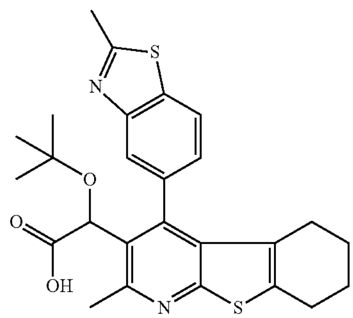 [SMILES: Cc1nc2cc(-c3c(C(OC(C)(C)C)C(=O)O)c(C)nc4sc5c(c34)CCCC5)ccc2s1] | 2.01 (n = 2) | 11.8 (n = 2) |
| 21 | 440 | 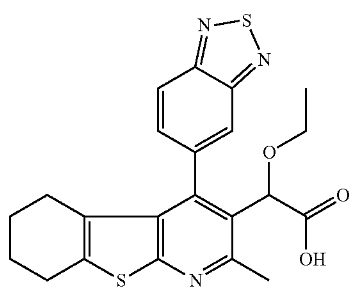 [SMILES: CCOC(C(=O)O)c1c(C)nc2sc3c(c2c1-c1ccc2nsnc2c1)CCCC3] | 2.17 (n = 2) | 64.8 (n = 2) |
| 22 | 481 | 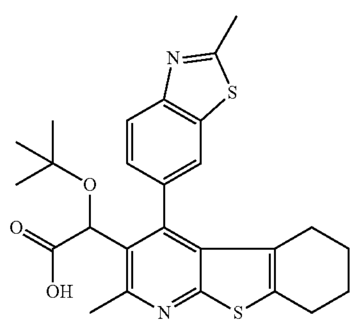 [SMILES: Cc1nc2ccc(-c3c(C(OC(C)(C)C)C(=O)O)c(C)nc4sc5c(c34)CCCC5)cc2s1] | 2.73 (n = 2) | 12.8 (n = 2) |
| 23 | 422 | 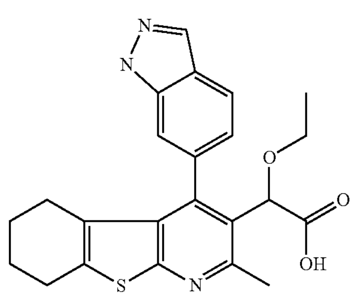 [SMILES: CCOC(C(=O)O)c1c(C)nc2sc3c(c2c1-c1ccc2cn[nH]c2c1)CCCC3] | 2.73 (n = 2) | 33.1 (n = 2) |

-continued

| Example | Mass | Structure | Antiviral Activity (S8737E, μM) | HTRF Interaction assay (S9118, μM) |
|---|---|---|---|---|
| 24 | 464 | 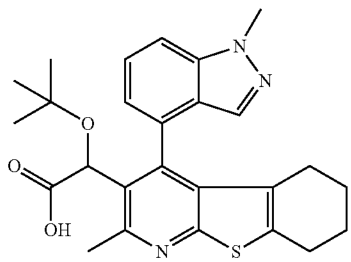 [SMILES: Cc1nc2sc3c(c2c(-c2cccc4c2cnn4C)c1C(OC(C)(C)C)C(=O)O)CCCC3] | 2.81 (n = 2) | 7.59 (n = 2) |
| 25 | 397 | 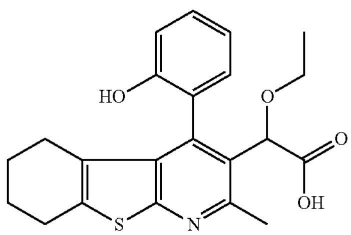 [SMILES: CCOC(C(=O)O)c1c(C)nc2sc3c(c2c1-c1ccccc1O)CCCC3] | 4.07 (n = 2) | >100 (n = 2) |
| 26 | 435 | 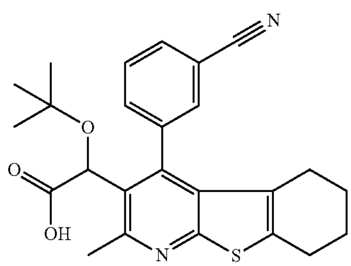 [SMILES: Cc1nc2sc3c(c2c(-c2cccc(C#N)c2)c1C(OC(C)(C)C)C(=O)O)CCCC3] | 4.51 (n = 2) | >100 (n = 2) |
| 27 | 440 | 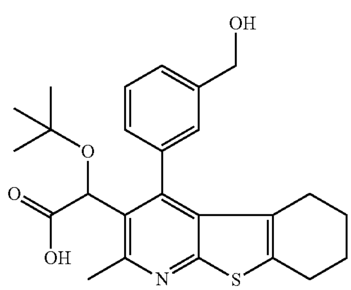 [SMILES: Cc1nc2sc3c(c2c(-c2cccc(CO)c2)c1C(OC(C)(C)C)C(=O)O)CCCC3] | 4.64 (n = 2) | 57.5 (n = 2) |
| 28 | 504 | 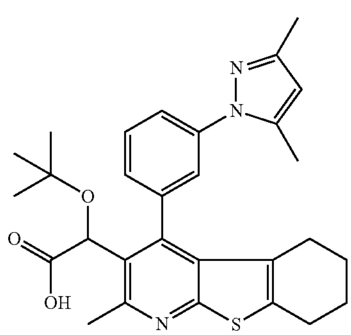 [SMILES: Cc1cc(C)n(-c2cccc(-c3c(C(OC(C)(C)C)C(=O)O)c(C)nc4sc5c(c34)CCCC5)c2)n1] | 5.61 (n = 2) | 29.6 (n = 2) |

-continued

| Example | Mass | Structure | Antiviral Activity (S8737E, μM) | HTRF Interaction assay (S9118, μM) |
|---|---|---|---|---|
| 29 | 454 | 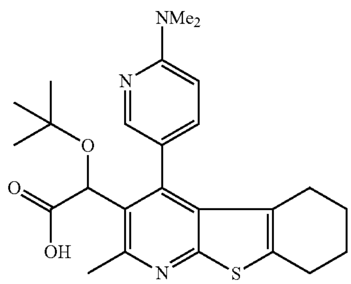 [SMILES: Cc1nc2sc3c(c2c(-c2ccc(N(C)C)nc2)c1C(OC(C)(C)C)C(=O)O)CCCC3] | 5.73 (n = 2) | 64.6 (n = 2) |
| 30 | 450 | 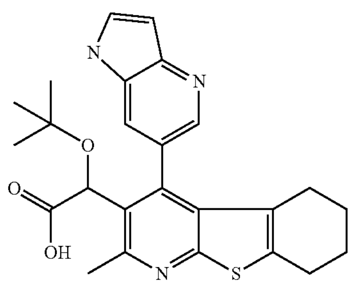 [SMILES: Cc1nc2sc3c(c2c(-c2cnc4cc[nH]c4c2)c1C(OC(C)(C)C)C(=O)O)CCCC3] | 6.63 (n = 2) | 15.5 (n = 2) |
| 31 | 439 | 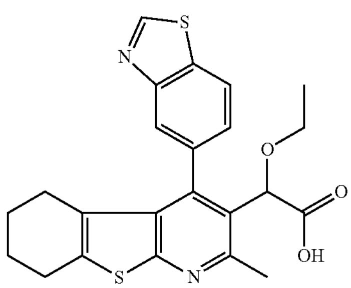 [SMILES: CCOC(C(=O)O)c1c(C)nc2sc3c(c2c1-c1ccc2scnc2c1)CCCC3] | 6.66 (n = 2) | >100 (n = 2) |
| 32 | 450 | 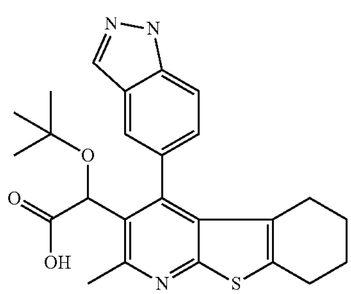 [SMILES: Cc1nc2sc3c(c2c(-c2ccc4[nH]ncc4c2)c1C(OC(C)(C)C)C(=O)O)CCCC3] | 7.65 (n = 2) | >100 (n = 2) |
| 33 | 450 | 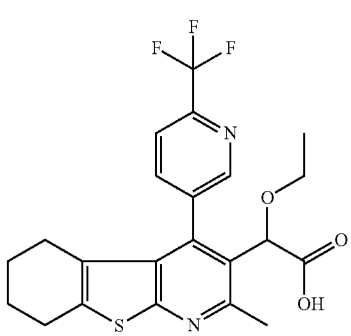 [SMILES: CCOC(C(=O)O)c1c(C)nc2sc3c(c2c1-c1ccc(C(F)(F)F)nc1)CCCC3] | 8.19 (n = 2) | >100 (n = 2) |

-continued

| Example | Mass | Structure | Antiviral Activity (S8737E, μM) | HTRF Interaction assay (S9118, μM) |
|---|---|---|---|---|
| 34 | 412 | 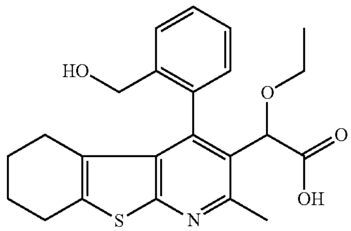 [SMILES: CCOC(C(=O)O)c1c(C)nc2sc3c(c2c1-c1ccccc1CO)CCCC3] | 8.97 (n = 2) | >100 (n = 2) |
| 35 | 436 | 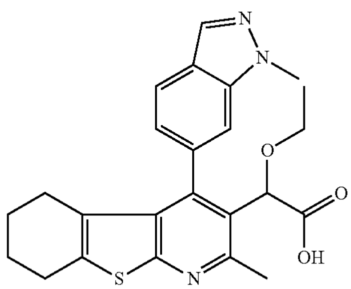 [SMILES: CCOC(C(=O)O)c1c(C)nc2sc3c(c2c1-c1ccc2cnn(C)c2c1)CCCC3] | 10.7 (n = 2) | >100 (n = 2) |
| 36 | 450 | 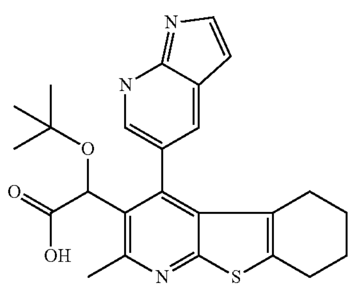 [SMILES: Cc1nc2sc3c(c2c(-c2c[nH]c4nccc-4c2)c1C(OC(C)(C)C)C(=O)O)CCCC3] | 12 (n = 2) | >100 (n = 2) |
| 37 | 425 | 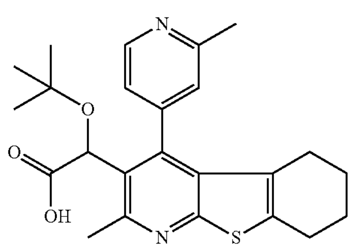 [SMILES: Cc1cc(-c2c(C(OC(C)(C)C)C(=O)O)c(C)nc3sc4c(c23)CCCC4)ccn1] | 13.9 (n = 2) | >100 (n = 2) |
| 38 | 476 | 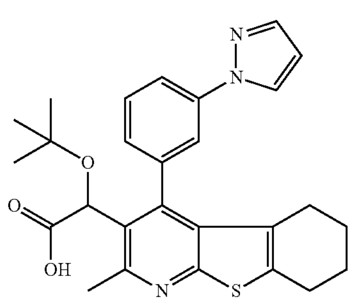 [SMILES: Cc1nc2sc3c(c2c(-c2cccc(-n4cccn4)c2)c1C(OC(C)(C)C)C(=O)O)CCCC3] | 15.1 (n = 2) | 97.5 (n = 2) |

-continued
| Example | Mass | Structure | Antiviral Activity (S8737E, μM) | HTRF Interaction assay (S9118, μM) |
|---|---|---|---|---|
| 39 | 442 | 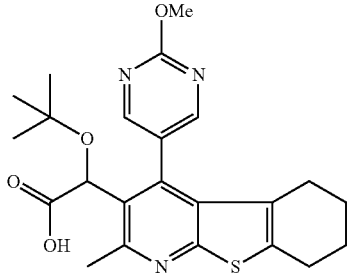 [SMILES: COc1ncc(-c2c(C(OC(C)(C)C)C(=O)O)c(C)nc3sc4c(c23)CCCC4)cn1] | 15.5 (n = 2) | >100 (n = 2) |
| 40 | 436 | 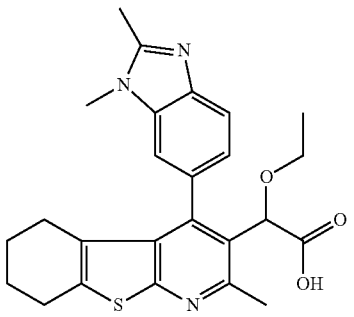 [SMILES: CCOC(C(=O)O)c1c(C)nc2sc3c(c2c1-c1ccc2nc(C)n(C)c2c1)CCCC3] | 15.7 (n = 2) | >100 (n = 2) |
| 41 | 400 | 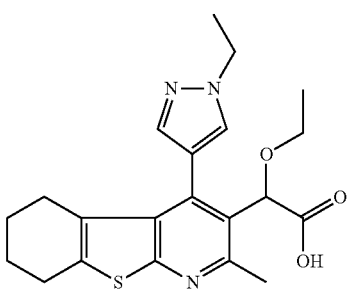 [SMILES: CCOC(C(=O)O)c1c(C)nc2sc3c(c2c1-c1cnn(CC)c1)CCCC3] | 17.7 (n = 2) | >100 (n = 2) |
| 42 | 413 | 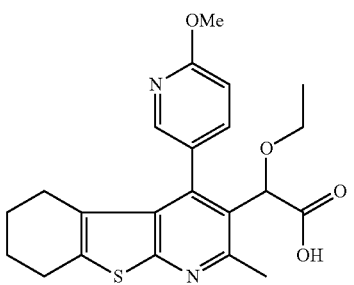 [SMILES: CCOC(C(=O)O)c1c(C)nc2sc3c(c2c1-c1ccc(OC)nc1)CCCC3] | 18.1 (n = 2) | >100 (n = 2) |
| 43 | 436 | 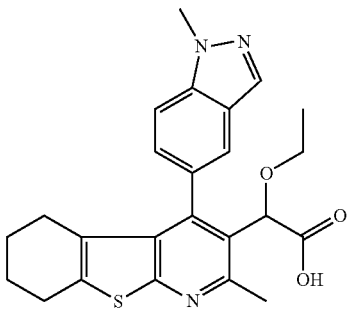 [SMILES: CCOC(C(=O)O)c1c(C)nc2sc3c(c2c1-c1ccc2c(cnn2C)c1)CCCC3] | 18.9 (n = 2) | >100 (n = 2) |

EXAMPLE 44

(2S)-tert-butoxy[4-(4-chlorophenyl)-2-methyl-5,6,7,8-tetrahydro[1]benzothieno[2,3-b]pyridin-3-yl]acetic acid

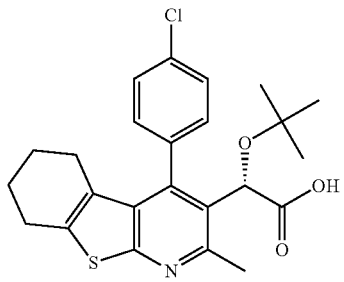 [SMILES: Cc1nc2sc3c(c2c(-c2ccc(Cl)cc2)c1[C@H](OC(C)(C)C)C(=O)O)CCCC3]

Step 1: Methyl (2S)-tert-butoxy[4-(4-chlorophenyl)-2-methyl-5,6,7,8-tetrahydro[1]benzothieno[2,3-b]pyridin-3-yl]acetate To a solution of Methyl (2S)-tert-butoxy(4-iodo-2-methyl-5,6,7,8-tetrahydro[1]benzothieno[2,3-b]pyridin-3-yl)acetate (Preparation 16, 100 mg, 212 μmol) in dioxane (2 mL) was added 4-chlorobenzene boronic acid (66 mg, 422 μmol), ethyl-di-isopropyl-amine (120 μL, 636 μmol), water (500 μL) and palladium tetrakis(triphenylphosphine) (25 mg, 20 μmol). The reaction mixture was degassed and stirred at 100° C. in a sealed tube. The reaction was cooled to room temperature and diluted with ethyl acetate (10 mL). The mixture was passed through a pad of Celite. The organic filtrate was washed with water (10 mL) and brine (10 mL), dried over MgSO₄ and concentrated in vacuo to yield the crude product. The residue was purified by flash chromatography eluting with ethyl acetate in heptane (0-6%) to give the title compound as a white semi-solid, 60 mg, in a 62% yield. ¹H NMR (400 MHz, CDCl₃) δ ppm 0.97 (s, 9 H), 1.45-1.48 (m, 1 H), 1.62-1.73 (m, 3 H), 1.78-1.82 (m, 2 H), 2.71 (s, 3 H), 2.78-2.81 (m, 2 H), 3.66 (s, 3 H), 4.99 (s, 1 H), 7.18-7.21 (m, 1H), 7.39-7.42 (m, 3H).

Step 2: (2S)-tert-butoxy[4-(4-chlorophenyl)-2-methyl-5,6,7,8-tetrahydro[1]benzothieno[2,3-b]pyridin-3-yl]acetic acid To a solution of Methyl (2S)-tert-butoxy[4-(4-chlorophenyl)-2-methyl-5,6,7,8-tetrahydro[1]benzothieno[2,3-b]pyridin-3-yl]acetate (60 mg, 131 μmol) in tetrahydrofuran (2 mL) and methylated spirit (2 mL) was added an aqueous sodium hydroxide solution (1 M, 790 μL, 790 μmol). The resulting solution was stirred at 60° C. for 3 hours. The volatile solvents were removed in vacuo and the residue diluted with water (10 mL). Dichloromethane (20 mL) was added to the mixture, which was then acidified to pH 5 by the addition of 2 M aqueous hydrochloric acid. The organic layer was separated and washed with water (10 mL) and brine (10 mL), dried over MgSO₄ and concentrated in vacuo. The residue was recrystallised from 2-propanol and the resulting solid collected by filtration to give the title compound as a white solid, 11.2 mg, in a 19% yield.

¹H NMR (400 MHz, CDCl₃) δ ppm 1.02 (s, 9 H), 1.45-1.48 (m, 1 H), 1.67-1.73 (m, 3 H), 1.78-1.84 (m, 2 H), 2.69 (s, 3 H), 2.79-2.81 (m, 2 H), 5.11 (s, 1 H), 7.18-7.22 (m, 1 H), 7.42-7.46 (m, 2 H), 7.59-7.61 (m, 1 H).

Antiviral Activity=0.036 μM (n=6) (S8737E).

HTRF Interaction assay=576 nM (n=10) (S9118)

EXAMPLE 45

(2S)-tert-butoxy[4-(4-chloro-2-fluorophenyl)-2-methyl-5,6,7,8-tetrahydro[1]benzothieno[2,3-b]pyridin-3-yl]acetic acid

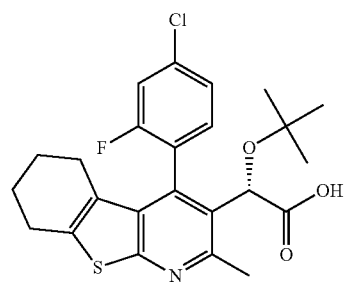 [SMILES: Cc1nc2sc3c(c2c(-c2ccc(Cl)cc2F)c1[C@H](OC(C)(C)C)C(=O)O)CCCC3]

Step 1: Methyl (2S)-tert-butoxy[4-(4-chloro-2-fluorophenyl)-2-methyl-5,6,7,8-tetrahydro[1]benzothieno[2,3-b]pyridin-3-yl]acetate The title compound was prepared from Methyl (2S)-tert-butoxy(4-iodo-2-methyl-5,6,7,8-tetrahydro[1]benzothieno[2,3-b]pyridin-3-yl)acetate (Preparation 16, 100 mg, 212 μmol) and (4-chloro-2-fluorophenyl) boronic acid (74 mg, 424 μmol) using the same method as described in Example 44, Step 1 to yield 57 mg, 56%. Material obtained was a mixture of atropisomers, in a 3:1 ratio. ¹H NMR (400 MHz, CDCl₃) δ ppm 1.01 (s, 9 H), 1.48-1.55 (m, 1 H), 1.69-1.75 (m, 3 H), 1.95-2.03 (m, 1 H), 2.72 (s, 3 H), 2.80-2.86 (m, 3 H), 3.66 (s, 3 H), 4.98 (s, 1 H), 7.19-7.21 (m, 1 H), 7.25-7.27 (m, 1 H), 7.35-7.37 (m, 1 H).

Step 2: (2S)-tert-butoxy[4-(4-chloro-2-fluorophenyl)-2-methyl-5,6,7,8-tetrahydro[1]benzothieno[2,3-b]pyridin-3-yl]acetic acid The title compound was prepared from Methyl (2S)-tert-butoxy[4-(4-chloro-2-fluorophenyl)-2-methyl-5,6,7,8-tetrahydro[1]benzothieno[2,3-b]pyridin-3-yl]acetate (57 mg, 119 μmol) using the same method as described in Example 44, Step 2. Purification by flash column chromatography, eluting with 5% methanol in dichloromethane gave the title compound, 24 mg, in a 24% yield. Material is a single atropisomer. The second atropisomer was not isolated. ¹H NMR (400 MHz, CDCl₃) δ ppm 1.04 (s, 9 H), 1.45-1.51 (m, 1 H), 1.62-1.76 (m, 3 H), 1.82-1.84 (m, 1 H), 2.05-2.10 (m, 1 H), 2.69 (s, 3 H), 2.80-2.84 (m, 2 H), 5.08 (s, 1 H), 7.22-7.28 (m, 2 H), 7.59-7.61 (m, 1 H).

Antiviral Activity=0.023 μM (n=6) (S8737E).

HTRF Interaction assay=565 nM (n=10) (S9118)

EXAMPLE 46

(2S)-tert-butoxy[4-(4-chloro-2-hydroxyphenyl)-2-methyl-5,6,7,8-tetrahydro[1]benzothieno[2,3-b]pyridin-3-yl]acetic acid

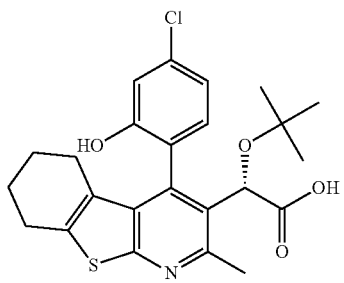 [SMILES: Cc1nc2sc3c(c2c(-c2ccc(Cl)cc2O)c1[C@H](OC(C)(C)C)C(=O)O)CCCC3]

Step 1: Methyl (2S)-tert-butoxy[4-(4-chloro-2-hydroxyphenyl)-2-methyl-5,6,7,8-tetrahydro[1]benzothieno[2,3-b]pyridin-3-yl]acetate To a solution of Methyl (2S)-tert-butoxy(4-iodo-2-methyl-5,6,7,8-tetrahydro[1]benzothieno[2,3-b]pyridin-3-yl)acetate (Preparation 16, 200 mg, 422 µmol) in dioxane (4 mL) was added (4-chloro-2-hydroxyphenyl) boronic acid (Preparation 17, 191 mg, 761 µmol), Dichloro [1,1'bis(di-tert-butylphosphino)]ferrocene palladium (II)™ (Pd-118) (Johnson-Matthey, 27 mg, 10 mol %, 42.2 µmol), potassium phosphate (180 mg, 844 µmol) and water (1 mL). The resulting mixture was stirred at 105° C. in a sealed tube for 18 hours. A further portion of Pd-118 (10 mg, 3.7 mol %, 15.6 µmol) was added and the mixture stirred at 105 C for 72 hours. The reaction mixture was cooled to room temperature and filtered through a short pad of silica, washing with ethyl acetate. The solvent was removed in vacuo. The crude product was purified by column chromatography eluting with ethyl acetate/heptane (0-10%) to yield the title compound as a brown solid, 37.5 mg, in a 19% yield. Material obtained was a mixture of atropisomers, in a ~2:1 ratio and was carried on to hydrolysis step 2 without further purification.

Step 2: (2S)-tert-butoxy[4-(4-chloro-2-hydroxyphenyl)-2-methyl-5,6,7,8-tetrahydro[1]benzothieno[2,3-b]pyridin-3-yl]acetic acid The title compound was prepared from Methyl (2S)-tert-butoxy[4-(4-chloro-2-hydroxyphenyl)-2-methyl-5,6,7,8-tetrahydro[1]benzothieno[2,3-b]pyridin-3-yl]acetate (70 mg, 148 µmol) using the same method as described in Example 44, Step 2. Purification by flash column chromatography, eluting with ethyl acetate, then with 20% methanol in ethyl acetate gave the separated atropisomers, 46A: 26 mg, in a 24% yield and 46B: 7 mg, in a 10% yield. 46A: $^1$H NMR (400 MHz, CD$_3$OD) δ ppm 1.02 (s, 9 H), 1.50-1.53 (m, 1 H), 1.65-1.98 (m, 4 H), 2.18-2.21 (m, 1 H), 2.64 (s, 3 H), 2.79-2.81 (m, 2 H), 5.13 (s, 1H), 6.91 (s, 1H), 6.97 (d, 1 H), 7.27 (d, 1 H). 48B: $^1$H NMR (400 MHz, CD$_3$OD) δ ppm 1.00 (s, 9 H), 1.49-1.51 (m, 1 H), 1.65-1.85 (m, 4 H), 2.20-2.26 (m, 1 H), 2.69 (s, 3 H), 2.79-2.81 (m, 2 H), 5.05 (s, 1 H), 6.88 (s, 1 H), 6.92 (d, 1 H), 7.40 (d, 1 H).

Atropisomer 46A: Antiviral activity=0.014 µM (n=2) (S8737E)

HTRF Interaction assay=558 nM (n=6) (S9118)

Atropisomer 48B: Antiviral Activity=0.040 µM (n=2) (S8737E).

HTRF Interaction assay=798 nM (n=2) (S9118)

EXAMPLE 47

(2S)-tert-butoxy[4-(2-fluoro-4-methylphenyl)-2-methyl-5,6,7,8-tetrahydro[1]benzothieno[2,3-b]pyridin-3-yl]acetic acid

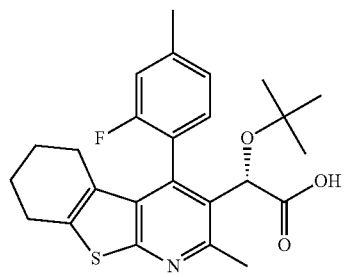 [SMILES: Cc1ccc(-c2c([C@H](OC(C)(C)C)C(=O)O)c(C)nc3sc4c(c23)CCCC4)c(F)c1]

Step 1: Methyl (2-tert-butoxy[4-(2-fluoro-4-methylphenyl)-2-methyl-5,6,7,8-tetrahydro[1]benzothieno[2,3-b]pyridin-3-yl]acetate The title compound was prepared from Methyl (2S)-tert-butoxy(4-iodo-2-methyl-5,6,7,8-tetrahydro[1]benzothieno[2,3-b]pyridin-3-yl)acetate (Preparation 16, 100 mg, 212 µmol) and 2-(2-fluoro-4-methylphenyl)-4,4,5,5-tetramethyl-1,3,2-dioxaborolane (Preparation 19, 99 mg, 424 µmol) using the same method as described in Example 44, Step 1 to yield 100 mg, 96%. Material obtained was a mixture of atropisomers, in a 2:1 ratio.

$^1$H NMR (400 MHz, CDCl$_3$) δ ppm 0.99 (s, 5.8 H), 1.05 (s, 3.2 H), 1.26-2.08 (m, 6 H), 2.45 (s, 3 H), 2.71 (s, 1.0 H), 2.76-2.80 (m, 2 H), 2.81 (as 1.2 H), 3.58 (s, 1.2 H), 3.66 (s, 1.8 H), 5.06 (s, 0.66 H), 5.07 (s, 0.33 H), 6.94-7.02 (m, 2.4 H), 7.23-7.25 (m, 0.6 H).

Step 2: (2S)-tert-butoxy[4-(2-fluoro-4-methylphenyl)-2-methyl-5,6,7,8-tetrahydro[1]benzothieno[2,3-b]pyridin-3-yl]acetic acid The title compound was prepared from Methyl (2S)-tert-butoxy[4-(2-fluoro-4-methylphenyl)-2-methyl-5,6,7,8-tetrahydro[1]benzothieno[2,3-b]pyridin-3-yl]acetate (100 mg, 220 µmol) using the same method as described in Example 44, Step 2. Purification by flash column chromatography, eluting with 5% methanol in dichloromethane failed to separate the atropisomers, and the mixture was still a 2:1 ratio of two atropisomers, 40 mg, 41%. $^1$H NMR (400 MHz, CDCl$_3$) δ ppm 0.95 (s, 5.8 H), 1.05 (s, 3.2 H), 1.26-2.08 (m, 6 H), 2.44 (s, 1.2 H), 2.45 (s, 1.8 H), 2.68 (s, 1.8 H), 2.75 (s, 1.2 H), 2.76-2.81 (m, 2 H), 5.05 (s, 0.66 H), 5.11 (s, 0.33 H), 7.02-7.13 (m, 2.4 H), 7.45-7.49 (m, 0.6 H).

Antiviral Activity=0.071 µM (n=2) (S0737E).

HTRF Interaction assay=657 nM (n=2) (S9118)

EXAMPLE 48
Tert-butoxy[4-(2-hydroxy-4-methylphenyl)-2-methyl-5,6,7,8-tetrahydro[1]benzothieno[2,3-b]pyridin-3-yl]acetic acid
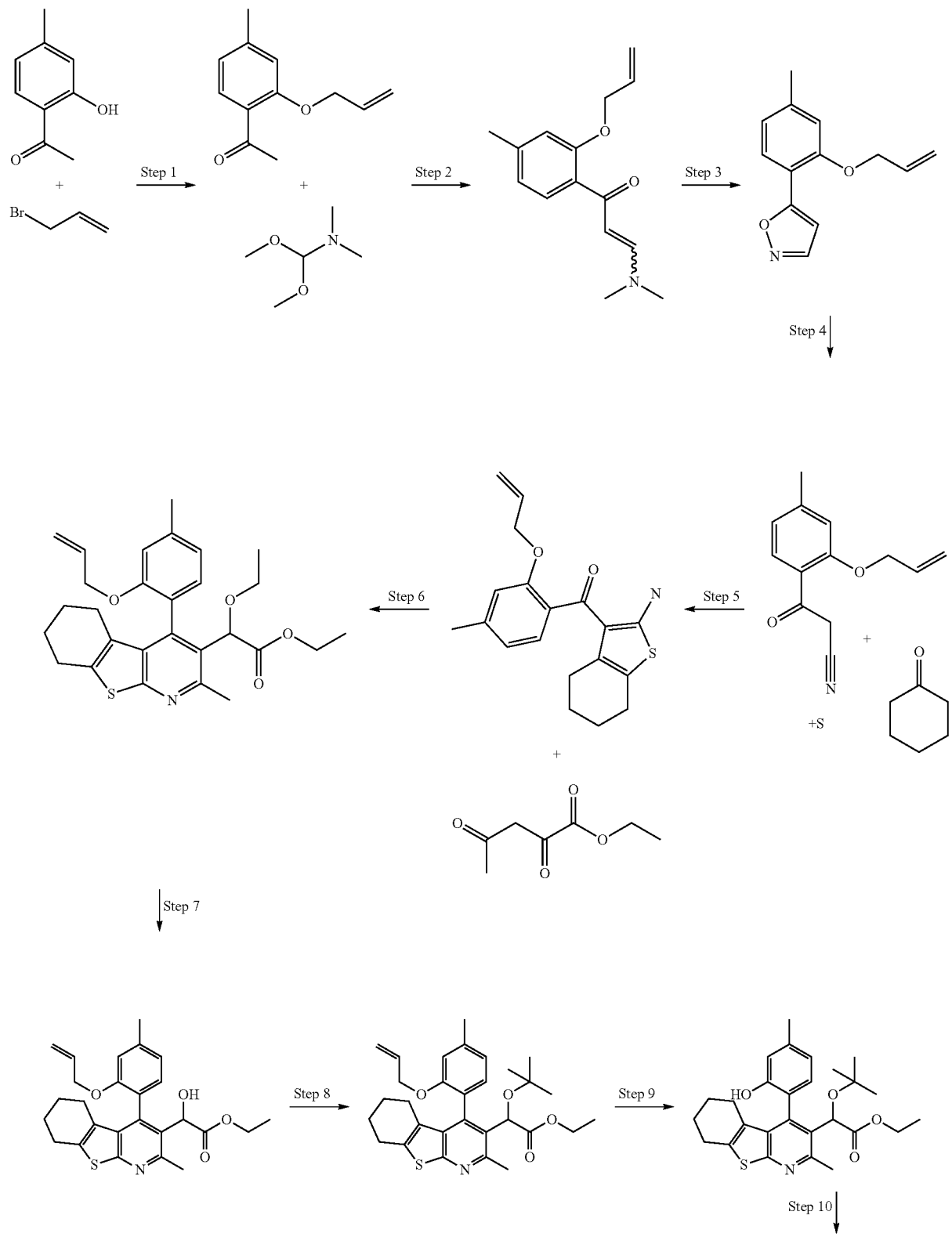

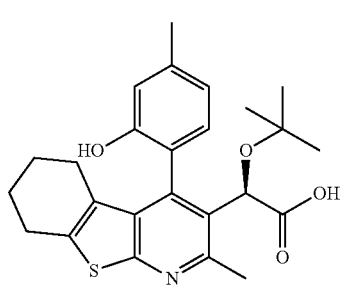 + 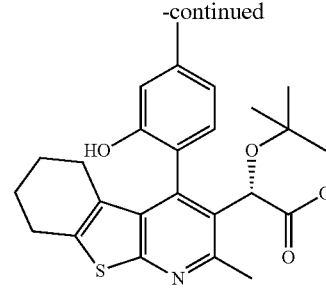 ← Step 11

Step 1: 1-[2-(allyloxy)-4-methylphenyl]ethanone

To a solution of 1-(2-hydroxy-4-methyl-phenyl)-ethanone (10 g, 67 mmol) in dimethylformamide (100 mL) was added potassium carbonate (18.4 g, 133 mmol), followed by allyl bromide (5.75 mL, 67 mmol). The reaction was stirred at room temperature for 16 hours. The residue was partitioned between ethyl acetate (200 mL) and water (800 mL), the organics were separated, and washed with brine (50 mL), dried over $MgSO_4$ and concentrated in vacuo. After cooling the concentrate to room temperature the title compound crystallised as colourless platelets, 12.40 g, in a 98% yield. LCMS (2 min acidic) 1.20 min 72-100% pure by UV, ES+/AP+ 191. $^1$HNMR (400 MHz, $CDCl_3$) δ ppm 2.37 (s, 3H), 2.63 (s, 3H), 4.61-4.66 (m, 2H), 5.33 (dq, 1H), 5.44 (dq, 1H), 6.10 (m, 1H), 6.76 (s, 1H), 6.80-6.83 (m, 1H), 7.68 (d, 1H).

Step 2: (2E)-1-[2-(allyloxy)-4-methylphenyl]-3-(dimethylamino)prop-2-en-1-one To 1-[2-(allyloxy)-4-methylphenyl]ethanone (Step 1, 13.9 g, 73 mmol) was added dimethylformamide dimethylacetal (56 mL, 422 mmol), and the reaction was heated to reflux for 18 hours. The reaction was then concentrated in vacuo to give the title compound as an orange oil, 17.9 g, which was taken crude into the next reaction.

Step 3: 5-[2-(allyloxy)-4-methylphenyl]isoxazole

To a stirred solution of crude (2E)-1-[2-(allyloxy)-4-methylphenyl]-3-(dimethylamino)prop-2-en-1-one (Step 2, 14.1 g, 57.5 mmol) in methanol (70 mL) was added hydroxylamine hydrochloride (4.4 g, 63 mmol) and the reaction was stirred at room temperature for 1 hour. Colourless needle crystals were filtered off and analysed and found to be the title compound, 7.3 g, in a 58% yield. LCMS (2 min acidic) 1.32 min 64-91% pure by UV, ES+/AP+ 216. $^1$HNMR (400 MHz, $CDCl_3$) δ ppm 2.40 (s, 3H), 4.67 (m, 2H), 5.35 (dq, 1H), 5.46 (dq, 1H), 6.05-6.20 (m, 1H), 6.77 (m, 1H), 6.82 (s, 1H), 6.88-6.92 (m, 1H), 7.88 (d, 1H).

Step 4: 3-[2-(allyloxy)-4-methylphenyl]-3-oxoropanenitrile

To a stirred suspension of 5-[2-(allyloxy)-4-methylphenyl]isoxazole (Step 3, 7.3 g, 33.8 mmol) in ethanol (40 mL) was added sodium ethoxide (21% solution in ethanol, 40 mL, 110 mmol) and the reaction was stirred at room temperature for 3 hours. The reaction was acidified to pH 2 with hydrochloric acid (2N, aqueous) and the solid was filtered off and air dried for 1 hour to give the title compound as an off-white solid, 4.8 g, in a 66% yield. LCMS (2 min acidic) 1.12 min 51-100% pure by UV, ES+/AP+ 216, ES-/AP- 214. $^1$HNMR (400 MHz, $CDCl_3$) δ ppm 2.41 (s, 3H), 4.08 (s, 2H), 4.67-4.70 (m, 2H), 5.37-5.50 (m, 2H), 6.13 (m, 1H), 6.79 (s, 1H), 6.88 (dd, 1H), 7.80 (d, 1H).

Step 5: [2-(allyloxy)-4-methylphenyl](2-amino-4,5,6,7-tetrahydro-1-benzothien-3-yl)methanone To a stirred solution of 3-[2-(allyloxy)-4-methylphenyl]-3-oxopropanenitrile (Step 4, 1 g, 4.6 mmol) in ethanol (20 ml) was added cyclohexanone (722 μL, 7 mmol) and sulfur (224 mg, 7 mmol), followed by morpholine (610 μL, 7 mmol) and the reaction was stirred overnight at 40° C. The reaction was concentrated in vacuo. The residue was purified using ISCO Companion with a Redisep silica gel 40 g cartridge and a gradient of heptane and ethyl acetate (0% to 40%). Fractions containing desired product were combined and concentrated in vacuo to give the title compound as a yellow gum, 1.1 g, in a 72% yield. LCMS (2 min acidic) 1.45 min 58-100% pure by UV, ES+/AP+ 328. $^1$HNMR (400 MHz, $CDCl_3$) δ ppm 1.44-1.51 (m, 2H), 1.64-1.71 (m, 2H), 1.78 (tt, 2H), 2.36 (s, 3H), 2.47 (tt, 2H), 4.52 (dt, 2H), 5.13-5.28 (m, 2H), 5.92 (m, 1H), 6.69 (s, 1H), 6.78 (dq, 1H), 6.91 (br s, 2H), 7.08 (d, 1H).

Step 6: Ethyl {4-[2-(allyloxy)-4-methylphenyl]-2-methyl-5,6,7,8-tetrahydro[1]benzothieno[2,3-b]pyridin-3-yl}(oxo)acetate hydrochloride salt To a stirred solution of [2-(allyloxy)-4-methylphenyl](2-amino-4,5,6,7-tetrahydro-1-benzothieno-3-yl)methanone (Step 5, 882 mg, 2.69 mmol) in ethanol (30 mL) was added ethyl 2,4-dioxopentanoate (378 μL, 2.69 mmol) followed by acetyl chloride (766 μL, 10.8 mmol), and was heated to 50° C. for 1 hour. The reaction was then concentrated in vacuo to give a mixture of diastereoisomers of the title compound as the hydrochloride salt, as a pale yellow oil, 1 g, in an 86% yield. LCMS (2 min acidic) 1.70 min 54-100% pure by UV, ES+/AP+ 450. $^1$HNMR (400 MHz, $CDCl_3$) δ ppm 1.12 (t, 3H), 1.55-1.70 (m, 2H), 1.78-1.89 (m, 2H), 1.92-2.08 (m, 2H), 2.43 (, 3H), 2.87-2.93 (m, 2H), 2.95 (s, 3H), 3.84-3.94 (m, 2H), 4.39-4.51 (m, 2H), 5.09-5.20 (m, 2H), 5.82 (m, 1H), 6.76 (s, 1H), 6.87 (d, 1H), 6.95 (d, 1H).

Step 7: Ethyl {4-[2-(allyloxy)-4-methylphenyl]-2-methyl-5,6,7,8-tetrahydro[1]benzothieno[2,3-b]pyridin-3-yl}(hydroxy)acetate To a stirred solution of ethyl {4-[2-(allyloxy)-4-methylphenyl]-2-methyl-5,6,7,8-tetrahydro[1]benzothieno[2,3-b]pyridin-3-yl}(oxo)acetate hydrochloride salt (Step 6, 1.1 g, 2.56 mmol) in ethanol (20 mL) was added sodium borohydride (145 mg, 3.84 mmol), and the reaction was stirred at room temperature for 5 minutes. The reaction was concentrated in vacuo, and the residue was partitioned between ethyl acetate (20 mL) and hydrochloric acid (aqueous, 1N, 30 mL). The organic layer was separated, washed with brine (10 mL), dried over MgSO$_4$, filtered and concentrated in vacuo to give a mixture of diastereoisomers of the title compound as a pale orange gum, 1.1 g, in a 91% yield. LCMS (2 min acidic) 1.53 min 52-81% pure by UV, ES+/AP+ 452. $^1$HNMR (400 MHz, CDCl$_3$ δ ppm 1.17-1.21 (m, 3H), 1.53-1.64 (m, 2H), 1.71-1.87 (m, 4H), 2.43 (s, 3H), 2.63 (s, 3H), 2.81 (t, 2H), 4.08-4.22 (m, 2H), 4.47-4.51 (m, 2H), 5.08-5.17 (m, 2H), 5.18 (s, 1H), 5.86 (m, 1H), 6.79 (s, 1H), 6.81-6.85 (m, 1H), 7.02 (d, 1H).

Step 8: Ethyl {4-[2-(allyloxy)-4-methylphenyl]-2-methyl-5,6,7,8-tetrahydro[1]benzothieno[2,3-b]pyridin-3-yl}(tert-butoxy)acetate To a stirred solution of ethyl {4-[2-(allyloxy)-4-methylphenyl]-2-methyl-5,6,7,8-tetrahydro[1]benzothieno[2,3-b]pyridin-3-yl}(hydroxy)acetate (Step 7, 720 mg, 1.59 mmol) in dichloromethane (2.5 mL) was added tert-butyl acetate (2.5 mL) followed by concentrated sulphuric acid (244 µL, 4.78 mmol) and the reaction was stirred at room temperature for 2 hours. The reaction mixture was quenched by addition of a 1 M aqueous sodium hydroxide solution until the solution was at pH 5. The volatile solvents were removed in vacuo, and the remaining aqueous layer was extracted with ethyl acetate (30 mL). The organic layer was washed with brine (10 mL), dried over MgSO$_4$ and concentrated in vacuo. The residue was purified using ISCO Companion with a Redisep silica gel 12 g cartridge and a gradient of heptane and ethyl acetate (0% to 40%). Product containing fractions were concentrated in vacuo to give a mixture of diastereoisomers of the title compound as a colourless oil, 370 mg, in a 45% yield. Material is shown to be a mixture of diastereomers, in an approximately 80:20 ratio.

Major diastereomer (~80%)
$^1$H NMR (400 MHz, CDCl$_3$) δ ppm 0.95 (s, 9 H) 1.19 (t, 3 H) 1.53-1.82 (m, 4 H) 1.89-1.99 (m, 2 H) 2.42 (s, 3 H) 2.70 (s, 3 H) 2.80 (m, 2 H) 4.11 (m, 2 H) 4.26-4.45 (m, 2 H) 4.94-5.04 (m, 2 H) 5.05 (s, 1 H) 5.70-5.80 (m, 1 H) 6.71 (s, 1 H) 6.80 (d, 1 H) 7.15 (d, 1 H).

Minor diastereomer (~20%)
$^1$H NMR (400 MHz, CDCl$_3$) δ ppm 1.00 (s, 9 H) 1.13 (t, 3 H) 1.53-1.82 (m, 4 H) 1.89-1.99 (m, 2 H) 2.42 (s, 3H) 2.70 (s, 3 H) 2.80 (m, 2 H) 4.11 (m, 2 H) 4.26-4.45 (m, 2 H) 4.94-5.04 (m, 2 H) 5.05 (s, 1 H) 5.70-5.80 (m, 1 H) 6.73 (s, 1 H) 6.78 (d, 1 H) 6.93 (d, 1 H).

Step 9: Ethyl tert-butoxy[4-(2-hydroxy-4-methylphenyl)-2-methyl-5,6,7,8-tetrahydro[1]benzothieno[2,3-b]pyridin-3-yl]acetate To a stirred solution of ethyl {4-[2-(allyloxy)-4-methylphenyl]-2-methyl-5,6,7,8-tetrahydro[1]benzothieno[2,3-b]pyridin-3-yl}(tert-butoxy)acetate (Step 8, 370 mg, 729 µmol) in dichloromethane (10 mL) was added 1,3-dimethylbarbituric acid (569 mg, 3.64 mmol), and the reaction was evacuated and filed with nitrogen. Palladium tetrakis(triphenylphosphine) (17 mg, 15 µmol) was added and the reaction was heated to reflux for 16 hours. Further palladium tetrakis(triphenylphosphine) (17 mg, 15 µmol) was added and the reaction was heated to reflux for a further 4 hours. The reaction was concentrated in vacuo and preabsorbed onto silica. The residue was purified using ISCO Companion with a Redisep silica gel 12 g cartridge and a gradient of heptane and ethyl acetate (0% to 20%). Product containing fractions were concentrated in vacuo to give the title compound as a pair of diastereoisomers as a colourless oil, 214 mg, in a 63% yield. The other pair of minor diastereoisomers co-eluted with unreacted starting material and were not isolated. LC-MS (12 min acidic) 6.89 mins 100% pure by UV, ES+/APCI+ 468, ES−/APCI− 466 $^1$H NMR (400 MHz, CDCl$_3$) δ ppm 1.01 (s, 9 H) 1.20 (t, 3 H) 1.62-1.85 (m, 4 H) 2.02-2.14 (m, 2 H) 2.41 (s, 3 H) 2.74 (s, 3 H) 2.78-2.85 (m, 2 H) 4.08-4.18 (m, 2 H) 5.14 (s, 1 H) 6.78 (s, 1 H) 6.82 (d, 1 H) 7.17 (d, 1 H).

Step 10: Tert-butoxy[4-(2-hydroxy-4-methylphenyl)-2-methyl-5,6,7,8-tetrahydro[1]benzothieno[2,3-b]pyridin-3-yl]acetic acid To a stirred solution of the major diastereoisomeric pair of ethyl tert-butoxy[4-(2-hydroxy-4-methylphenyl)-2-methyl-5,6,7,8-tetrahydro[1]benzothieno[2,3-b]pyridin-3-yl]acetate (Step 9, 214 mg, 458 µmol) in ethanol (5 mL) and tetrahydrofuran (5 mL) was added a solution of sodium hydroxide (2 N, aqueous, 2 mL, 2.75 mmol) and the reaction was stirred at 60° C. for 18 hours. The reaction was concentrated in vacuo until all organic solvents had been removed, the aqueous residue was then acidified with hydrochloric acid (2 N, aqueous) to pH 2. The precipitated solid was collected by filtration and washed with tert-butyl methyl ether (10 mL) and dried in vacuo to give a mixture of diastereoisomers of the title compound as a white solid, 76 mg, in a 38% yield. LC-MS (12 min acidic) 5.51 mins 81% pure by UV, ES+/APCI+ 440, ES−/APCI− 438. $^1$H NMR (400 MHz, CDCl$_3$) δ ppm 1.04 (s, 9 H) 1.66-1.88 (m, 4 H) 2.09-2.21 (m, 2 H) 2.40 (s, 3 H) 2.73 (s, 3 H) 2.82 (t, 2 H) 5.33 (s, 1 H) 6.78 (s, 1 H) 6.85 (d, 1 H) 7.36 (d, 1 H).

Step 11: Chiral Separation

The diastereomeric pair isolated in Step 10 was separated using a Chiralpak IC column, eluting with 70:30 Heptane:IPA at 18 mL per minute, and a total run time of 9 minutes. The first enantiomer eluted at 3.56 minutes and the second enantiomer eluted at 4.54 minutes, monitoring by UV.

The first eluting enantiomer was confirmed as (2R)-tert-butoxy[4-(2-hydroxy-4-methylphenyl)-2-methyl-5,6,7,8-tetrahydro[1]benzothieno[2,3-b]pyridin-3-yl]acetic acid.
Antiviral Activity=0.089 µM (n=2) (S8737E).
HTRF Interaction assay=4120 nM (n=2) (S9118)

The second eluting enantiomer was confirmed as (2S)-tert-butoxy[4-(2-hydroxy-4-methylphenyl)-2-methyl-5,6,7,8-tetrahydro[1]benzothieno[2,3-b]pyridin-3-yl]acetic acid with the atropisomeric configuration shown below (confirmed by X-ray structure):

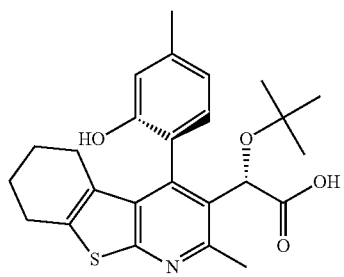

Antiviral Activity=0.013 µM (n=2) (S8737E).
HTRF Interaction assay=576 nM (n=2) (S9118)

EXAMPLE 49

Preparation of (S)-2-(tert-butoxy)-2-(4-(4-difluoromethyl)phenyl)-2-methyl-5,6,7,8-tetrahydrobenzo[4,5]thieno[2,3-b]pyridin-3-yl)acetic acid

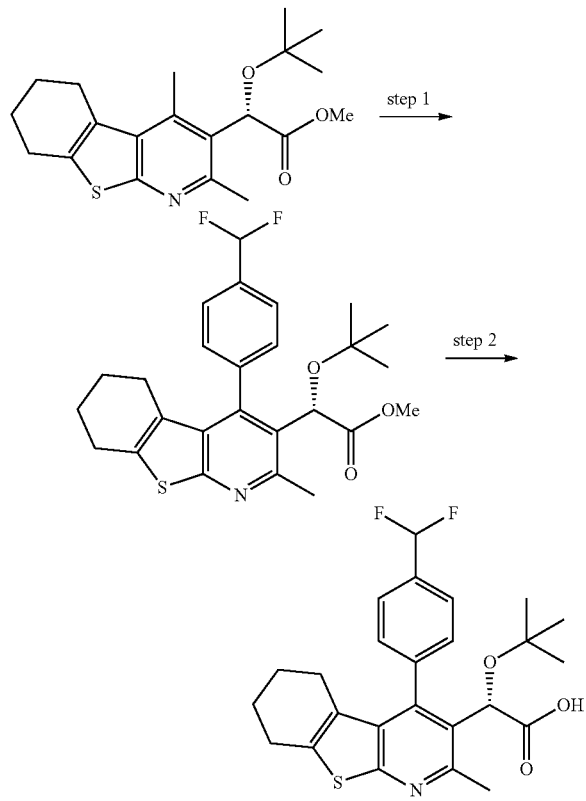

Step 1: (S)-methyl 2-(tert-butoxy-2-(4-(4-(difluoromethyl)phenyl)-2-methyl-5,6,7,8-tetrahydrobenzo[4,5]thieno[2,3-b]pyridin-3-yl)acetate 2-(4-(Difluoromethyl)phenyl)-4,4,5,5-tetramethyl-1,3,2-dioxaborolane (1.04 g, 4.09 mmol), potassium phosphate (1.35 g, 6.36 mmol), water (750 μL) and dichloro [1,1'bis(di-tert-butylphosphino)]ferrocene palladium (II)™ (101 mg, 155 μmol) were added to a stirred solution of (S)-methyl 2-(tert-butoxy)-2-(4-iodo-2-methyl-5,6,7,8-tetrahydrobenzo[4,5]thieno[2,3-b]pyridin-3-yl)acetate (750 mg, 1.58 mmol) in dioxane (11 mL) in a reaction tube. The reaction mixture was degassed with argon for 2 minutes, sealed and then stirred at 100° C. for 16 hours. The reaction mixture was cooled to room temperature, diluted with ethyl acetate (30 mL) and water (30 mL) and then passed through a pad of celite. The layers of the filtrate were separated and the aqueous layer was extracted with ethyl acetate (3×30 mL). The combined organic layers were dried (Na$_2$SO$_4$) and concentrated in vacuo to yield the crude product. The residue was purified by flash column chromatography-eluting with ethyl acetate in heptane (10%) to give the title compound (639 mg, 85%) as a yellow oil. $^1$H NMR (400 MHz, CDCl$_3$) δ=0.96 (s, 9H), 1.85-1.35 (m, 6H), 2.72 (s, 3H), 2.85-2.75 (m, 2H), 3.67 (s, 3H), 4.95 (s, 1H), 6.76 (t, 1H), 6.45 (d, 1H), 7.61-7.51 (m, 3H). LCMS (run time=5 minutes, basic): R$_t$=3.37 minutes; m/z 474.23 [M+H$^+$].

Step 2: (S)-2-(tert-butoxy)-2-(4-(4-(difluoromethyl)phenyl)-2-methyl-5,6,7,8-tetrahydrobenzo[4,5]thieno[2,3-b]pyridin-3-yl)acetic acid 2 M Aqueous sodium hydroxide solution (1.93 mL, 3.86 mmol) was added to a solution of (S)-methyl 2-(tert-butoxy)-2-(4-(4-(difluoromethyl)phenyl)-2-methyl-5,6,7,8-tetrahydro benzo[4,5]thieno[2,3-b]pyridin-3-yl)acetate (183 mg, 0.39 mmol) in 1:1 tetrohydrofuran/industrial methylated spirit (4 mL) at room temperature. The resulting mixture stirred at room temperature for 64 h. The reaction mixture was partitioned between ethyl acetate (20 mL) and water (10 mL). The aqueous solution was adjusted to pH 4 by the addition of 2 M aqueous hydrochloric acid solution. The layers were separated and the aqueous layer was extracted with ethyl acetate (2×10 mL). The combined organic layers were dried (MgSO$_4$) and concentrated in vacuo to give the crude product as a pale orange solid. This was purified by flash column chromatography on silica eluting with methanol in dichloromethane (3-5%) to give the title compound (111 mg, 63%) as an off-white solid. $^1$H NMR (400 MHz, CDCl$_3$) δ=1.01 (s, 9H), 1.90-1.35 (m, 6H), 2.70 (s, 3H), 2.85-2.78 (m, 2H), 5.07 (brs, 1H), 6.75 (t, 1H), 7.34-7.41 (brm, 1H), 7.61 (d, 2H), 7.80-7.70 (brm, 1H). LCMS (run time=5 minutes, basic): R$_t$=3.04 minutes; m/z 460.22 [M+H$^+$].

Antiviral Activity=0.081 μM (n=6) (S8737E).

HTRF Interaction assay=11010 nM (n=6) (S9118)

EXAMPLE 50

Preparation of (S)-2-(tert-butoxy)-2-(2-methyl-4-(4-(trifluoromethyl)phenyl)-5,6,7,8-tetrahydrobenzo[4.5]thieno[2,3-b]pyridin-3-yl)acetic acid

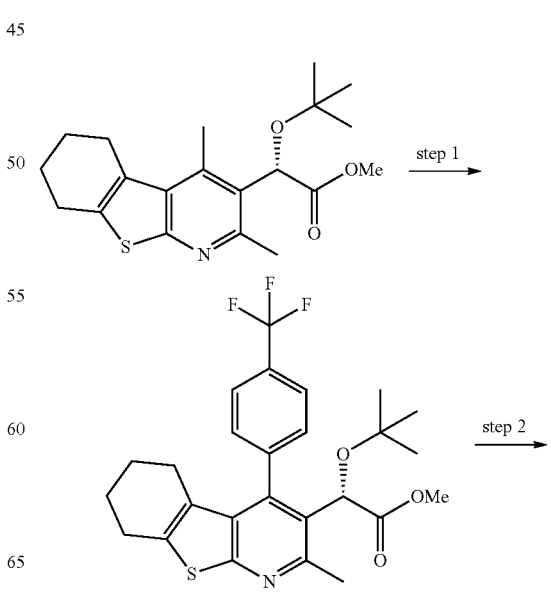

-continued

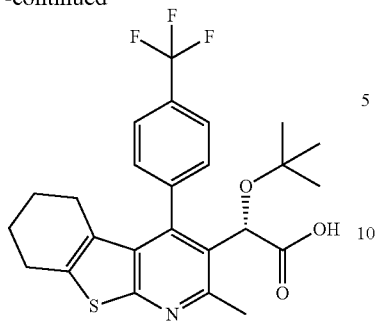

Step 1: (S)-methyl 2-(tert-butoxy)-2-(2-methyl-4-(4-(trifluoromethyl)phenyl)-5,6,7,8-tetrahydrobenzo[4,5]thieno[2,3-b]pyridin-3-yl)acetate 2-(4-(Trifluoromethyl)phenyl)-4,4,5,5-tetramethyl-1,3,2-dioxaborolane (115 g, 0.42 mmol), N-ethyl-N-isopropylpropan-2-amine (120 µL, 0.64 mmol) and water (500 µL) were added to a stirred solution of (S)-methyl 2-(tert-butoxy)-2-(4-iodo-2-methyl-5,6,7,8-tetrahydrobenzo[4,5]thieno[2,3-b]pyridin-3-yl)acetate (100 mg, 0.21 mmol) in dioxane (2 mL) in a reaction tube. The reaction mixture was degassed with argon for 2 minutes, then tetrakis(triphenylphosphine)palladium(0) (25 mg, 21 µmol) was added and the vessel was sealed and heated at 100° C. for 16 hours. The reaction mixture was cooled to room temperature and diluted with ethyl acetate (30 mL) and water (30 mL) and the mixture was passed through a pad of celite. The layers of the filtrate were separated and the organic layer was washed with brine (30 mL), dried (MgSO$_4$) and concentrated in vacuo to yield the crude product as a brown gum. The residue was purified by flash column chromatography eluting with ethyl acetate in heptane (10%) to give the title compound (75 mg, 72%) as a yellow oil. $^1$H NMR (400 MHz, CDCl$_3$) δ=0.96 (s, 9H), 1.85-1.35 (m, 6H), 2.72 (s, 3H), 2.85-2.75 (m, 2H), 3.69 (s, 3H), 4.91 (s, 1H), 7.40 (d, 1H), 7.61 (d, 1H), 7.71 (m, 2H). LCMS (run time=5 minutes, basic): R$_t$=3.64 minutes; m/z 492.06 [M+H$^+$].

Step 2: (S)-2-(tert-butoxy)-2-(2-methyl-4-(4-(trifluoromethyl)phenyl)-5,6,7,8-tetrahydrobenzo[4,5]thieno[2,3-b]pyridin-3-yl)acetic acid 1 M Aqueous sodium hydroxide solution (1.6 mL, 1.6 mmol) was added to a solution of (S)-methyl 2-(tert-butoxy)-2-(2-methyl-4-(4-(trifluoromethyl)phenyl)-5,6,7,8-tetrahydro benzo[4,5]thieno[2,3-b]pyridin-3-yl)acetate (75 mg, 0.15 mmol) in 1:1 tetrahydrofuran/industrial methylated spirit (4 mL) at room temperature. The resulting mixture was heated at 60° C. 1.5 h. The resulting solution was concentrated in vacuo and the residue was dissolved in water (10 mL). The aqueous solution was adjusted to pH 4 by the addition of 2 M aqueous hydrochloric acid solution and the resulting suspension was extracted with dichloromethane (20 mL). The organic layer was washed with brine, dried (MgSO$_4$) and concentrated in vacuo to give the crude product as a pale yellow solid. This was purified by flash column chromatography on silica eluting with methanol in dichloromethane (5%) to give the title compound (40.3 mg, 56%) as a pale yellow solid. $^1$H NMR (400 MHz, CDCl$_3$) δ=1.01 (s, 9H), 1.89-1.30 (m, 6H), 2.71 (s, 3H), 2.90-2.75 (m, 2H), 5.02 (s, 1H), 7.48-7.34 (m, 1H), 7.90-7.64 (m, 3H). LCMS (run time=5 minutes, basic): R$_t$=3.30 minutes; m/z 478.01 [M+H$^+$].

Antiviral Activity=0.055 µM (n=4) (S8737E).
HTRF Interaction assay=1500 nM (n=4) (S9118)

EXAMPLE 51

Preparation of (S)-2-(4-(4-bromophenyl)-2-methyl-5,6,7,8-tetrahydrobenzo[4,5]thieno[2,3-b]pyridin-3-yl)-2-(tert-butoxy)acetic acid

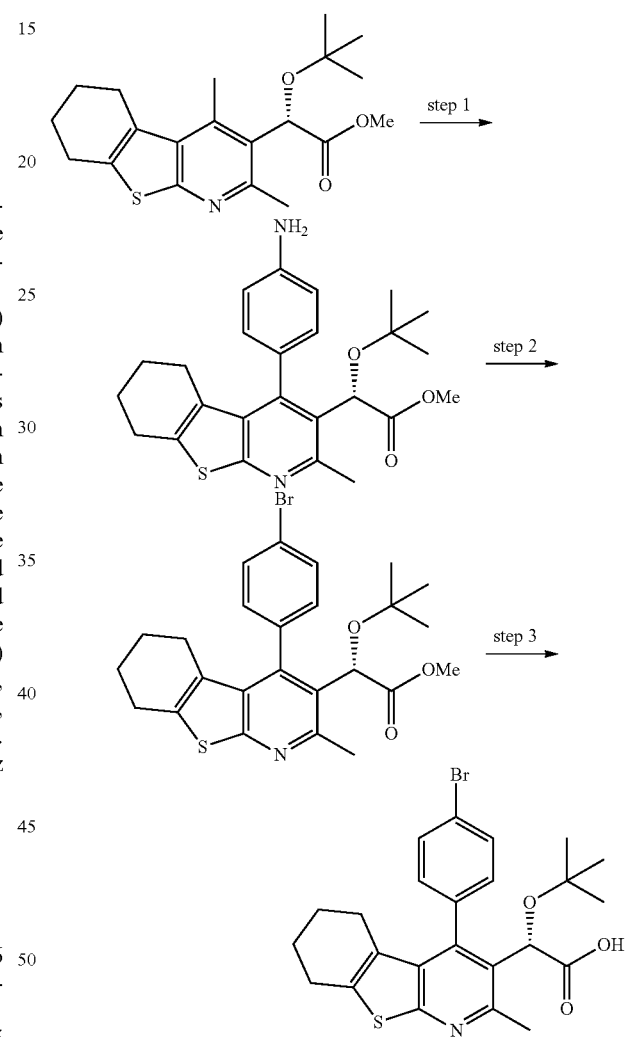

Step 1: (S)-methyl 2-(4-(4-aminophenyl)-2-methyl-5,6,7,8-tetrahydrobenzo[4,5]thieno[2,3-b]pyridin-3-yl)-2-(tert-butoxy)acetate 4-(4,4,5,5-Tetramethyl-1,3,2-dioxaborolan-2-yl)aniline (140 mg, 0.63 mmol), sodium hydrogen carbonate (178 mg, 2.1 mmol) and water (200 µL) were added to a stirred solution of (S)-methyl 2-(tert-butoxy)-2-(4-iodo-2-methyl-5,6,7,8-tetrahydrobenzo[4,5]thieno[2,3-b]pyridin-3-yl)acetate (200 mg, 0.42 mmol) in N,N-dimethylacetamide (4 mL) in a reaction tube. The reaction mixture was degassed with argon for 2 minutes, then bis(tri-tert-butylphosphine)

palladium(0) (22 mg, 42 µmol) was added and the vessel was sealed and heated at 100° C. for 16 hours. The reaction mixture was cooled to room temperature and partitioned between dichloromethane (30 mL) and water (30 mL). The layers were separated and the organic layer was dried (MgSO$_4$) and concentrated in vacuo to yield the crude product as a brown gum. The residue was purified by flash column chromatography on silica eluting with ethyl acetate in heptane (25%) to give the title compound (114 mg, 67%) as a white foam. $^1$H NMR (400 MHz, CDCl$_3$) δ 0.97 (s, 9H), 1.95-1.30 (m, 6H), 2.68 (s, 3H), 2.85-2.77 (m, 2H), 3.65 (s, 3H), 3.80 (brs, 2H), 5.19 (s, 1H), 6.75-6.68 (m, 2H), 6.99 (d, 1H), 7.19 (d, 1H).

Step 2: (S)-methyl 2-(4-(4-bromophenyl)-2-methyl-5,6,7,8-tetrahydrobenzo[4,5]thieno[2,3-b]pyridin-3-yl)-2-(tert-butoxy)acetate A solution of copper(II)bromide (73 mg, 0.33 mmol) and tert-butylnitrite (60 µL, 0.43 mmol) in acetonitrile (2 mL) was added to a stirred solution of (S)-methyl 2-(4-(4-aminophenyl)-2-methyl-5,6,7,8-tetrahydrobenzo[4,5]thieno[2,3-b]pyridin-3-yl)-2-(tert-butoxy)acetate (114 mg, 0.26 mmol) in acetonitrile (1 mL) at room temperature and the resulting mixture stirred at room temperature for 16 hours. The mixture was partitioned between 2 M aqueous hydrochloric acid solution (5 mL) and dichloromethane (10 mL) were added. The layers were separated and the organic layer was washed with water (10 mL), brine (10 mL), dried (MgSO$_4$) and concentrated in vacuo to give the crude product. This was purified by flash column chromatography on silica eluting with ethyl acetate in hepetene (10%) to give the title compound (83 mg, 63%) as brown oil. $^1$H NMR (400 MHz, CDCl$_3$) δ=0.96 (s, 9H), 1.85-1.40 (m, 6H), 2.71 (S, 3H), 2.81-2.75 (m, 2H), 3.65 (s, 3H), 4.99 (s, 1H), 7.12 (s, 1H), 7.31 (d, 1H), 7.60-7.50 (m, 2H). LCMS (run time=5 minutes, basic): R$_f$=3.57 minutes; m/z 504.12 [M+H$^+$].

Step 3: (S)-2-(4-(4-bromophenyl)-2-methyl-5,6,7,8-tetrahydrobenzo[4,5]thieno[2,3-b]pyridin-3-yl)-2-(tert-butoxy)acetic acid 1 M Aqueous sodium hydroxide solution (1.6 mL, 1.6 mmol) was added to a solution of (S)-methyl 2-(4-(4-bromophenyl)-2-methyl-5,6,7,8-tetrahydrobenzo[4,5]thieno[2,3-b]pyridin-3-yl)-2-(tert-butoxy)acetate (83 mg, 0.16 mmol) in 1:1 tetrahydrofuran/industrial methylated spirit (4 mL) at room temperature. The resulting mixture was heated to 60° C. and stirred at 60° C. 2 hours. The resulting solution was concentrated in vacuo and the residue was dissolved in water (10 mL). The aqueous solution was adjusted to pH 5 by the addition of 2 M aqueous hydrochloric acid solution and the resulting suspension was extracted with dichloromethane (20 mL). The organic layer was washed with brine, dried (MgSO$_4$) and concentrated in vacuo to give the crude product as a pale yellow solid. This was purified by trituration with industrial methylated spirit (5 mL). The resulting solid was collected by filtration to give the title compound (27 mg, 34%) as a white solid. $^1$H NMR (400 MHz, CDCl$_3$) δ=1.02 (s, 9H), 2.00-1.40 (m, 6H), 2.69 (s, 3H), 2.83-2.70 (m, 2H), 5.11 (s, 1H), 7.25-7.06 (m, 1H), 7:63-7.42 (m, 3H). LCMS (run time=5 minutes, basic): R$_f$=3.19 minutes; m/z 490.00 [M+H$^+$].

Antiviral Activity=0.080 µM (n=2) (S8737E).
HTRF Interaction assay=1160 nM (n=2) (S9118)

EXAMPLE 52

Tert-Butoxy-(2-methy-4-p-tolyl-5,8-dihydro-6H-7-oxa-9-thia-1-aza-fluoren-3-yl)-acetic acid

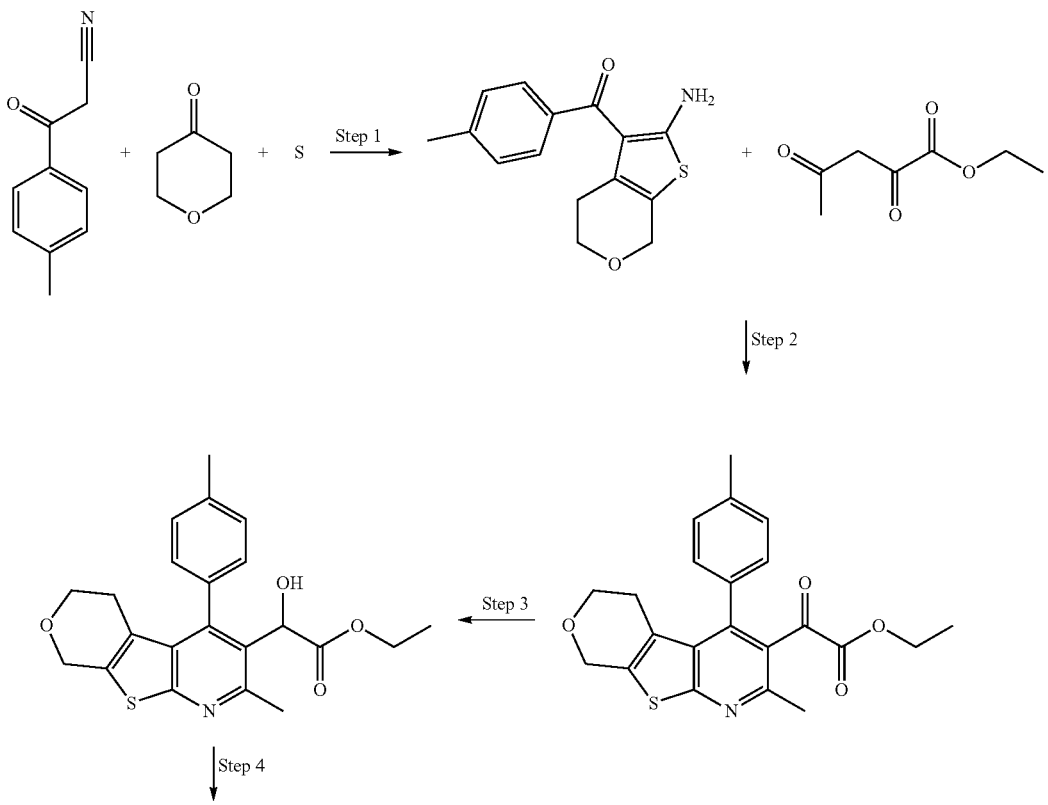

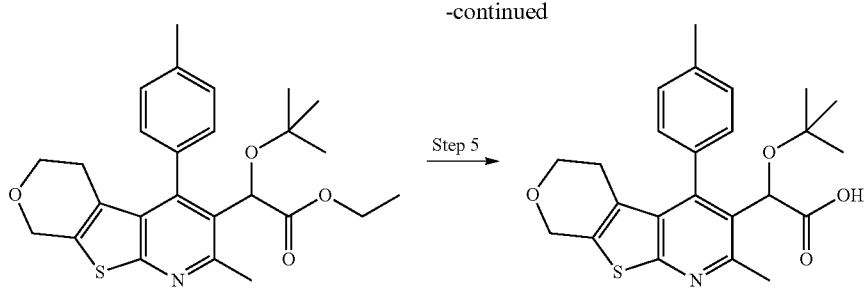

Step 1: (2-Amino-4,7-dihydro-5H-thieno[2,3-c]pyran-3-yl)-p-tolyl-methanone

4-Pyranone (2.31 mL, 24.97 mmol) and sulphur (801 mg, 24.97 mmol) were added to a solution of 3-oxo-3-p-tolyl-propionitrile (3.79 g, 23.8 mmol) in ethanol (40 mL) followed by morpholine (2.18 mL, 24.97 mmol) and the reaction heated at 40° C. for 16 hours, The reaction mixture was concentrated in vacuo and the residue purified by flash chromatography on silica eluting with 0-20% ethylacetate/heptanes to afford (2-Amino-4,7-dihydro-5H-thieno[2,3-c]pyran-3-yl)-p-tolyl-methanone as a yellow solid (2.2 g, 36% yield). LCMS (2 min acidic) 1.07 min ES+/AP+ 274 (MH+). $^1$HNMR (400 MHz, CDCl$_3$) δ ppm 2.00-2.03 (m, 2H), 2.42 (s, 3H), 3.80-3.84 (m, 2H), 4.80 (s, 2H), 6.60 (br s, 2H), 7.20 (d, 2H), 7.41 (d, 2H).

Step 2: (2-Methyl-4-p-tolyl-5,8-dihydro-6H-7-oxa-9-thia-1-aza-fluoren-3-yl)-oxo-acetic acid ethyl ester 2,4-Dioxo-pentanoic acid ethyl ester (1.2 mL, 8.6 mmol) was added to a solution of 2-Amino-4,7-dihydro-5H-thieno[2,3-c]pyran-3-yl)-p-tolyl-methanone (2.3 g, 8.6 mmol) in ethanol (50 mL) followed by acetyl chloride (2.43 mL, 34.3 mmol) and the reaction was warmed to 50° C. for 1 hour. The reaction was then concentrated in vacuo and preadsorbed onto silica. The residue was purified by flash chromatography on silica eluting with 0-40% ethyl acetate in heptanes to give the title compound as a red solid (675 mg, 19%). LCMS (2 min acidic) 2.78 mins ES+/AP+ 396 (MH+).

Step 3: Hydroxy-(2-methyl-4-p-tolyl-5,8-dihydro-6H-7-oxa-9-thia-1-aza-fluoren-3-yl)-acetic acid ethyl ester Sodium borohydride (97 mg, 2.56 mmol) was added to a stirred solution of hydroxy-(2-methyl-4-p-tolyl-5,8-dihydro-6H-7-oxa-9-thia-1-aza-fluoren-3-yl)-acetic acid ethyl ester (675 mg, 1.71 mmol) in ethanol (20 mL). 2M HCl in water (3 mL) was added and then the reaction mixture concentrated in vacuo. The residue was partitioned between water (50 mL) and ethyl acetate (30 mL). The layers were separated and the organics were dried (MgSO$_4$) and concentrated in vacuo to afford the title compound as a cream solid (543 mg, 80%) used without further purification. LCMS (2 min acidic) 1.20 min ES+/AP+ 398. $^1$HNMR (400 MHz, CDCl$_3$) δ ppm 1.20 (t, 3H), 1.82-1.88 (m, 2H), 2.41 (s, 3H), 2.61 (5, 3H), 3.68-3.72 (m, 2H), 4.10-4.21 (m, 2H), 4.81 (s, 2H), 7.16-7.26 (m, 4H).

Step 4: tert-Butoxy-(2-methyl-4-p-tolyl-5,8-dihydro-6H-7-oxa-9-thia-1-aza-fluoren-3-yl)-acetic acid ethyl ester Tert-Butyl acetate (0.8 mL) was added to a solution of hydroxy-(2-methyl-4-p-tolyl-5,8-dihydro-6H-7-oxa-9-thia-1-aza-fluoren-3-yl)-acetic acid ethyl ester (100 mg, 0.252 mmol) in dichloromethane (0.8 mL) followed by concentrated sulphuric acid (40 µL) and the reaction stirred at room temperature for 2 hours. Sodium bicarbonate solution (10% aqueous, 2 mL) was added and the reaction evaporated in vacuo until only the aqueous remained. The aqueous was extracted with ethyl acetate (2 mL) and the organic layer washed with brine (1 mL), dried and concentrated in vacuo. The residue was purified by flash chromatography on silica eluting with 0-30% ethyl acetate/heptanes to afford a colourless solid (66 mg, 45%). LCMS (12 min acidic) 7.25 min, ES+/AP+ 454 (MH+) $^1$HNMR (400 MHz, CDCl$_3$) δ ppm 0.98 (s, 9H), 1.20 (t, 3H), 1.55-1.65 (m, 2H), 2.43 (s, 3H), 2.77 (s, 3H), 3.57-3.61 (m, 1H), 3.78-3.82 (m, 1H), 4.06-4.20 (m, 2H), 4.79-4.82 (m, 2H), 7.16 (d, 2H), 7.32 (d, 2H).

Step 5: tert-Butoxy-(2-methyl-4-p-tolyl-5,8-dihydro-6H-7-oxa-9-thia-1-aza-fluoren-3-yl)-acetic acid Aqueous sodium hydroxide (2N, 2 mL, 4 mmol) was added to a stirred solution of tert-Butoxy-(2-methyl-4-p-tolyl-5,8-dihydro-6H-7-oxa-9-thia-1-aza-fluoren-3-yl)-acetic acid ethyl ester (66 mg, 0.15 mmol) in ethanol (2 mL) and tetrahydrofuran (2 mL) and the reaction was stirred for 2 hours at 60° C. The reaction was concentrated in vacuo until only the aqueous remained. The pH was adjusted to 2 by the addition of 2N aqueous HCl. The resulting solid was collected by filtration and purified by preparative HPLC to afford the title compound. LCMS 3.63 min, ES+/AP+ 425.1 (MH+).

Column: Gemini-NX 3 µm C18 110A, ambient temperature; detection: UV 225 nm—MS

Flow rate: 1.5 mL/min; mobile phase: A: H$_2$O+0.1% formic acid, B: MeCN +0.1% formic acid. Gradient (Time/mins, % B)—(0,5), (3,95), (4,95), (4,1,5), (5,5)

Antiviral Activity=0.189 µM (n=2) (S8737E).

HTRF Interaction assay=2750 nM (n=2) (S9118)

Evaluation of the Anti-HIV Activity of the Compounds of the Invention

MT-2 Based Antiviral Assay (S8737E)

This assay is designed to determine the effects of small molecules on the replication of HIV-1 in the lymphobastoid cell line, MT2, and is able to detect the antiviral effect of compounds acting at any stage of the HIV-1 replication cycle. The assay, along with its associated cytotoxicity assay, was described in detail in 2005 in a paper by Cao et al (Antimicrobial Agents and Chemotherapy 2005; 49(9), p 3833-3841).

MT2 cells are infected with the HIV-1 virus (NL4.3 strain; Adachi et al., Journal of Virology 1986) and transferred to assay plates containing serial dilutions of compounds to be tested. The assay plates are incubated for 3 days (MT2) to allow for several rounds of viral replication/infection to take place. At the end of this time, supernatant is transferred into new plates containing JC53BL cells.

JC53BL cells express CXCR4, CCR5 and CD4 receptors, and HIV-1-LTR-β-Gal. Under normal culture conditions undetectable levels of β-Galactosidase are expressed, but in the presence of HIV-1, the viral Tat protein is able to activate the HIV-1-LTR in the JC53BL cells resulting in the increased expression of the β-Gal enzyme. The expression can be measured using the 'FluorAce β-Galactosidase reporter' assay. The levels of β-Gal are directly proportional to the levels of Tat (up to a threshold) allowing virus quantification. Compounds that inhibit virus replication will give rise to a reduced signal and a dose-response curve for each compound can be generated. This is then used to determine the IC50 for each compound, a measure of the compound's potency.

The MT-2 based antiviral assay requires a separate cytotoxicity assessment of the compounds. This was performed using a 3 day MT-2 cytotoxicity assay as follows:

3 Day MT2 Cytotoxicity Assay (S8738E)

The assay is designed to test whether or not compounds have cytotoxic activity in MT2 cells by measuring the viability of these cells in the presence of compounds. The assay is carried out by adding MT2 assay plates containing serial dilutions of the compounds to be screened. After 3 days incubation, the viability of the cells remaining in the plates is assayed using the commercially available reagent CellTiter-Glo (Promega Ltd). The data generated is then used to calculate the concentration of compound required to cause 50% cytotoxcity (CC50).

All examples had CC50>20 µM.

References:
Adachi, A., Gendelman, H., Koenig, S., Folks, T., Wiley, R., Rabson, A. and Martin, M (1986) Production of acquired immunodeficency syndrome-associated retrovirus in human and nonhuman cells transfected with an infectious molecular clone, *J. Virol.*, 59, 284-291.

Cao J, Isaacson J, Patick A K, Blair W S. (2005) High-throughput human immunodeficiency virus type 1 (HIV-1) full replication assay that includes HIV-1 Vif as an antiviral target Antimicrobial Agents and Chemotherapy; 49(9), p 3833-3841.

Assay to Measure the LEDGF-Integrase Integration Inhibitory Activity of Compounds of the Invention HTRF Interaction Assay (S9118)

An Homogeneous Time Resolved Fluorescence (HTRF) assay is performed in a manner similar to previous reports on HTRF protein assays as reviewed by Mathis (Clin. Chem., 2005). The assay procedure is performed as follows: reactions are performed in 20 µl final volume in 384-well black low volume microtiter plates (Greiner). The final reaction buffer contains 29 mM phosphase buffer (pH 7), 10 mM HEPES buffet (pH 7.4), 68.5 mM NaCl, 1.4 mM KCl, 400 mM KF 0.05% (w/v) pluronic acid (P104, Sigma Aldrich) and 1% (v/v) DMSO. $His_6$-tagged integrase (78 nM final concentration) is incubated with mannose binding protein fused to the Δ325 carboxy terminal integrase binding domain of LEDGF in the presence of compound for 2 hours at room temperature. Both these protein regents are supplied by Prof. Zeger Debyser of Katholleke Universiteit Leuven, Leuven, Belgium. The compounds are added at varying concentrations spanning a wide range from 0.1 up to 100 µM. Afterwards 8.3 nM of europium cryptate conjugated anti-MBP monoclonal antibody and 17 nM anti-His antibody conjugated with the acceptor fluorophore d2. Following a 2 hour room temperature incubation the plates are read on an EnVision™ microplate reader (Perkin Elmer) using an excitation wavelength of 320 nM. The ratio of fluorescence emitted at 665 nM and 620 nM is used to assess the degree to which the protein-protein interaction had been inhibited.

References:
Mathis G., Probing molecular interactions with homogeneous techniques based on rare earth cryptates and fluorescence energy transfer. Clin. Chem. 41 (9), 1391-7 (1995).

What is claimed is:
1. A compound of the formula:

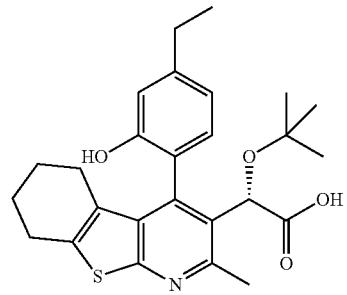 [SMILES: CCc1ccc(-c2c([C@H](OC(C)(C)C)C(=O)O)c(C)nc3sc4c(c23)CCCC4)c(O)c1]

or a pharmaceutically acceptable salt thereof.

2. A pharmaceutical composition comprising a compound as claimed in claim 1 together with a pharmaceutically acceptable excipient.

* * * * *